United States Patent
Parham et al.

(10) Patent No.: US 10,577,342 B2
(45) Date of Patent: Mar. 3, 2020

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt am Main (DE); Philipp Stoessel, Frankfurt am Main (DE); Thomas Eberle, Landau (DE); Anja Jatsch, Frankfurt am Main (DE); Jonas Valentin Kroeber, Frankfurt am Main (DE); Christof Pflumm, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 294 days.

(21) Appl. No.: 15/524,389

(22) PCT Filed: Oct. 13, 2015

(86) PCT No.: PCT/EP2015/002016
§ 371 (c)(1),
(2) Date: May 4, 2017

(87) PCT Pub. No.: WO2016/074755
PCT Pub. Date: May 19, 2016

(65) Prior Publication Data
US 2018/0282295 A1    Oct. 4, 2018

(30) Foreign Application Priority Data

Nov. 11, 2014 (EP) .................................... 14003784

(51) Int. Cl.
| | | |
|---|---|---|
| H01L 51/50 | (2006.01) |
| C07D 401/04 | (2006.01) |
| C07D 405/14 | (2006.01) |
| C07D 401/10 | (2006.01) |
| C07D 409/14 | (2006.01) |
| C07D 413/10 | (2006.01) |
| C07D 417/10 | (2006.01) |
| H01L 51/00 | (2006.01) |
| C07D 401/14 | (2006.01) |
| C07D 471/04 | (2006.01) |

(52) U.S. Cl.
CPC ......... *C07D 401/04* (2013.01); *C07D 401/10* (2013.01); *C07D 401/14* (2013.01); *C07D 405/14* (2013.01); *C07D 409/14* (2013.01); *C07D 413/10* (2013.01); *C07D 417/10* (2013.01); *C07D 471/04* (2013.01); *H01L 51/0072* (2013.01); *H01L 51/0073* (2013.01); *H01L 51/0074* (2013.01); *H01L 51/5016* (2013.01); *H01L 51/5056* (2013.01); *H01L 51/5096* (2013.01)

(58) Field of Classification Search
None
See application file for complete search history.

(56) References Cited

U.S. PATENT DOCUMENTS

2011/0156017 A1* 6/2011 Lee ..................... C07C 15/28
257/40

FOREIGN PATENT DOCUMENTS

| EP | 2327679 A2 | 6/2011 |
| JP | 2006151844 A | 6/2006 |
| WO | WO-2015046955 A1 | 4/2015 |

OTHER PUBLICATIONS

International Search Report for PCT/EP2015/002016 dated Feb. 2, 2016.
Written Opinion of the International Searching Authority for PCT/EP2015/002016 dated Feb. 2, 2016.

* cited by examiner

*Primary Examiner* — Gregory D Clark
(74) *Attorney, Agent, or Firm* — Drinker Biddle & Reath LLP

(57) ABSTRACT

The invention relates to compounds of the formula (1) which are suitable for use in electronic devices, in particular organic electroluminescent devices.

6 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2015/002016, filed Oct. 13, 2015, which claims benefit of European Application No. 14003784.7, filed Nov. 11, 2014, both of which are incorporated herein by reference in their entirety.

The present invention relates to phenanthridine derivatives, especially for use as triplet matrix materials or hole transport materials in organic electroluminescent devices. The invention further relates to a process for preparing the inventive compounds and to electronic devices comprising these compounds.

BACKGROUND OF THE INVENTION

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence rather than fluorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit triplet emission (phosphorescence), for example with regard to efficiency, operating voltage and lifetime.

The properties of phosphorescent OLEDs are not just determined by the triplet emitters used. More particularly, the other materials used, for example matrix materials, are also of particular significance here. Improvements to these materials can thus also lead to distinct improvements in the OLED properties.

According to the prior art, among other materials, indolocarbazole derivatives (for example according to WO 2007/063754 or WO 2008/056746) or indenocarbazole derivatives (for example according to WO 2010/136109 or WO 2011/000455), especially those substituted by electron-deficient heteroaromatics such as triazine, are used as matrix materials for phosphorescent emitters. In addition, for example, bisdibenzofuran derivatives (for example according to EP 2301926) are used as matrix materials for phosphorescent emitters. However, there is still a need for improvement in the case of use of these matrix materials, especially in relation to the efficiency, the lifetime and the operating voltage of the device.

BRIEF SUMMARY OF THE INVENTION

The problem addressed by the present invention is that of providing compounds suitable for use in a fluorescent or phosphorescent OLED, especially a phosphorescent OLED, for example as matrix material or as charge transport material, especially hole transport or electron blocker material. A particular problem addressed by the present invention is that of providing matrix materials which are also suitable for green- and blue-phosphorescing OLEDs, and providing novel charge transport materials.

It has been found that, surprisingly, electroluminescent devices containing compounds of the following formula (1) have improvements over the prior art, especially when used as matrix materials for phosphorescent dopants or hole transport materials.

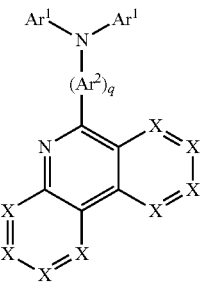

Formula (1)

where the symbols and indices used are as follows:

$Ar^1$ are the same or different at each instance and are an aromatic or heteroaromatic ring system which has 6 to 60 aromatic ring atoms and may in each case also be substituted by one or more $R^2$ radicals, in the case that q>0, at least the two $Ar^1$ may be joined and/or $Ar^1$ may be joined to $Ar^2$ via at least one bridge K;

K is the same or different at each instance and is a single bond or a bivalent bridge selected from $N(R^2)$, $B(R^2)$, O, C=O, $C(R^2)_2$, $Si(R^2)_2$, and S;

$Ar^2$ is the same or different at each instance and is a bivalent aromatic or heteroaromatic ring system which has 5 to 40 aromatic ring atoms and may be substituted by one or more $R^2$ radicals;

X is the same or different at each instance and is N or $CR^1$;

$R^1$ is the same or different at each instance and is H, D, F, Cl, Br, I, CHO, C(=O)(Ar), P(=O)(Ar)$_2$, S(=O)Ar, S(=O)$_2$Ar, CN, NO$_2$, Si(R$^2$)$_3$, B(OR$^2$)$_2$, OSO$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by C≡C, Si(R$^2$)$_2$, Ge(R$^2$)$_2$, Sn(R$^2$)$_2$, C=O, C=S, C=Se, P(=O)(R$^2$), SO, SO$_2$, O, S or CONR$^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents may also together form a mono- or polycyclic, aliphatic or aromatic ring system;

Ar is the same or different at each instance and is an aromatic or heteroaromatic ring system which has 6 to 60 aromatic ring atoms and may in each case also be substituted by one or more $R^2$ radicals;

$R^2$ is the same or different at each instance and is H, D, F, Cl, Br, I, CHO, C(=O)R$^3$, P(=O)(R$^3$)$_2$, S(=O)R$^3$, S(=O)$_2$R$^2$, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent CH$_2$ groups may be replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S or CONR$^3$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or a combination of these systems; at the same time, two or more $R^2$ substituents may also together form a mono- or polycyclic, aliphatic or aromatic ring system;

$R^3$ is the same or different at each instance and is H, D, F, Cl, Br, I, $N(R^4)_2$, C(=O)Ar, P(=O)$Ar_2$, S(=O)Ar, S(=O)$_2$Ar, $CR^4$=$CR^4$Ar, CN, $NO_2$, $Si(R^4)_3$, $B(OR^4)_2$, $OSO_2R^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent $CH_2$ groups may be replaced by $R^4C$≡$CR^4$, C≡C, $Si(R^4)_2$, C=O, C=$NR^4$, P(=O)($R^4$), SO, $SO_2$, $NR^4$, O, S or $CONR^4$ and where one or more hydrogen atoms may be replaced by D, F, Cl, Br, I, CN or $NO_2$, or an aromatic or heteroaromatic ring system which has 5 to 60 aromatic ring atoms, each of which may be substituted by one or more $R^4$ radicals, or an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals, or a combination of these systems; at the same time, two or more adjacent $R^3$ substituents may also together form a mono- or polycyclic, aliphatic or aromatic ring system;

$R^4$ is the same or different at each instance and is H, D, F or an aliphatic hydrocarbyl radical having 1 to 20 carbon atoms or an aryl or heteroaryl group which has 5 to 40 ring atoms and may be substituted by one or more $R^5$ radicals, or a combination of these groups;

$R^5$ is the same or different at each instance and is H, D, F or an aliphatic hydrocarbyl radical having 1 to 20 carbon atoms;

q is 0, 1 or 2;

where $Ar^2$ in the case of a heteroaromatic ring system may be joined to the phenanthridine base skeleton via a C—C bond; and, $R^1$ in the case of a heteroaromatic ring system may be joined to the phenanthridine base skeleton via a C—C bond.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example thiophene, etc., or a condensed (fused) aryl or heteroaryl group, for example naphthalene, anthracene, phenanthrene, dibenzofuran, etc. Aromatic systems joined to one another by a single bond, for example biphenyl, by contrast, are not referred to as an aryl or heteroaryl group but as an aromatic ring system.

An aromatic ring system in the context of this invention contains 6 to 80 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be joined by a nonaromatic unit (preferably less than 10% of the atoms other than H), for example a carbon, nitrogen or oxygen atom. For example, systems such as fluorene, 9,9'-spirobifluorene, 9,9-diarylfluorene, triarylamine, diaryl ethers, stilbene, etc. are also to be regarded as aromatic ring systems in the context of this invention, and likewise systems in which two or more aryl groups are joined, for example, by a short alkyl group. In addition, aromatic systems joined to one another by a single bond, for example biphenyl, are referred to as aromatic ring system in the context of this application.

An electron-deficient heteroaryl group in the context of present invention is defined as a 5-membered heteroaryl group having at least two heteroatoms, for example imidazole, oxazole, oxadiazole, etc., or as a 6-membered heteroaryl group having at least one heteroatom, for example pyridine, pyrimidine, pyrazine, triazine, etc. It is also possible for further 6-membered aryl or 6-membered heteroaryl groups to be fused onto these groups, as, for example, in benzimidazole or quinoline.

In the context of the present invention, an aliphatic hydrocarbyl radical or an alkyl group or an alkenyl or alkynyl group which may typically contain 1 to 40 or else 1 to 20 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-80 aromatic ring atoms and may also be substituted in each case by the abovementioned radicals and which may be joined to the aromatic or heteroaromatic system via any desired positions is especially understood to mean groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems. These groups may each be substituted by the abovementioned radicals.

An aryloxy group as defined in the present invention is understood to mean an aryl group as defined above bonded via an oxygen atom. An analogous definition applies to heteroaryloxy groups.

An electron-deficient heteroaryl group in the context of present invention is defined as a 5-membered heteroaryl group having at least two heteroatoms, for example imidazole, oxazole, oxadiazole, etc., or as a 6-membered heteroaryl group having at least one heteroatom, for example pyridine, pyrimidine, pyrazine, triazine, etc. It is also possible for further 6-membered aryl or 6-membered heteroaryl groups to be fused onto these groups, as, for example, in benzimidazole or quinoline.

The wording that two or more radicals together may form a ring, in the context of the present description, shall be understood to mean, inter alia, that the two radicals are joined to one another by a chemical bond. This is illustrated by the following scheme:

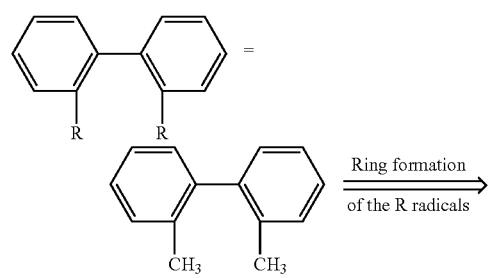

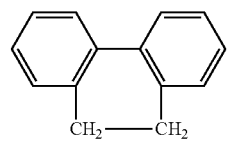

In addition, however, the abovementioned wording shall also be understood to mean that, if one of the two radicals is hydrogen, the second radical binds to the position to which the hydrogen atom was bonded, forming a ring. This shall be illustrated by the following scheme:

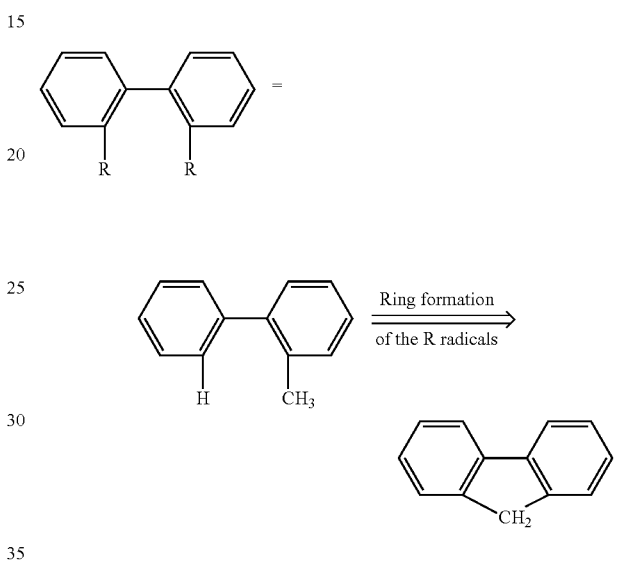

In a further embodiment of the invention, not more than 2× symbols in formula (1) are N. More preferably, no X symbol in formula (1) is N.

DETAILED DESCRIPTION OF THE INVENTION

A preferred embodiment of the compound of the formula (1) is a compound of the following formula (2):

Formula (2)

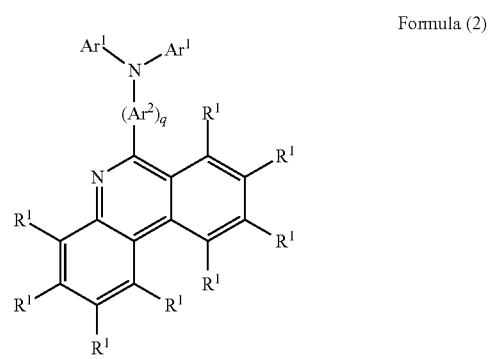

where the symbols and indices correspond to the definition in formula (1).

Preferred embodiments of formula (2) are shown by the following formulae (3) to (8):

Formula (3)

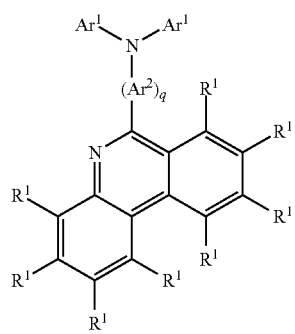

Formula (4)

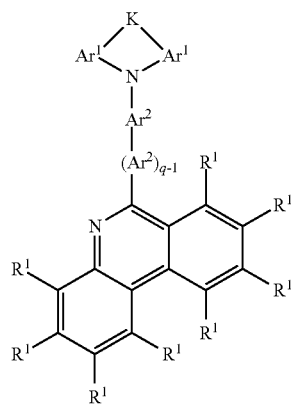

Formula (5)

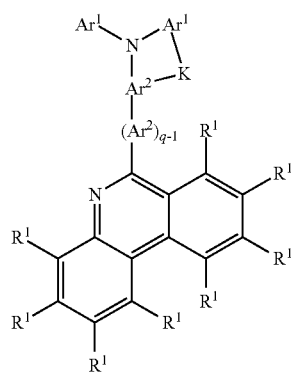

Formula (6)

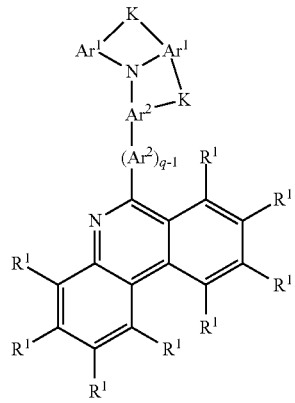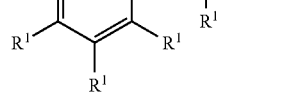

-continued

Formula (7)

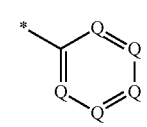

Formula (8)

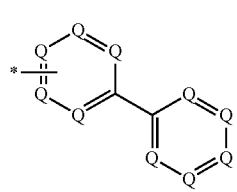

where the symbols and indices correspond to the symbols and indices of formula (1), and it is additionally the case that the two $Ar^1$ are not joined to one another and $Ar^1$ is not joined to $Ar^2$ by further K groups, and, in the formulae (4), (5), (6), (7) and (8), q is at least 1.

In a further embodiment of the invention, in formula (4), the $N(Ar^1)_2$ group which is joined via the K group forms a heteroaryl group having fewer than 20 aromatic ring atoms.

In a preferred embodiment of the invention, the compound does not comprise any aryl groups or heteroaryl groups having more than 22 aromatic ring atoms, preferably having more than 19 aromatic ring atoms. The effect of this is that the compounds exhibit better performance data in phosphorescent OLEDs.

In a preferred embodiment of the invention, the $Ar^1$ group at each instance is selected from the groups having the following formulae (Ar-1) to (Ar-13):

Formula (Ar-1)

Formula (Ar-2)

-continued

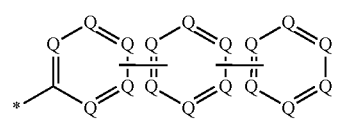
Formula (Ar-3)

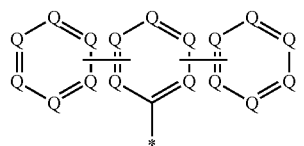
Formula (Ar-4)

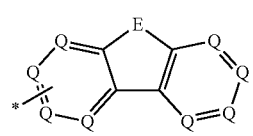
Formula (Ar-5)

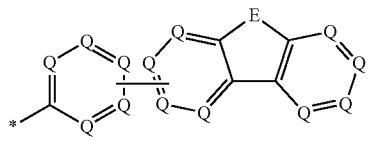
Formula (Ar-6)

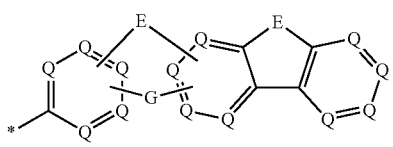
Formula (Ar-7)

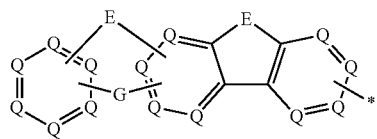
Formula (Ar-8)

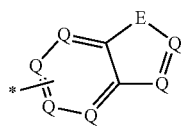
Formula (Ar-9)

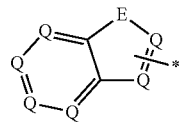
Formula (Ar-10)

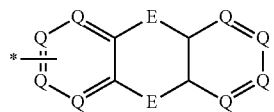
Formula (Ar-11)

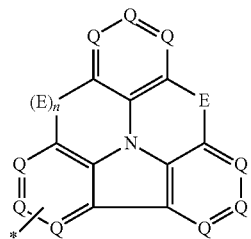
Formula (Ar-12)

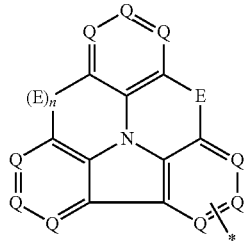
Formula (Ar-13)

where the symbols and indices correspond to the symbols and indices of formula (1) and, in addition:

Q is the same or different at each instance and is $CR^2$ or N, where not more than 3 Q symbols per cycle are N;

E is the same or different at each instance and is $(CR^2)_2$, $NR^2$, O, S or C=O;

G at each instance is a single bond, $(CR^2)_2$, $NR^2$, O, S or C=O;

n is 0 or 1, where n=0 means that no E group is bonded at this position and $R^2$ radicals are bonded to the corresponding carbon atoms instead; and

* represents the bond to the $Ar^2$—N group.

In a further embodiment of the invention, if the two $Ar^1$ groups are joined to one another by a K group, as also shown in formula (4), the —$N(Ar^1)_2$ group is selected from one of the following formulae (Ar1-1) to (Ar1-6), preference being given to groups selected from the following formulae (Ar1-1), (Ar1-2), (Ar1-4), (Ar1-5) and (Ar1-6):

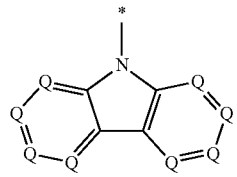
Formula (Ar1-1)

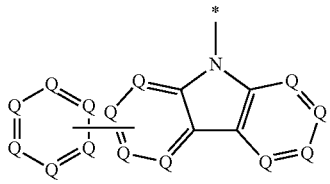
Formula (Ar1-2)

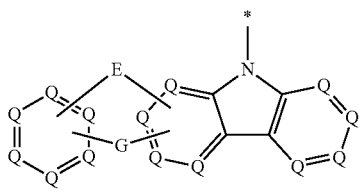
Formula (Ar1-3)

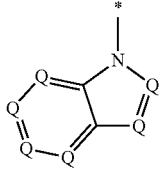
Formula (Ar1-4)

Formula (Ar1-5)

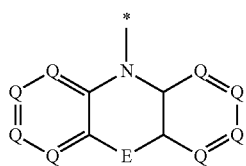

Formula (Ar1-6)

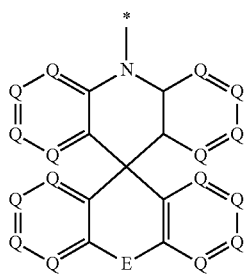

where the symbols and indices correspond to the symbols and indices of formula (1) and, in addition, for the formulae (Ar1-1) to (Ar1-6):

Q is the same or different at each instance and is $CR^2$ or N, where not more than 2 Q symbols per cycle are N;

E is the same or different at each instance and is $(CR^2)_2$, $NR^2$, O, S or C=O;

G at each instance is a single bond, $(CR^2)_2$, $NR^2$, O, S or C=O;

n is 0 or 1, where n=0 means that no E group is bonded at this position and $R^2$ radicals are bonded to the corresponding carbon atoms instead;

* represents the bond to the $Ar^2$ group.

In a further preferred embodiment, in the formula (Ar-1), 0, 2 or 3 Q symbols are N.

Preferred embodiments of the formula (Ar-8) are shown by the following formulae (Ar-8-1) to (Ar-8-7):

Formula (Ar-8-1)

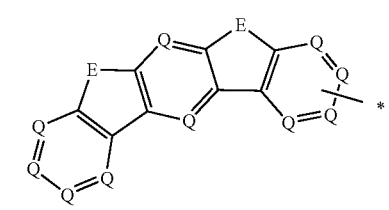

Formula (Ar-8-2)

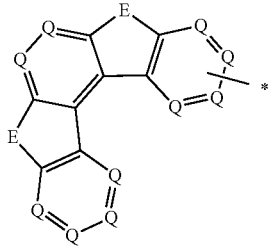

Formula (Ar-8-3)

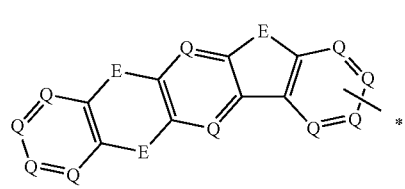

Formula (Ar-8-4)

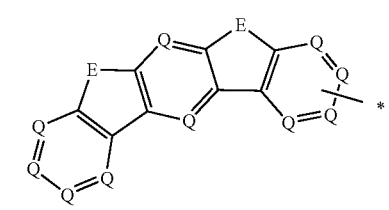

Formula (Ar-8-5)

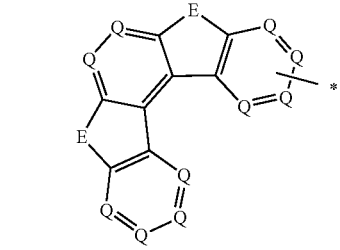

Formula (Ar-8-6)

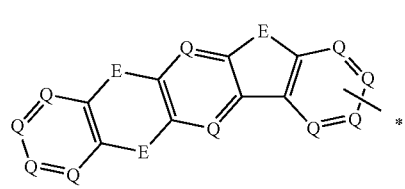

Formula (Ar-8-7)

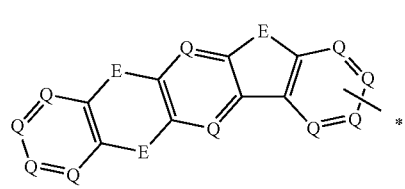

where the symbols correspond to the symbols of the formula (Ar-8). More preferably, Q is always $CR^2$.

In a further preferred embodiment, the $Ar^1$ group is the same or different at each instance and is selected from the groups having the structures of formulae (Ar-1) to (Ar-13), where the general formulae are replaced by the respective particularly preferred embodiments of the following formulae (Ar-1-1) to (Ar-13-1) (for example, formula (Ar-1) is replaced by one of the formulae (Ar-1-1) to (Ar-1-9)):

Formula (Ar-1-1)

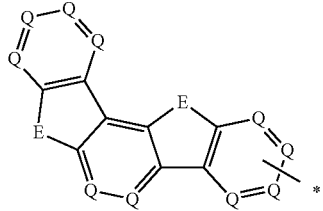

Formula (Ar-1-2)

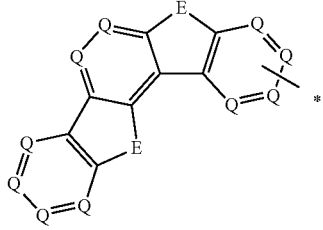

Formula (Ar-1-3)

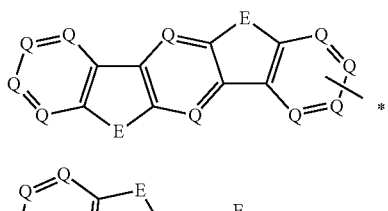

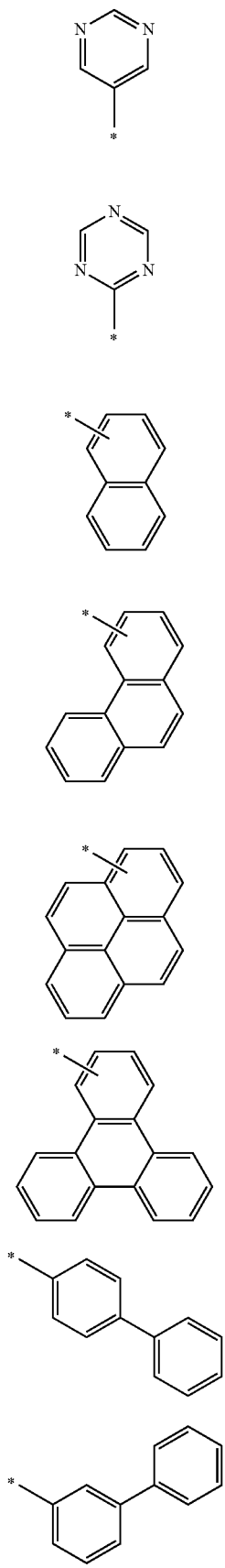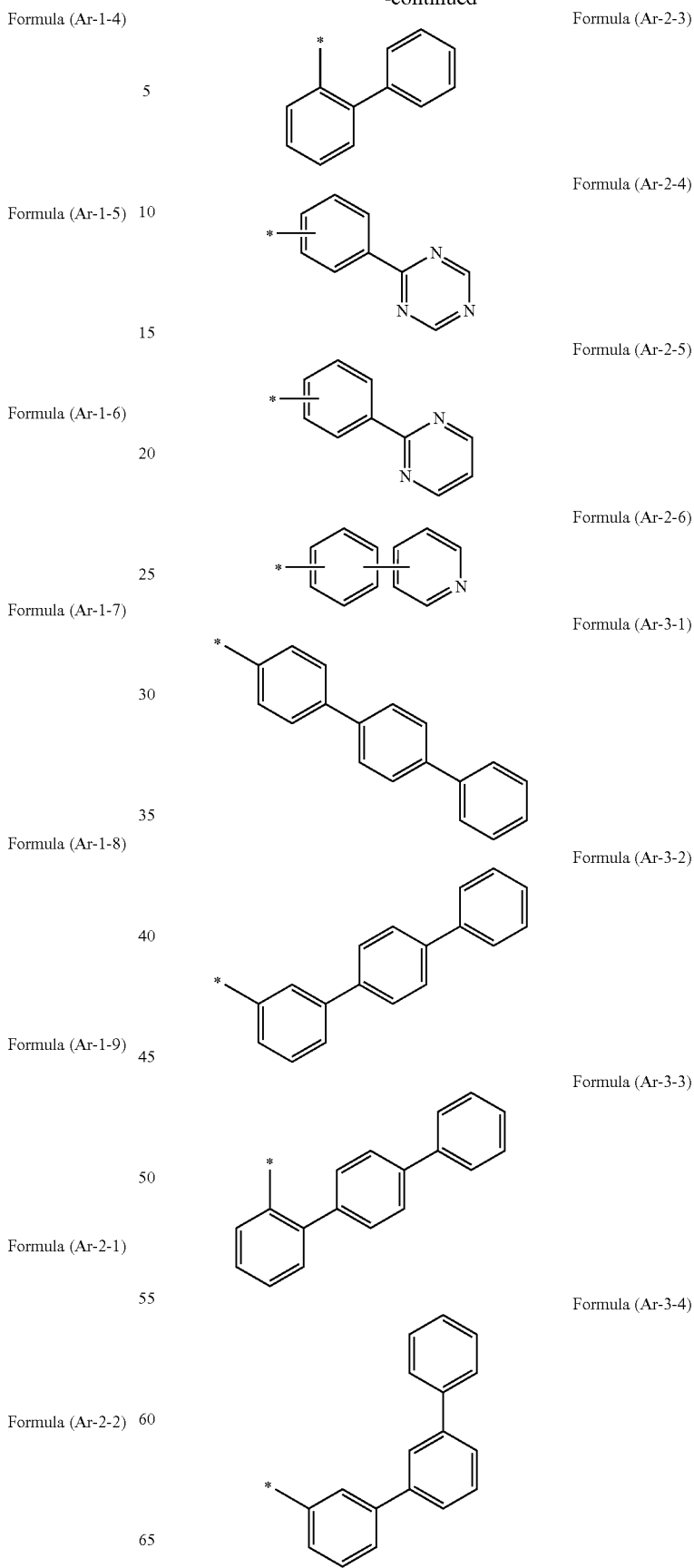

Formula (Ar-3-5)
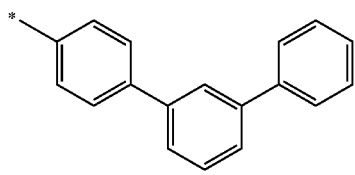
Formula (Ar-3-6)
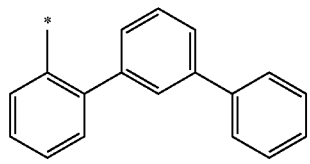
Formula (Ar-3-7)
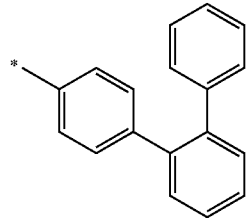
Formula (Ar-3-8)
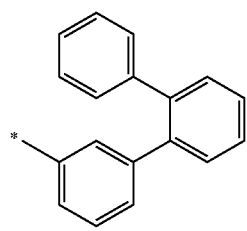
Formula (Ar-3-9)
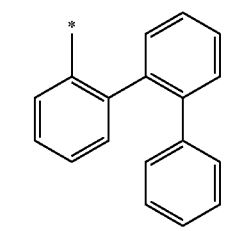
Formula (Ar-4-1)
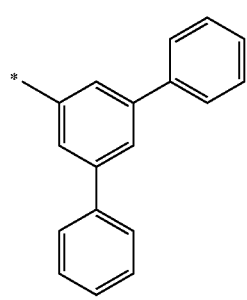
Formula (Ar-4-2)
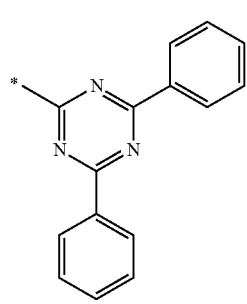
Formula (Ar-4-3)
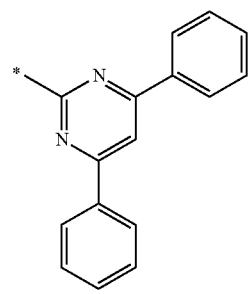
Formula (Ar-4-4)
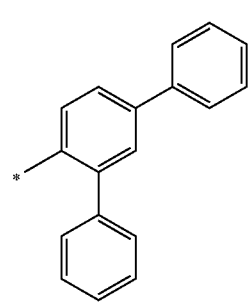
Formula (Ar-5-1)
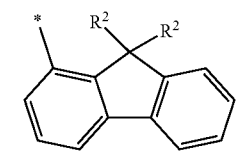
Formula (Ar-5-2)
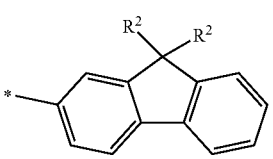
Formula (Ar-5-3)
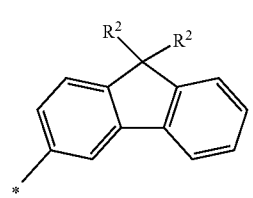
Formula (Ar-5-4)
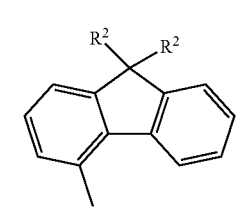
Formula (Ar-5-5)
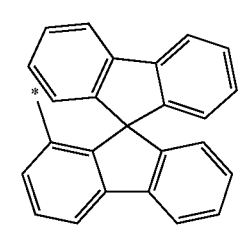

Formula (Ar-5-6)
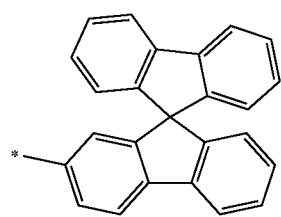
Formula (Ar-5-7)
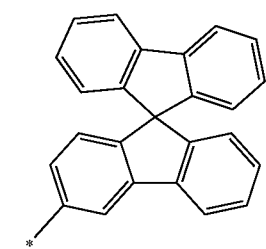
Formula (Ar-5-8)
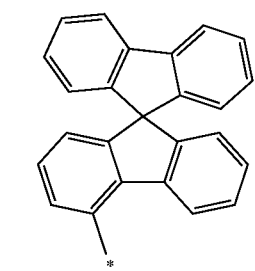
Formula (Ar-5-9)
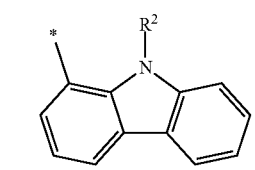
Formula (Ar-5-10)
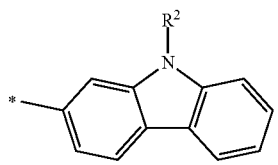
Formula (Ar-5-11)
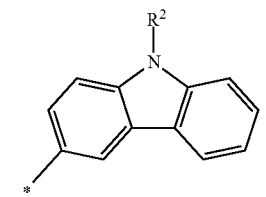
Formula (Ar-5-12)
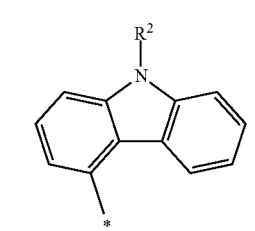
Formula (Ar-5-13)
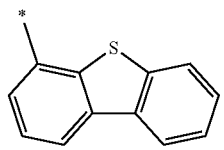
Formula (Ar-5-14)
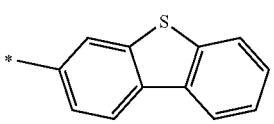
Formula (Ar-5-15)
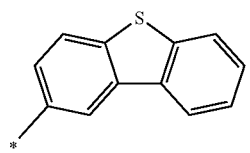
Formula (Ar-5-16)
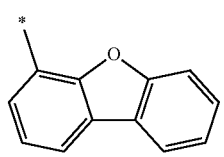
Formula (Ar-5-17)
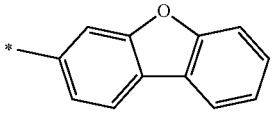
Formula (Ar-5-18)
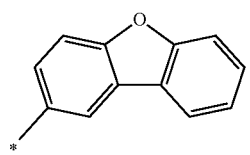
Formula (Ar-5-19)
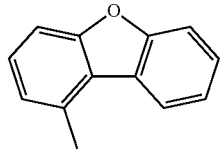
Formula (Ar-5-20)
Formula (Ar-6-1)

Formula (Ar-6-2)
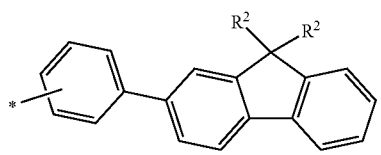
Formula (Ar-6-3)
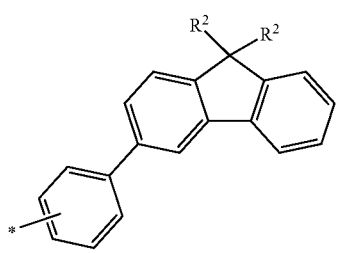
Formula (Ar-6-4)
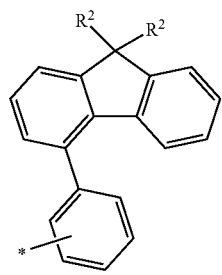
Formula (Ar-6-5)
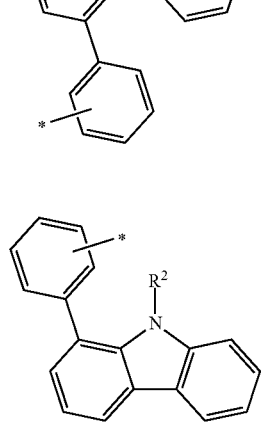
Formula (Ar-6-6)
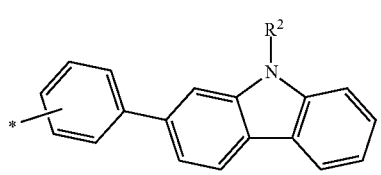
Formula (Ar-6-7)
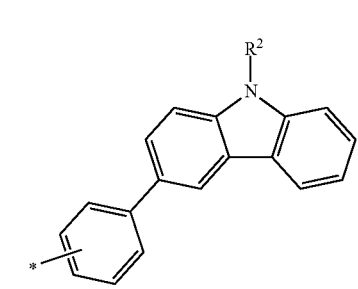
Formula (Ar-6-8)
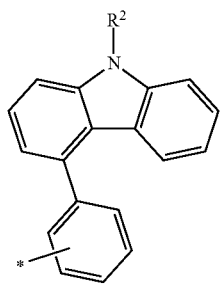
Formula (Ar-6-9)
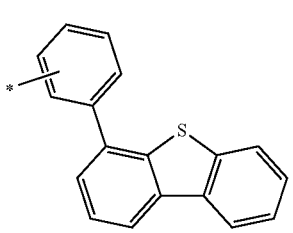
Formula (Ar-6-10)
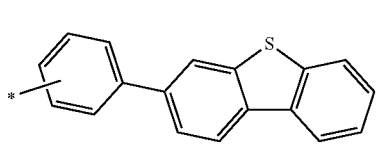
Formula (Ar-6-11)
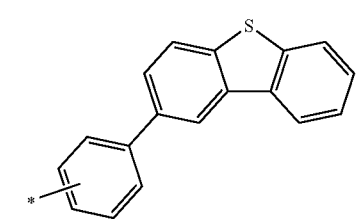
Formula (Ar-6-12)
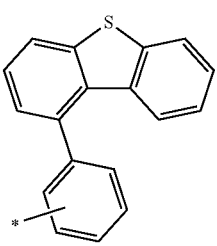
Formula (Ar-6-13)
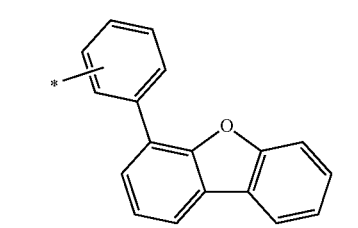
Formula (Ar-6-14)
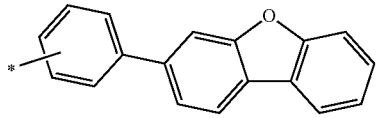

Formula (Ar-6-15)
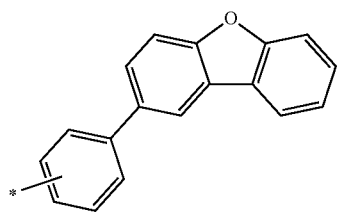
Formula (Ar-6-16)
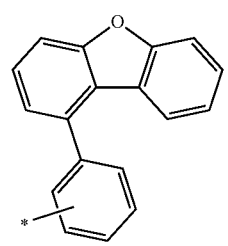
Formula (Ar-8-1-1)
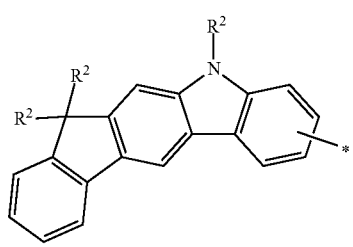
Formula (Ar-8-1-2)
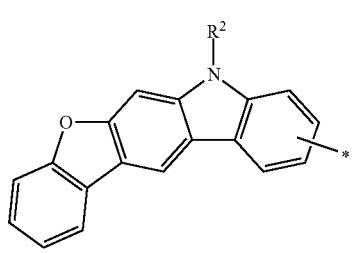
Formula (Ar-8-1-3)
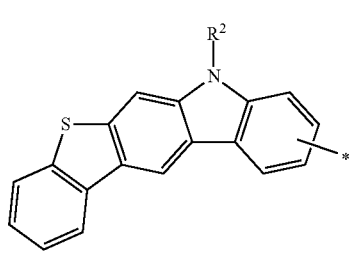
Formula (Ar-8-1-4)
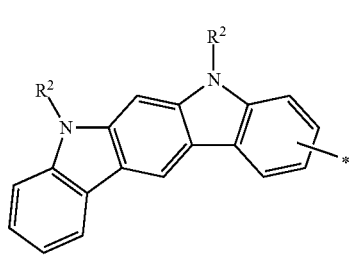
Formula (Ar-8-1-5)
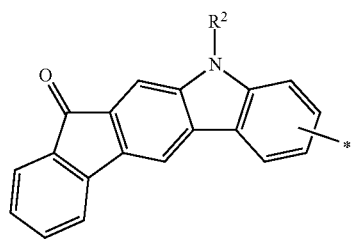
Formula (Ar-8-1-6)
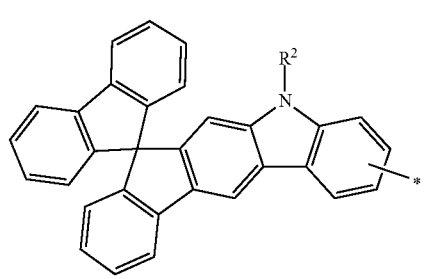
Formula (Ar-8-2-1)
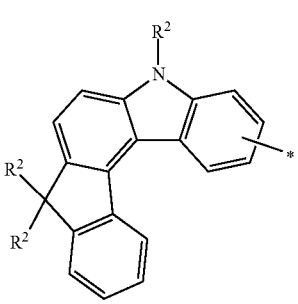
Formula (Ar-8-2-2)
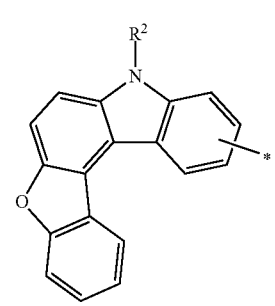
Formula (Ar-8-2-3)
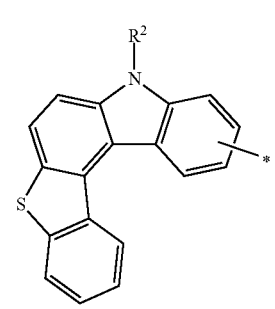

Formula (Ar-8-2-4)
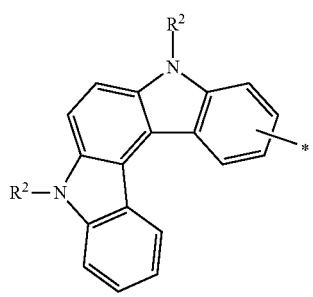
Formula (Ar-8-2-5)
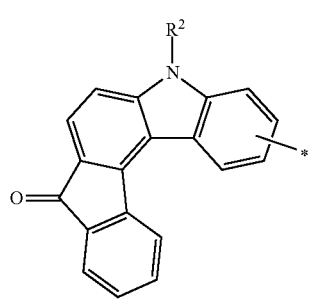
Formula (Ar-8-2-6)
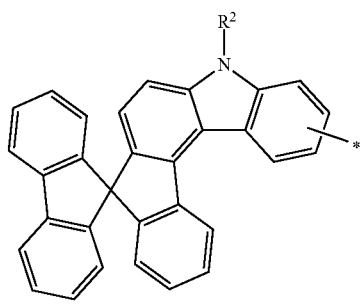
Formula (Ar-8-3-1)
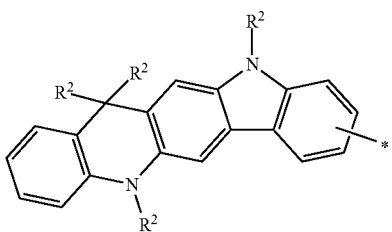
Formula (Ar-8-3-2)
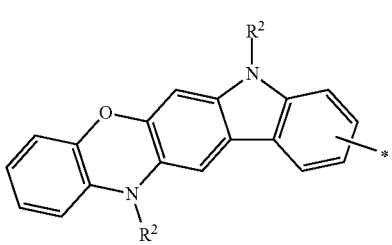
Formula (Ar-8-3-3)
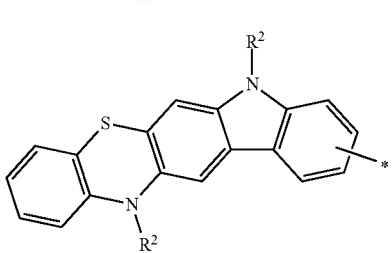
Formula (Ar-8-3-4)
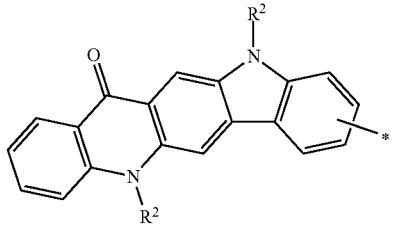
Formula (Ar-8-4-1)
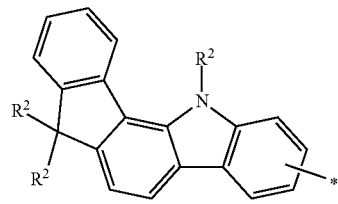
Formula (Ar-8-4-2)
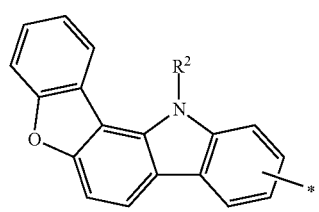
Formula (Ar-8-4-3)
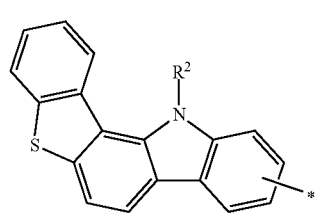
Formula (Ar-8-4-4)
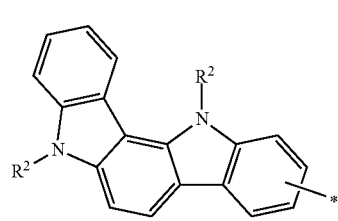
Formula (Ar-8-4-5)
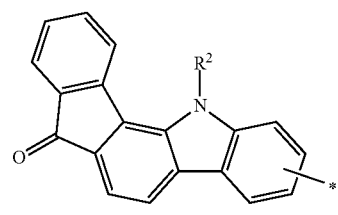
Formula (Ar-8-4-6)

Formula (Ar-8-5-1)
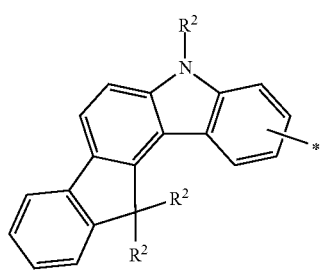
Formula (Ar-8-5-2)
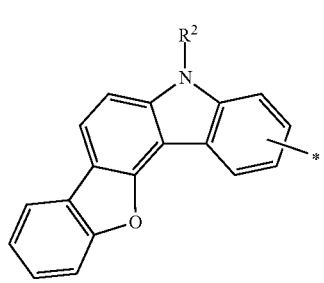
Formula (Ar-8-5-3)
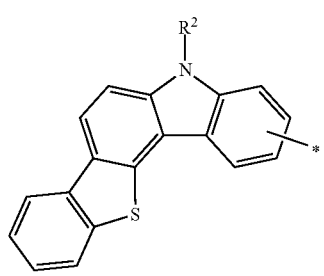
Formula (Ar-8-5-4)
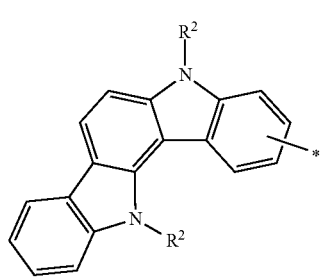
Formula (Ar-8-5-5)
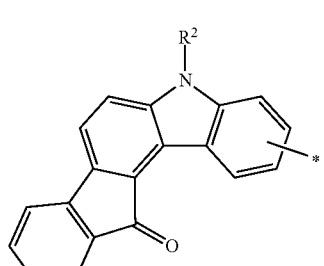
Formula (Ar-8-5-6)
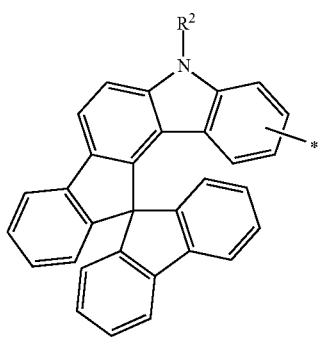
Formula (Ar-8-6-1)
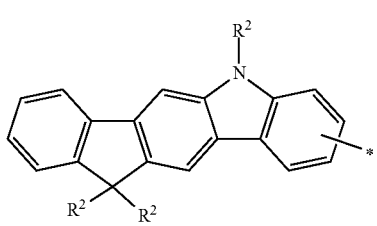
Formula (Ar-8-6-2)
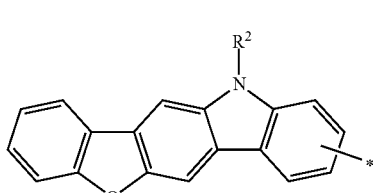
Formula (Ar-8-6-3)
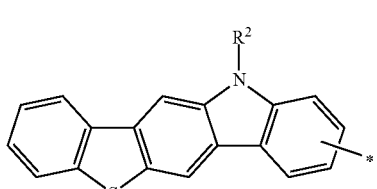
Formula (Ar-8-6-4)
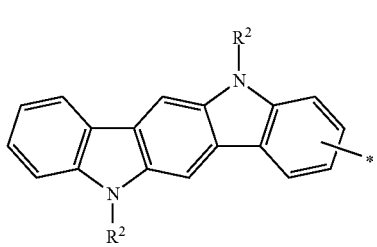
Formula (Ar-8-6-5)
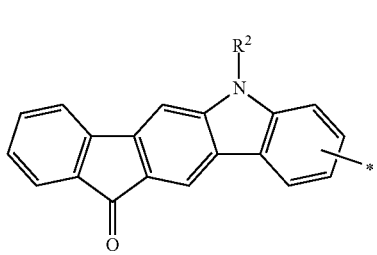

Formula (Ar-8-6-6)
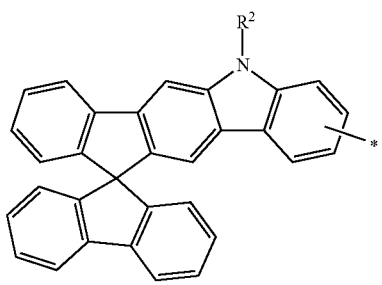
Formula (Ar-8-7-1)
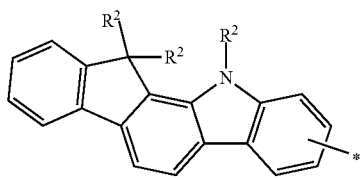
Formula (Ar-8-7-2)
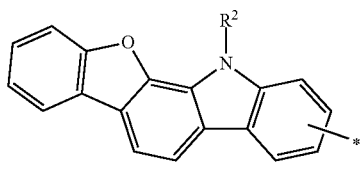
Formula (Ar-8-7-3)
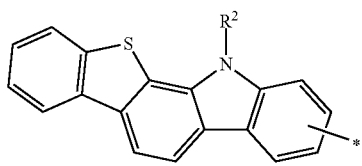
Formula (Ar-8-7-4)
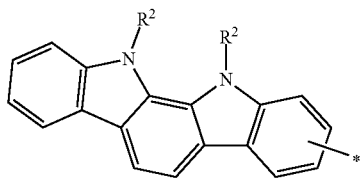
Formula (Ar-8-7-5)
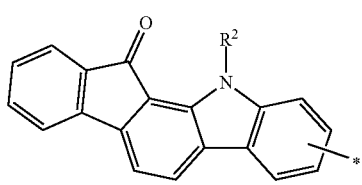
Formula (Ar-8-7-6)
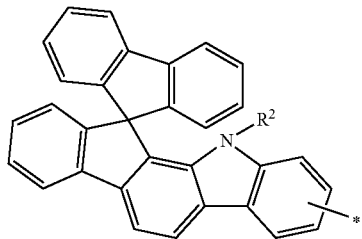
Formula (Ar-9-1)
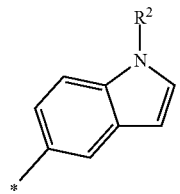
Formula (Ar-10-1)
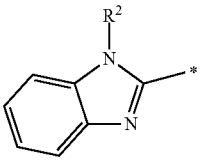
Formula (Ar-11-1)
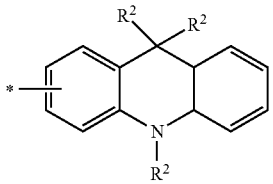
Formula (Ar-11-2)
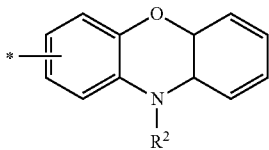
Formula (Ar-11-3)
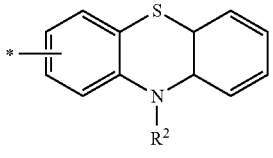
Formula (Ar-11-4)
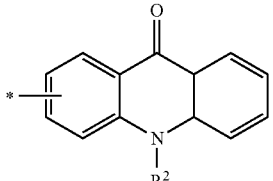
Formula (Ar-12-1)
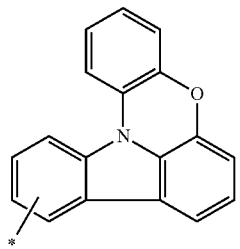
Formula (Ar-12-2)
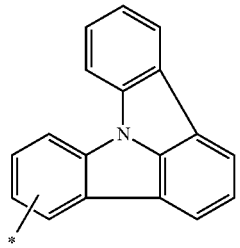

Formula (Ar-13-1)

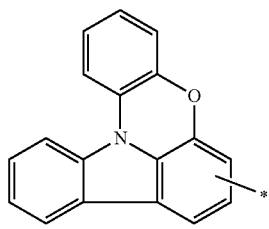

where the symbols correspond to the symbols in formula (1). The formulae may be substituted by $R^2$ at the free positions.

In a further embodiment of the invention, if the two $Ar^1$ groups are bonded to one another by a K group, as also shown in formula (4), the $N(Ar^1)_2$ group is selected from one of the formulae (Ar1-1) to (Ar1-6), preferably selected from the following formulae (Ar1-1), (Ar1-2), (Ar1-4), (Ar1-5) and (Ar1-6), where the general formulae are replaced in each case by the particularly preferred embodiments of the following formulae (Ar1-1-1) to (Ar1-6-1) (for example, formula (Ar1-1) is replaced by the formulae (Ar1-1-1)):

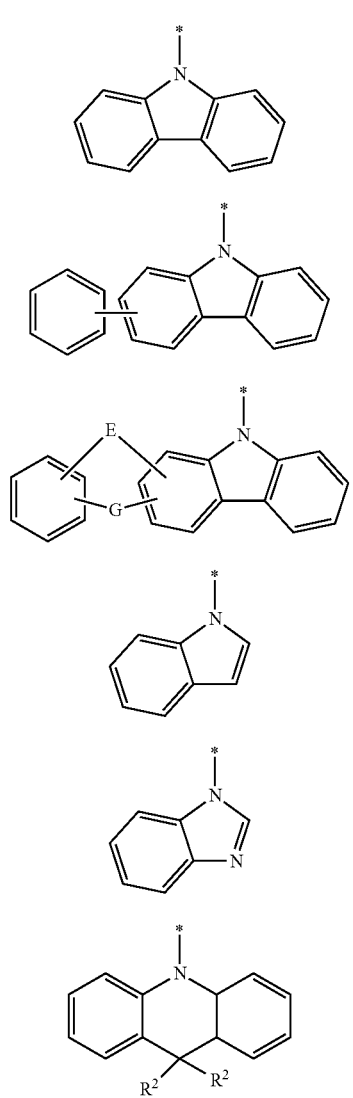

Formula (Ar1-1-1)

Formula (Ar1-2-1)

Formula (Ar1-3-1)

Formula (Ar1-4-1)

Formula (Ar1-4-2)

Formula (Ar1-5-1)

Formula (Ar1-5-2)

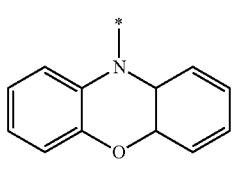

Formula (Ar1-5-3)

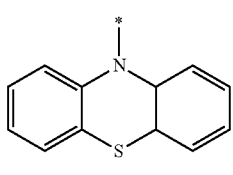

Formula (Ar1-5-4)

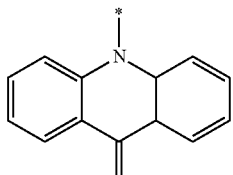

Formula (Ar1-6-1)

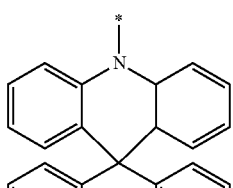

Formula (Ar1-6-2)

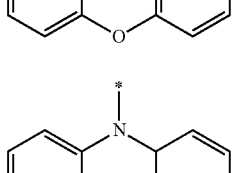

where the symbols correspond to the symbols in the formulae (Ar1-1) to (Ar1-6). The formulae may be substituted by $R^2$ at the free positions.

In a further embodiment of the invention, the groups of formula (Ar-8) or preferred embodiments thereof are selected from the groups of one of the formulae (Ar-8-1-1a) to (Ar-8-7-6a):

Formula (Ar-8-1-1a)

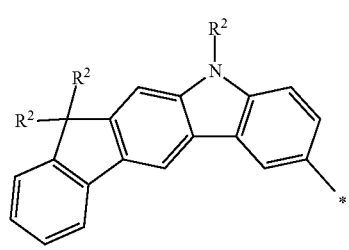

Formula (Ar-8-1-2a)
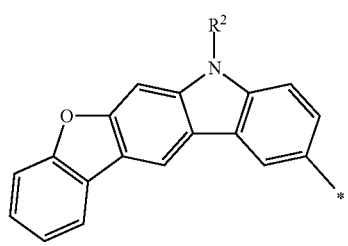
Formula (Ar-8-1-3a)
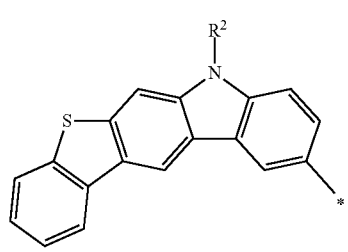
Formula (Ar-8-1-4a)
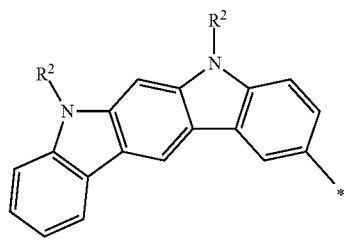
Formula (Ar-8-1-5a)
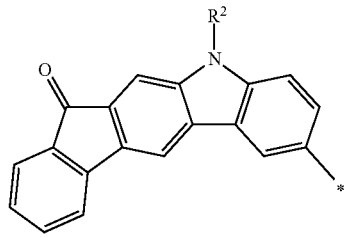
Formula (Ar-8-1-6a)
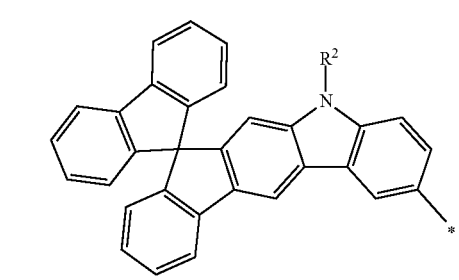
Formula (Ar-8-2-1a)
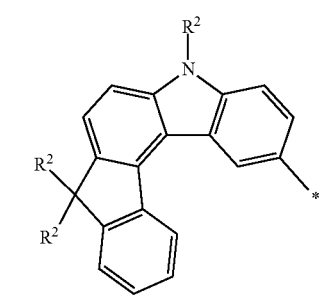
Formula (Ar-8-2-2a)
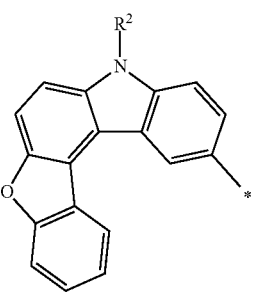
Formula (Ar-8-2-3a)
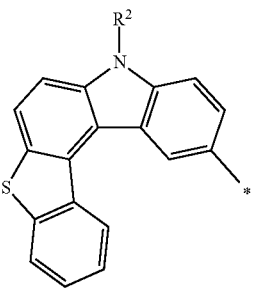
Formula (Ar-8-2-4a)
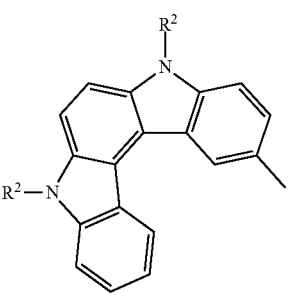
Formula (Ar-8-2-5a)
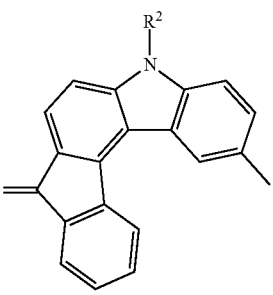
Formula (Ar-8-2-6a)
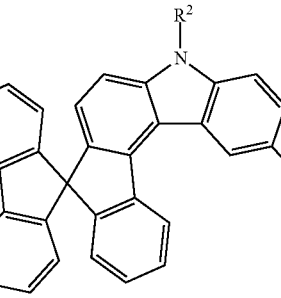

Formula (Ar-8-3-1a)
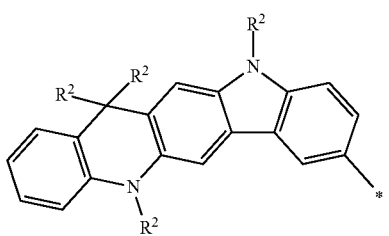
Formula (Ar-8-3-2a)
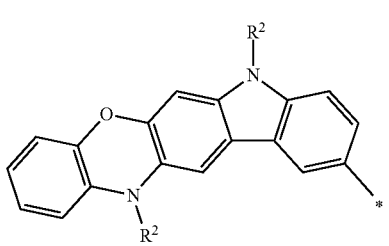
Formula (Ar-8-3-3a)
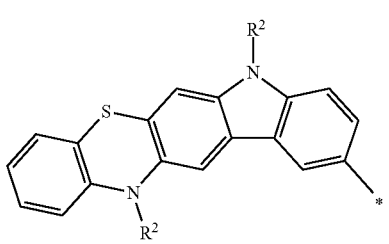
Formula (Ar-8-3-4a)
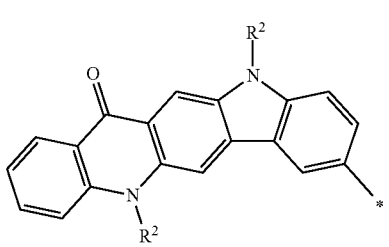
Formula (Ar-8-4-1a)
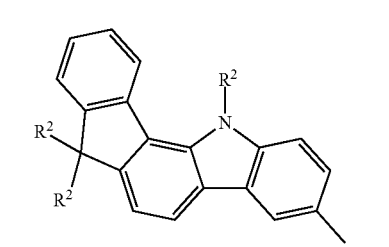
Formula (Ar-8-4-2a)
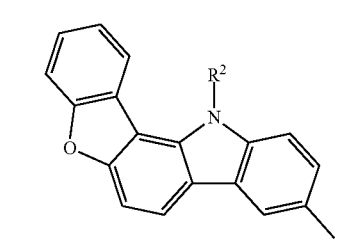
Formula (Ar-8-4-3a)
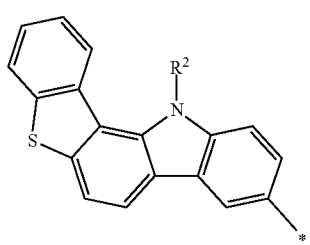
Formula (Ar-8-4-4a)
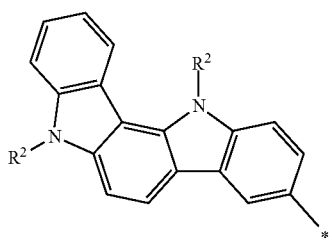
Formula (Ar-8-4-5a)
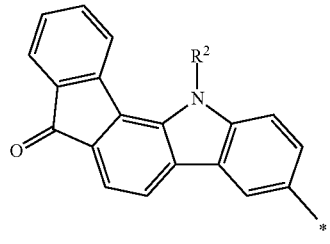
Formula (Ar-8-4-6a)
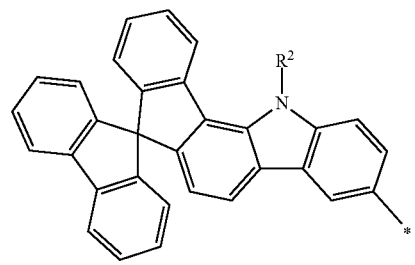
Formula (Ar-8-5-1a)
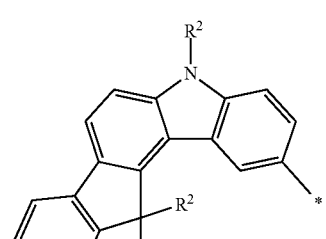
Formula (Ar-8-5-2a)
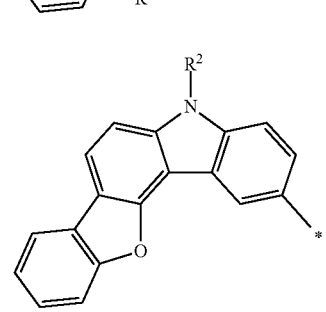

Formula (Ar-8-5-3a)
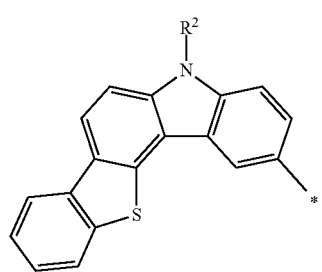
Formula (Ar-8-5-4a)
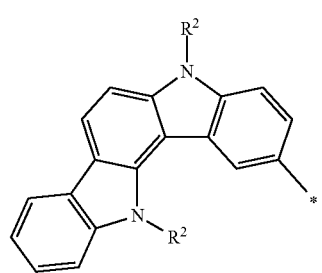
Formula (Ar-8-5-5a)
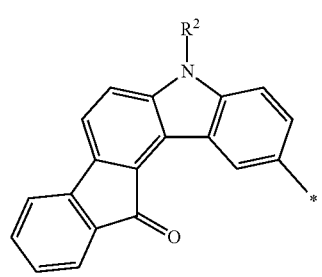
Formula (Ar-8-5-6a)
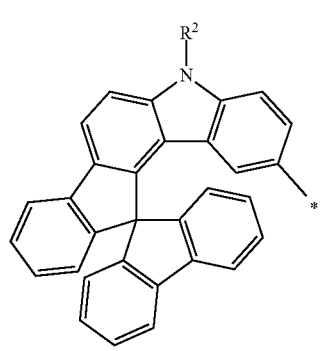
Formula (Ar-8-6-1a)
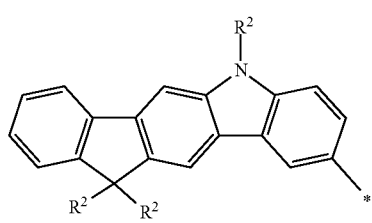
Formula (Ar-8-6-2a)
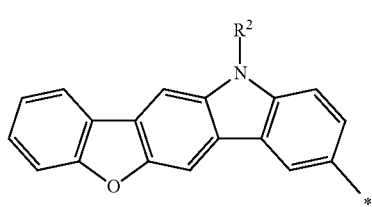
Formula (Ar-8-6-3a)
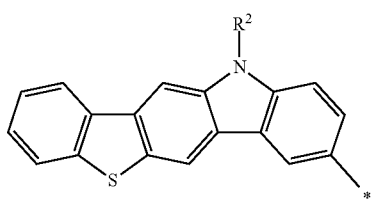
Formula (Ar-8-6-4a)
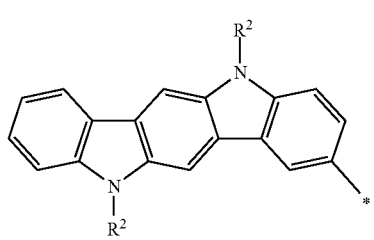
Formula (Ar-8-6-5a)
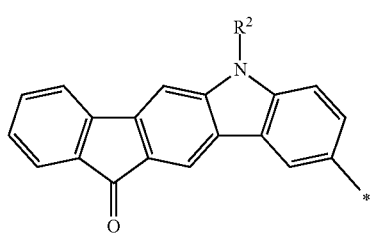
Formula (Ar-8-6-6a)
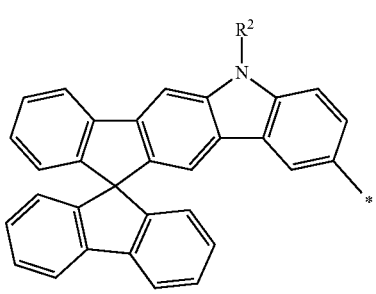
Formula (Ar-8-7-1a)
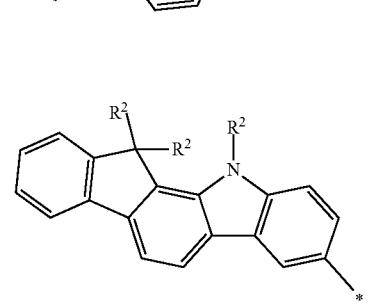
Formula (Ar-8-7-2a)
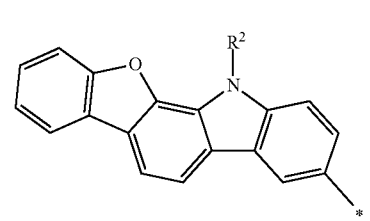

Formula (Ar-8-7-3a)
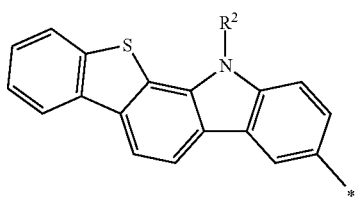

Formula (Ar-8-7-4a)
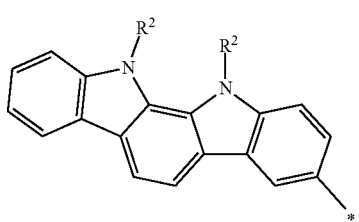

Formula (Ar-8-7-5a)
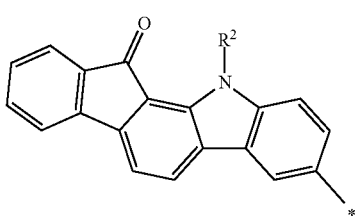

Formula (Ar-8-7-6a)
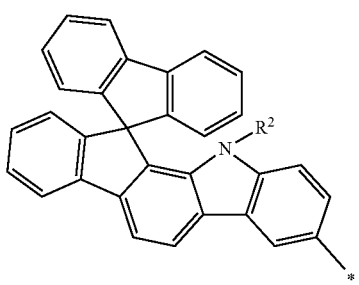

where the symbols correspond to the symbols in formula (Ar-8). The formulae may be substituted by $R^2$ at the free positions.

The $Ar^2$ group, if present, is the same or different at each instance and is preferably a bivalent aromatic or heteroaromatic ring system having 6 to 24 aromatic ring atoms. Preferred $Ar^2$ group at each instance is the same or different and are selected from the group consisting of ortho-, meta- or para-benzene, ortho-, meta- or para-biphenyl, terphenyl, especially ortho-, meta- or para-terphenyl, quaterphenyl, especially ortho-, meta- or para-quaterphenyl, fluorene, 9,9'-spirobifluorene, furan, benzofuran, dibenzofuran, dibenzothiophene, pyrrole, indole or carbazole or combinations of these groups, where the divalent bond to the base skeleton in the case of heteroaromatic ring systems is not via the nitrogen atom. These groups may be substituted by one or more $R^2$ radicals, but are preferably unsubstituted.

In a further embodiment of the invention, the $Ar^2$ group is selected from the formulae (Ar2-1) to (Ar2-14):

Formula (Ar2-1)
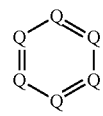

Formula (Ar2-2)
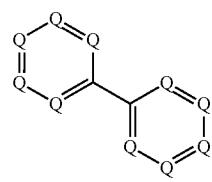

Formula (Ar2-3)
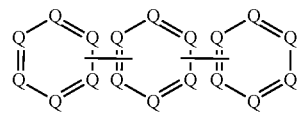

Formula (Ar2-4)
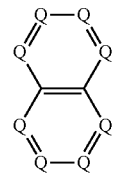

Formula (Ar2-5)
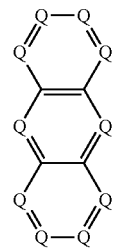

Formula (Ar2-6)
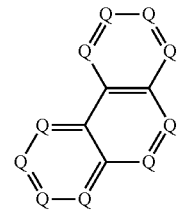

Formula (Ar2-7)
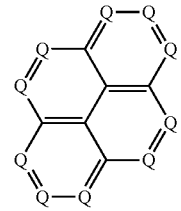

Formula (Ar2-8)
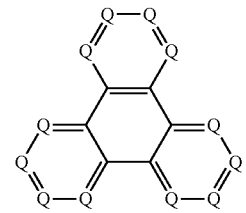

-continued

Formula (Ar2-9)

Formula (Ar2-10)

Formula (Ar2-11)

Formula (Ar2-12)

Formula (Ar2-13)

Formula (Ar2-14)

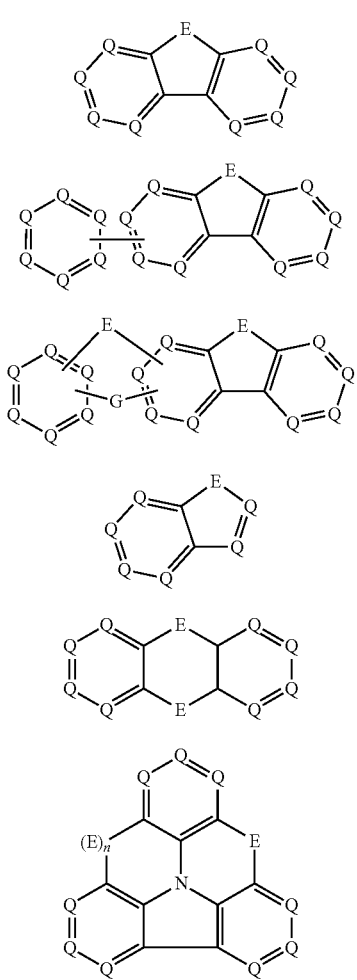

where the symbols and indices correspond to the symbols and indices of the formula (1) and, in addition:
Q is the same or different at each instance and is $CR^2$ or N, where not more than three Q symbols per cycle are N;
E is the same or different at each instance and is $(CR^2)_2$, $NR^2$, O, S or C=O;
G at each instance is a single bond, $(CR^2)_2$, $NR^2$, O, S or C=O;
n is 0 or 1, where n=0 means that no E group is attached at this position and, instead, $R^2$ radicals are attached to the corresponding carbon atoms; and
the formulae have, as bivalent aromatic or heteroaromatic ring systems, one bond at each of at least two positions to one of the adjacent groups as per formula (1), selected from N, $Ar^2$ and phenanthridine base skeleton.

The bond to the phenanthridine base skeleton is always a C—C bond.

In a preferred embodiment, $Ar^2$ is selected from the formulae (Ar2-1-1) to (Ar2-13-2):

Formula (Ar2-1-1)

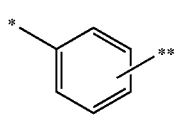

Formula (Ar2-1-2)

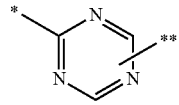

Formula (Ar2-1-2)

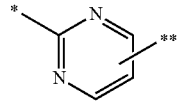

Formula (Ar2-1-3)

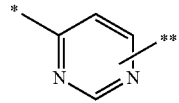

Formula (Ar2-1-4)

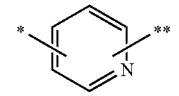

Formula (Ar2-2-1)

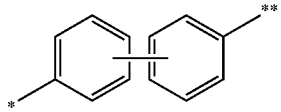

Formula (Ar-2-2-2)

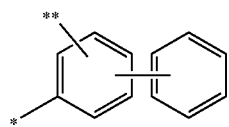

Formula (Ar-2-2-3)

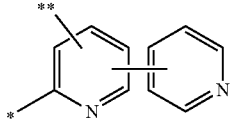

Formula (Ar-2-2-4)

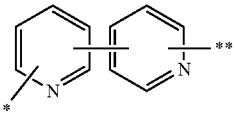

Formula (Ar2-3-1)

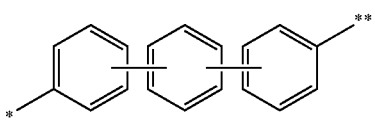

Formula (Ar2-4-1)

Formula (Ar2-4-2)

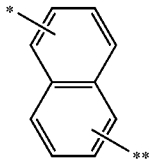

-continued

Formula (Ar2-6-1)
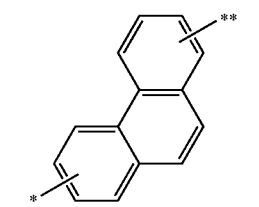

Formula (Ar2-6-2)
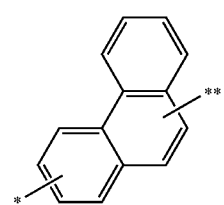

Formula (Ar2-6-3)
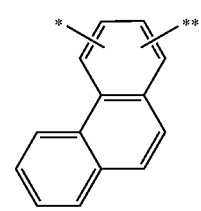

Formula (Ar2-8-1)
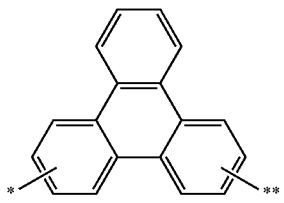

Formula (Ar2-9-1)
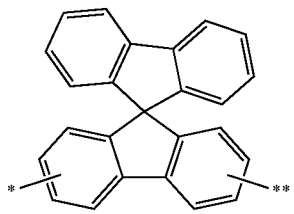

Formula (Ar2-9-2)
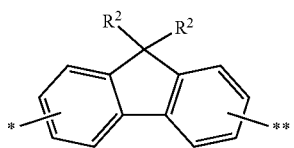

Formula (Ar2-9-3)
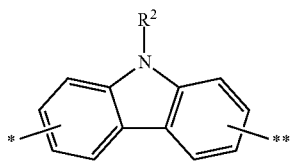

Formula Ar2-9-4)
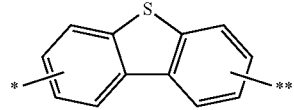

Formula (Ar2-9-5)
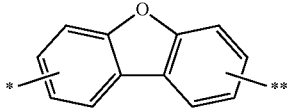

Formula (Ar2-9-6)
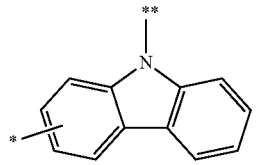

Formula (Ar2-13-1)
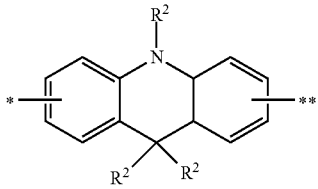

Formula (Ar2-13-2)
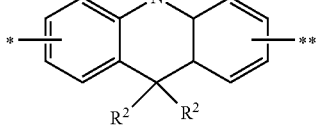

Formula (Ar2-13-3)
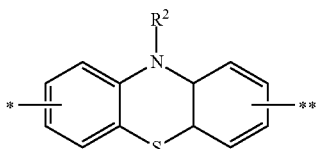

where the symbols used for formula (1) have the definitions given and the bond identified by * and  represent the bonds of the bivalent aromatic or heteroaromatic ring system to the adjacent groups, the bond being a C—C, C—N or N—C bond. This means, for example, that, in the case of the formula (Ar2-9-6), the bond identified by  cannot be joined to the N of formula (1). The groups may be substituted by $R^2$ at the free positions. They are preferably unsubstituted.

If * or  represents the bond to the phenanthridine base skeleton, it is a C—C bond. This means that  in the formula (Ar2-9-6) is not a bond to the phenanthridine base skeleton. Other $Ar^2$ may have a C—N or N—C bond to other $Ar^2$.

In a further embodiment of the invention, $Ar^2$ does not include any aromatic or heteroaromatic ring system having more than 19 aromatic ring atoms.

If the $Ar^2$ group is joined to at least one of the $Ar^1$ groups, as also shown in formula (5) and formula (6), the $Ar^2$—N$(Ar^1)_2$ group is preferably selected from the structures of the formulae (Ar-5) to (Ar-9) and (Ar-11), (Ar-12) and (Ar-13), where the symbols and indices correspond to the symbols and indices of the formulae (Ar-5) to (Ar-9) and (Ar-11), (Ar-12) and (Ar-13) and, in addition:

E is the same or different at each instance and is $(CR^2)_2$, $NR^2$, O, S or C=O, where one E is N—$Ar^1$;
* represents the bond to the phenanthridine base skeleton or, if present, to an $Ar^2$ group.

Preferred structures for the $Ar^2$—N$(Ar^1)_2$ group when the $Ar^2$ group is joined to at least one of the $Ar^1$ groups are the structures of the formulae (Ar-5-9), (Ar-5-10), (Ar-5-11), (Ar-5-12), (Ar-6-5), (Ar-6-6), (Ar-6-7), (Ar-6-8), (Ar-8-1-1), (Ar-8-1-2), (Ar-8-1-3), (Ar-8-1-4), (Ar-8-1-5), (Ar-8-1-6), (Ar-8-2-1), (Ar-8-2-2), (Ar-8-2-3), (Ar-8-2-4), (Ar-8-2-5), (Ar-8-2-6), (Ar-8-3-1), (Ar-8-3-2), (Ar-8-3-3), (Ar-8-3-4), (Ar-8-4-1), (Ar-8-4-2), (Ar-8-4-3), (Ar-8-4-4) (Ar-8-4-5), (Ar-8-4-6), (Ar-8-5-1), (Ar-8-5-2), (Ar-8-5-3), (Ar-8-5-4), (Ar-8-5-5), (Ar-8-5-6), (Ar-8-6-1), (Ar-8-6-2), (Ar-8-6-3), (Ar-8-6-4), (Ar-8-6-5), (Ar-8-6-6), (Ar-8-7-1), (Ar-8-7-2), (Ar-8-7-3), (Ar-8-7-4), (Ar-8-7-5), (Ar-8-7-6), (Ar-11-1), (Ar-11-2), (Ar-11-3), (Ar-11-4), (Ar-13-1) or the respectively preferred embodiments of the formulae, where the symbols and indices correspond to the symbols and indices of the formulae (Ar-5) to (Ar-9) and (Ar-11), (Ar-12) and (Ar-13) and, in addition:
$R^2$ when bonded to N is $Ar^1$ at one instance;
represents the bond to the phenanthridine base skeleton or, if present, to an $Ar^2$ group.

In a preferred embodiment of the invention, $R^1$ is the same or different at each instance and are selected from the group consisting of H, D, F, $Si(R^2)_3$, CN, a straight-chain alkyl or alkoxy group having 1 to 10 carbon atoms or a branched or cyclic alkyl or alkoxy group having 3 to 10 carbon atoms, each of which may be substituted by one or more $R^2$ radicals, where one or more nonadjacent $CH_2$ groups may be replaced by 0 and where one or more hydrogen atoms may be replaced by D or F, an aromatic or heteroaromatic ring system which has 6 to 60 aromatic ring atoms and may be substituted in each case by one or more $R^2$ radicals, where two or more adjacent $R^1$ substituents may optionally form a mono- or polycyclic aliphatic ring system.

In a further preferred embodiment of the invention, not more than four R' are an aromatic or heteroaromatic ring system which has 6 to 60 aromatic ring atoms and may be substituted in each case by one or more $R^2$ radicals, where two or more adjacent $R^1$ substituents may optionally form a mono- or polycyclic aliphatic ring system.

In a further preferred embodiment, no two or more adjacent $R^1$ substituents may form a mono- or polycyclic aliphatic ring system. More particularly, no further aromatic rings are fused to the phenanthridine base skeleton.

In a further preferred embodiment of the invention, R' in the case of an aromatic or heteroaromatic ring system comprises structures of the formulae (Ar-1) to (Ar-13) or the preferred embodiments thereof, where the symbols and indices of the formulae (Ar-1) to (Ar-13) are applicable and, in addition,* represents the bond to the phenanthridine base skeleton.

In a preferred embodiment of the invention, $R^2$ is the same or different at each instance and is selected from the group consisting of H, D, F, $Si(R^3)_3$, CN, a straight-chain alkyl or alkoxy group having 1 to 10 carbon atoms or a branched or cyclic alkyl or alkoxy group having 3 to 10 carbon atoms, each of which may be substituted by one or more $R^3$ radicals, where one or more nonadjacent $CH_2$ groups may be replaced by 0 and where one or more hydrogen atoms may be replaced by D or F, an aromatic or heteroaromatic ring system which has 6 to 60 aromatic ring atoms and may be substituted in each case by one or more $R^3$ radicals, where two or more adjacent $R^2$ substituents may optionally form a mono- or polycyclic aliphatic ring system which may be substituted by one or more $R^3$ radicals.

In a particularly preferred embodiment of the invention, $R^2$ is the same or different at each instance and is selected from the group consisting of H, D, F, a straight-chain alkyl group having 1 to 10 carbon atoms or a branched or cyclic alkyl group having 3 to 10 carbon atoms, each of which may be substituted by one or more $R^3$ radicals, an aromatic or heteroaromatic ring system which has 6 to 60 carbon atoms and may be substituted in each case by one or more $R^3$ radicals, where two or more adjacent $R^2$ substituents may optionally form a mono- or polycyclic aliphatic ring system which may be substituted by one or more $R^3$ radicals.

In a further preferred embodiment, $R^2$ which binds to a carbon bridge in an aromatic or heteroaromatic ring system, as, for example, in the formulae (Ar-5-1), (Ar-5-2), (Ar-5-3), (Ar-5-4), (Ar-6-1), (Ar-6-2), (Ar-6-3), (Ar-6-4), (Ar-8-3-1), (Ar-11-1), (Ar1-5-1), (Ar2-9) or (Ar2-9-2), is the same or different at each instance and is selected from the group consisting of a straight-chain alkyl group having 1 to 10 carbon atoms, a branched or cyclic alkyl group having 3 to 10 carbon atoms or an aromatic ring system having 6 to 30 carbon atoms which is as defined above and which may be substituted by one or more $R^3$ radicals. In this case, the two $R^2$ groups may also form a ring system with one another, which may be aliphatic or, in addition to the definition of $R^2$ given above, may also be aromatic. Ring formation forms a spiro system.

In a further preferred embodiment, $R^2$ which binds to a nitrogen atom is selected from the group consisting of a straight-chain alkyl group having 1 to 10 carbon atoms, a branched or cyclic alkyl group having 3 to 10 carbon atoms or an aromatic ring system having 6 to 30 carbon atoms, especially an aromatic ring system having 6 to 24 carbon atoms which is as defined above and which may be substituted by one or more $R^3$ radicals.

The abovementioned embodiments may be combined with one another as desired. More particularly, it is preferable to combine the preferred embodiments detailed above with one another.

In a preferred embodiment of the invention, the compound is a compound of the formula (5) where K is a single bond and, together with $Ar^2$—N—$Ar^1$, forms a carbazole group of one of the formulae (Ar-5-9), (Ar-5-10), (Ar-5-11), (Ar-5-12), where N—$R^2$ is N—$Ar^1$.

In a further preferred embodiment of the invention, the compound is a compound of the formula (3). Preferably, $Ar^1$ is selected from the formulae (Ar-1) to (Ar-13) and $Ar^2$, if present, is selected from one of the formulae (Ar2-1) to (Ar2-14); more preferably, $Ar^1$ is selected from the formulae (Ar-1-1) to (Ar-13-1) and $Ar^2$, if present, is selected from one of the formulae (Ar2-1-1) to (Ar2-13-3).

Examples of preferred compounds of the above-detailed embodiments or compounds as usable with preference in organic electronic devices are the following compounds:

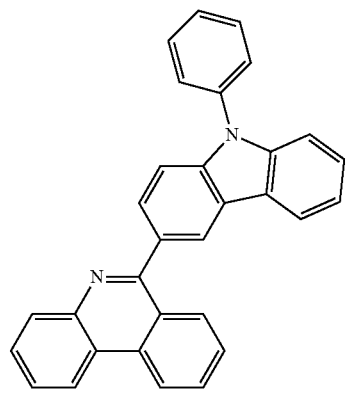

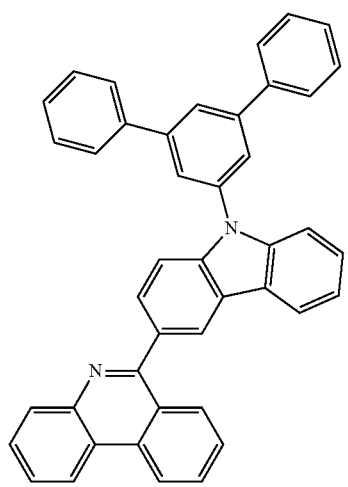
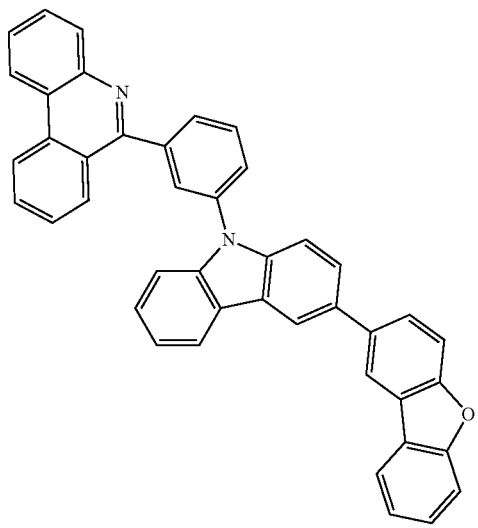
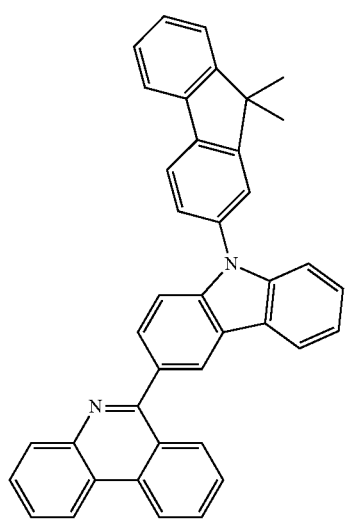
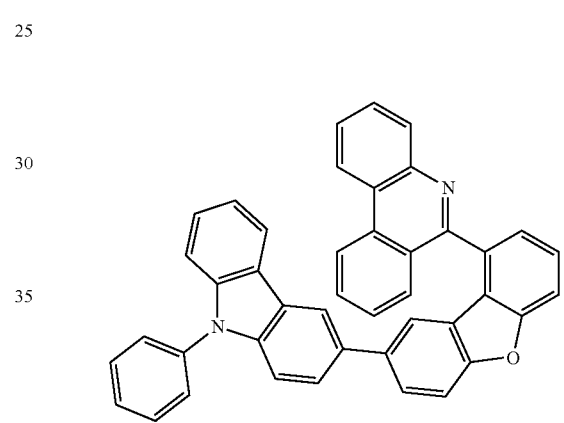
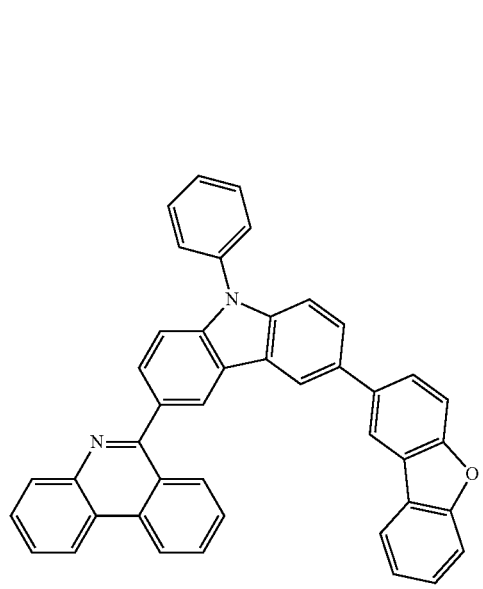
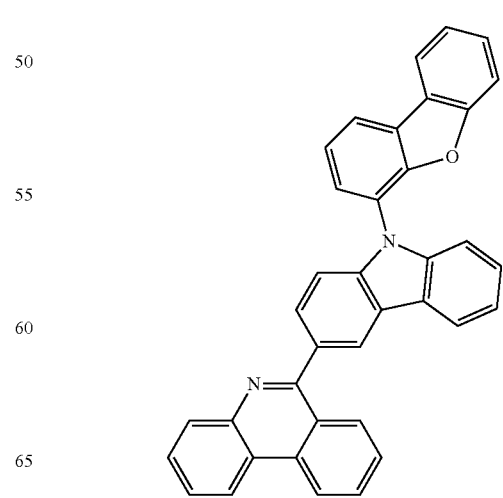

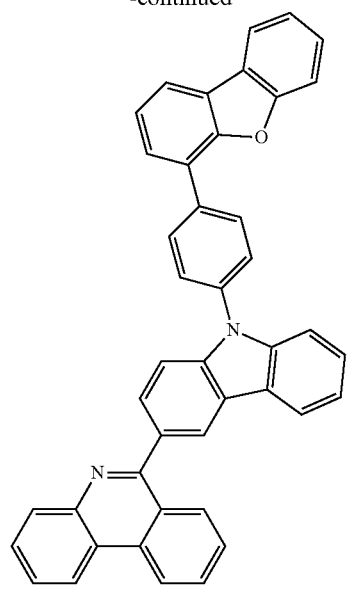
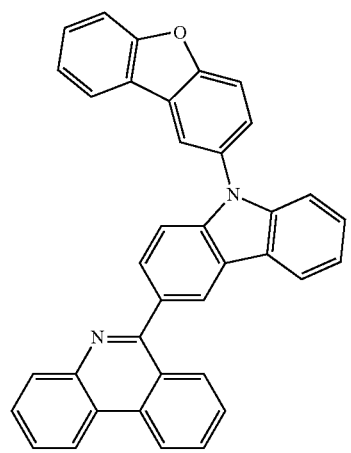
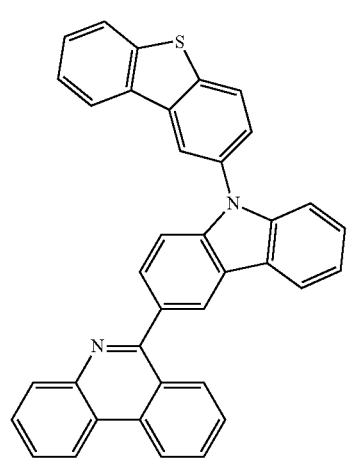
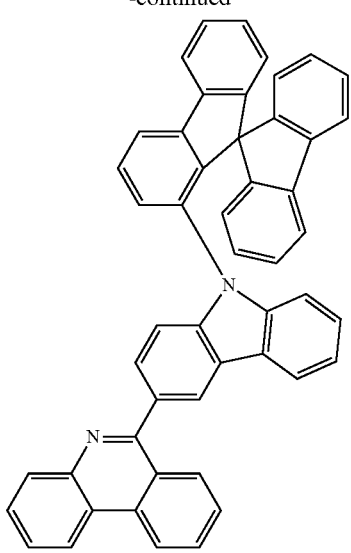
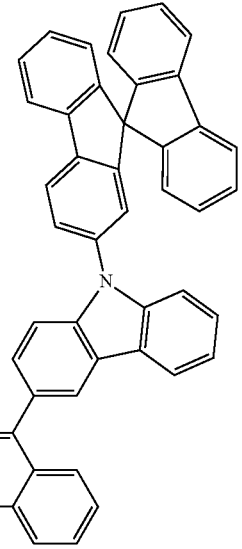
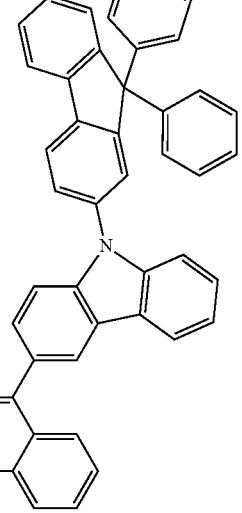

-continued
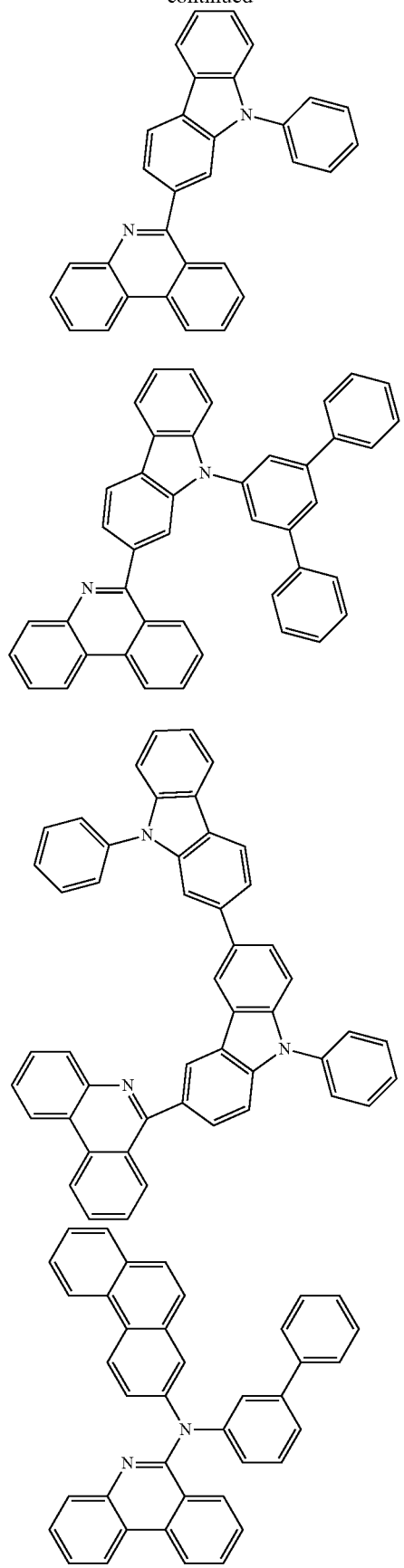
-continued
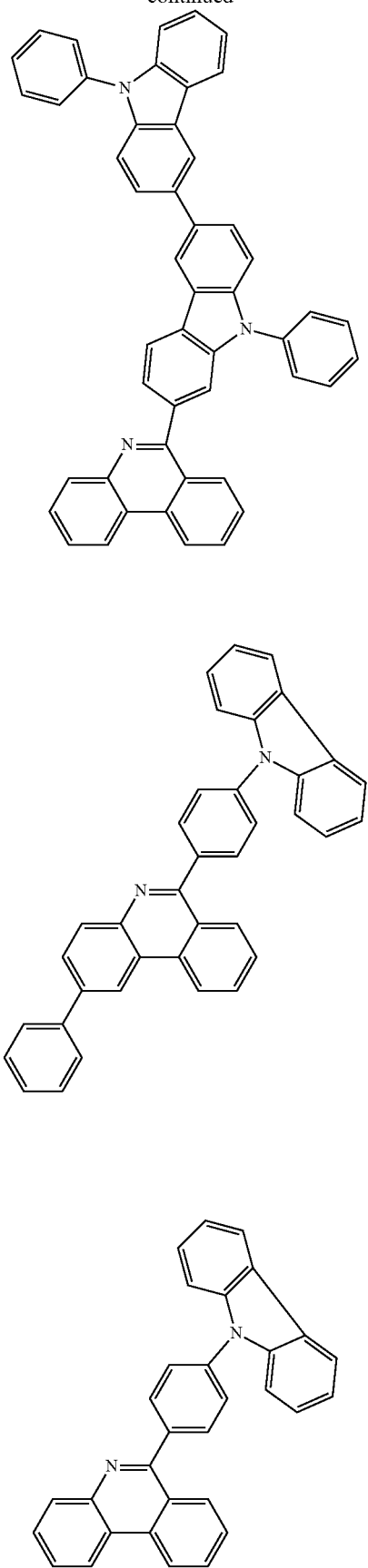

51
-continued
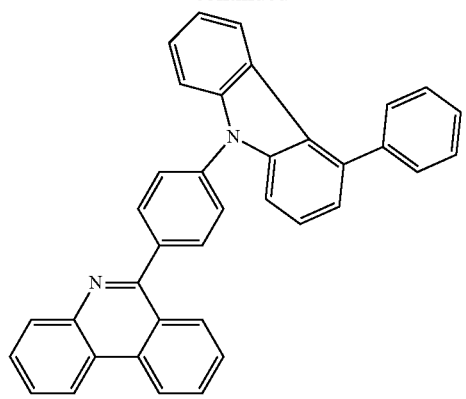
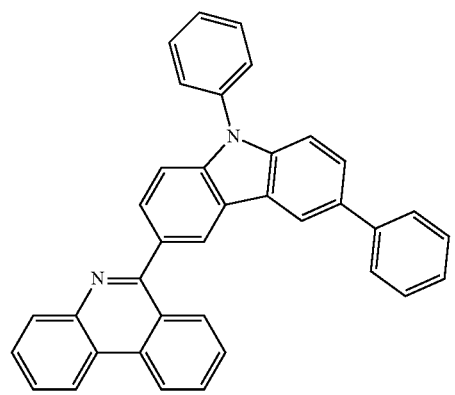
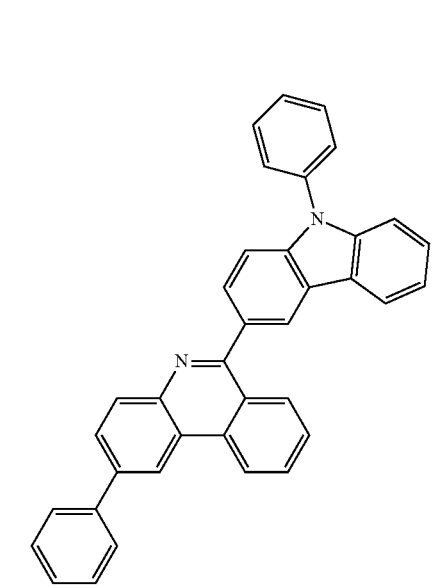
52
-continued
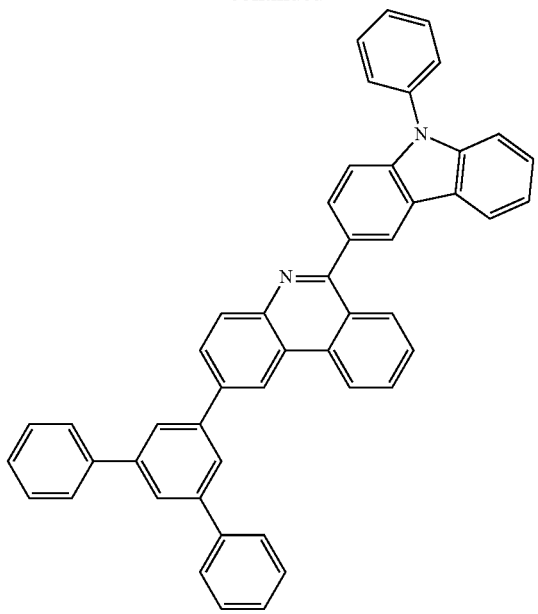
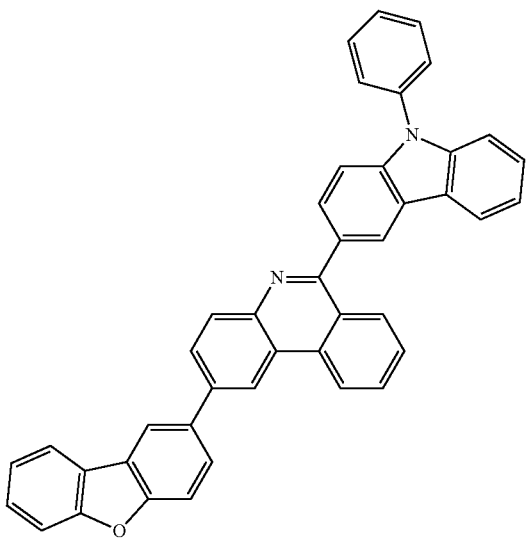

53
-continued
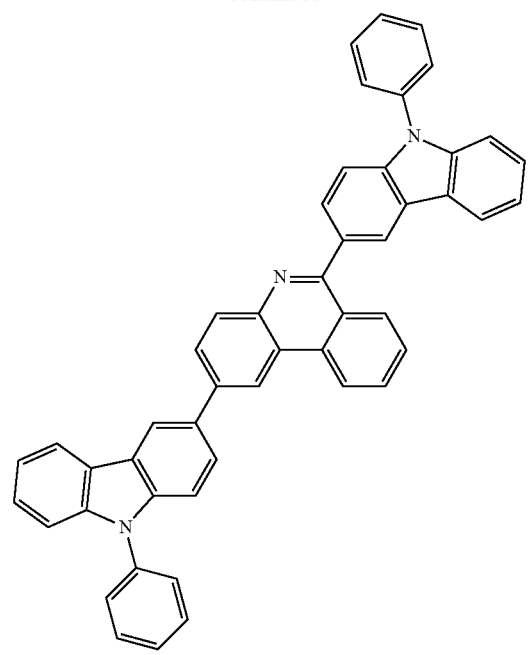
54
-continued
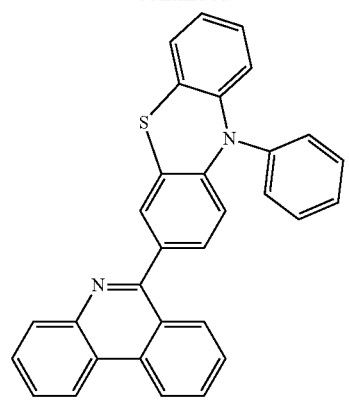
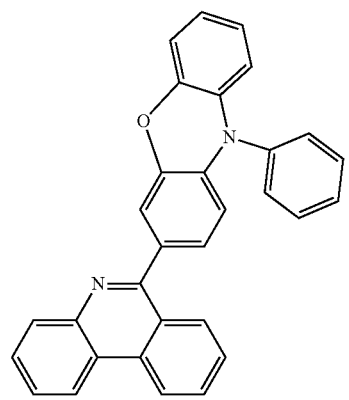
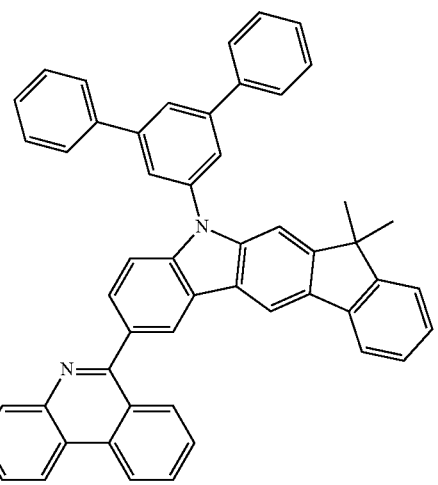

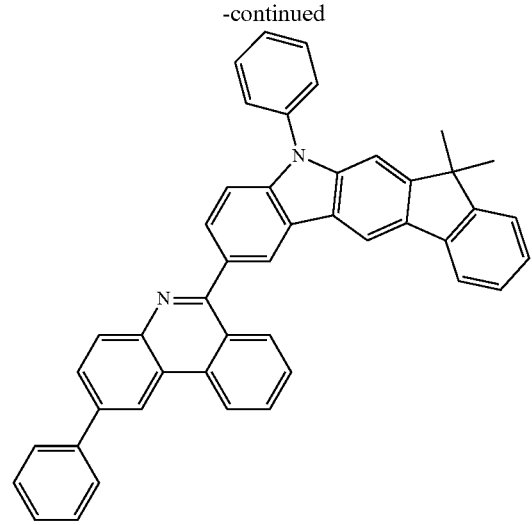
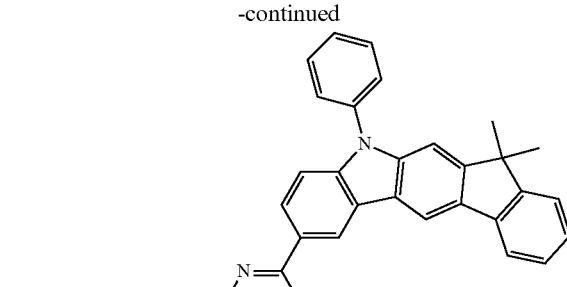
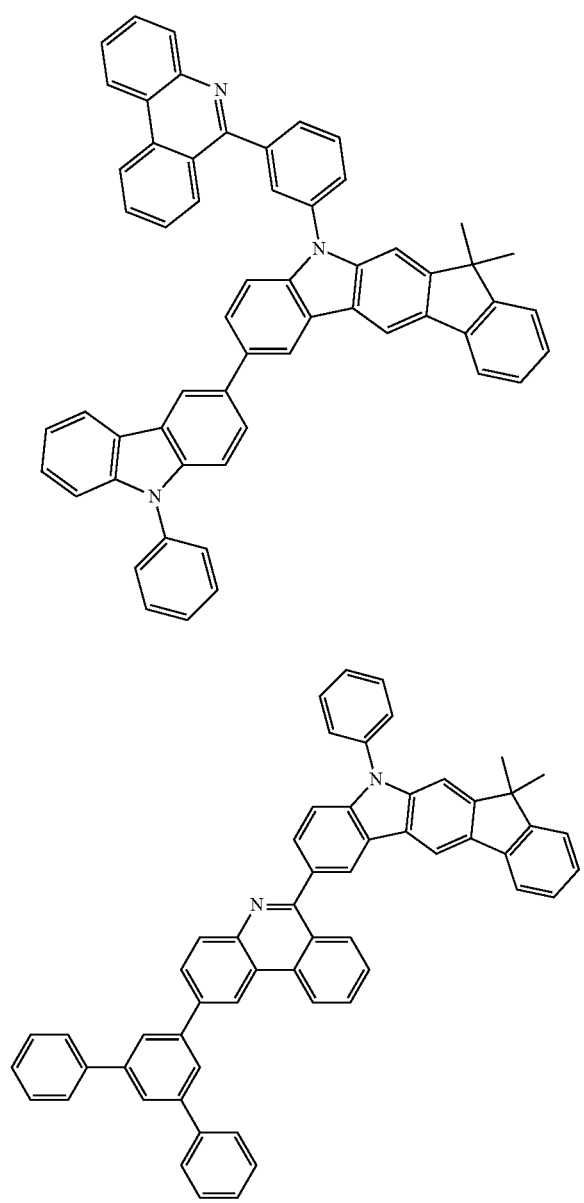
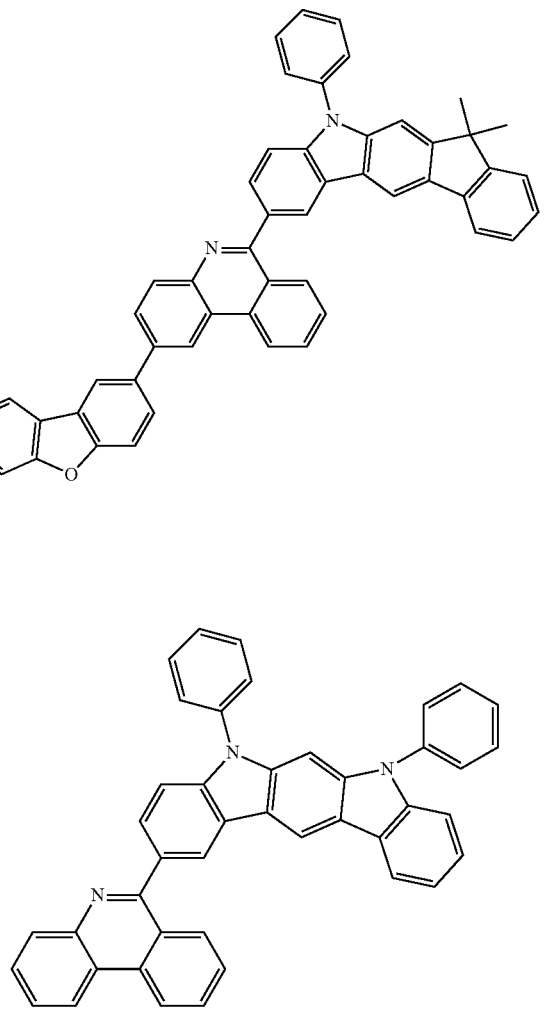

-continued
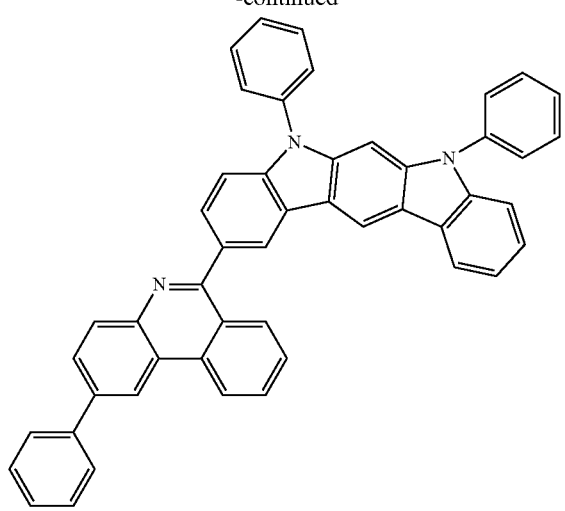
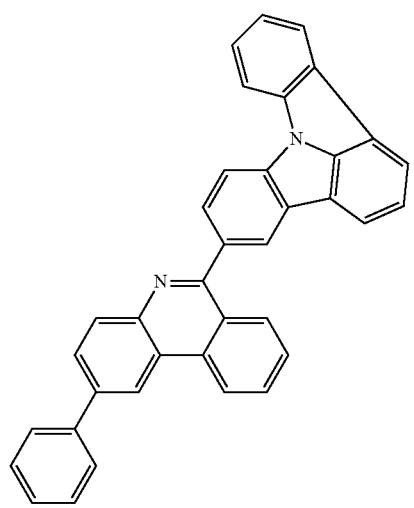
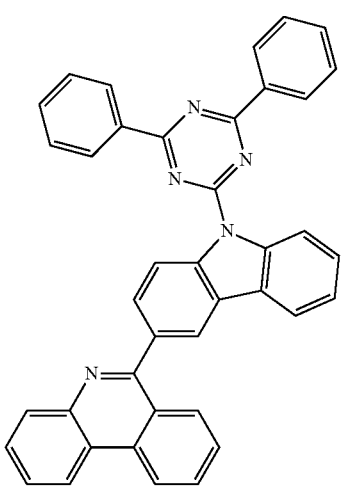
-continued
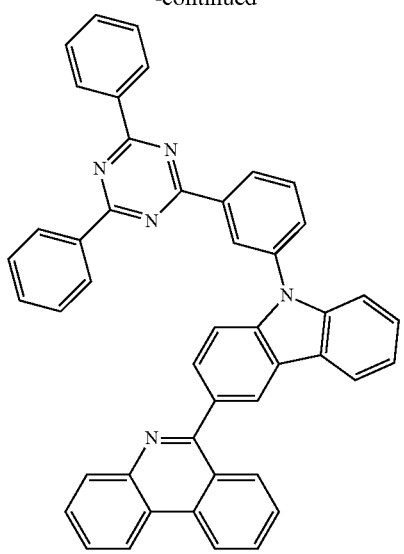
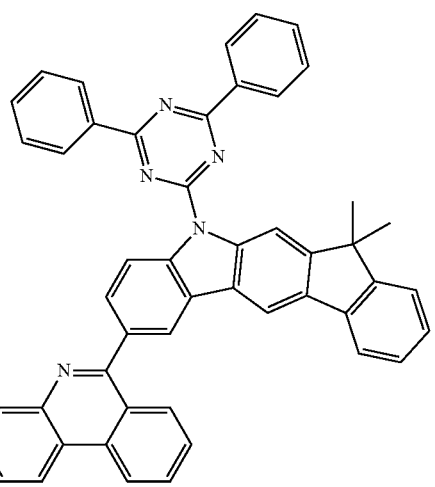
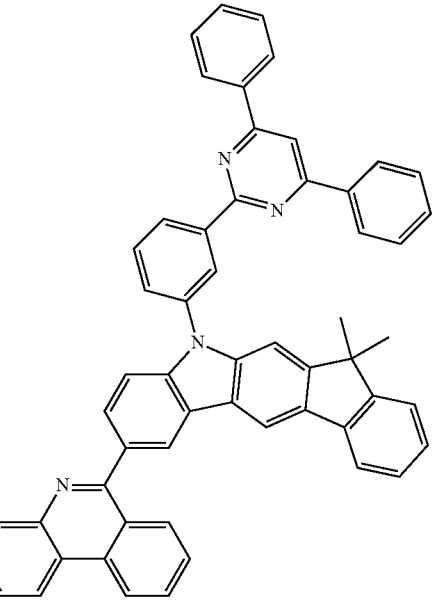

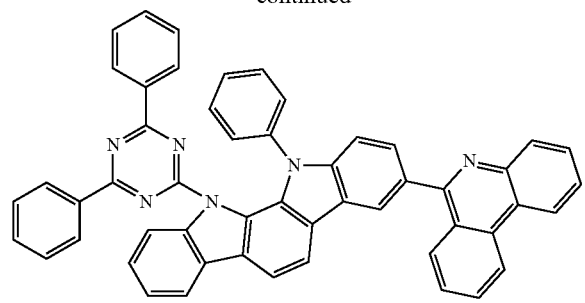
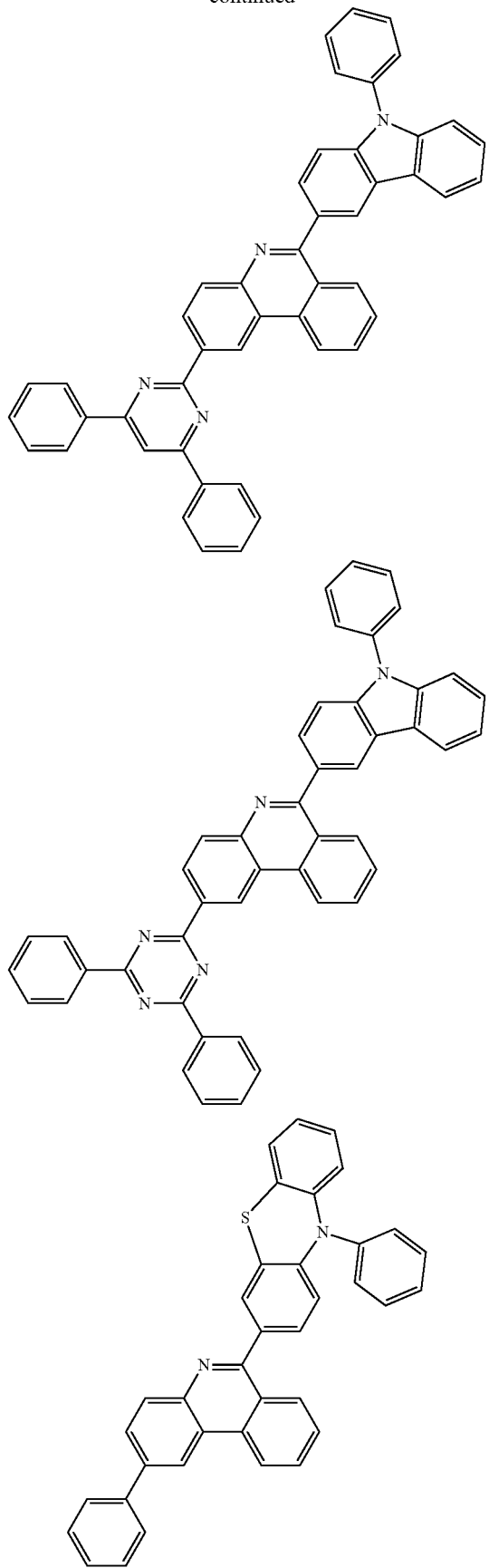

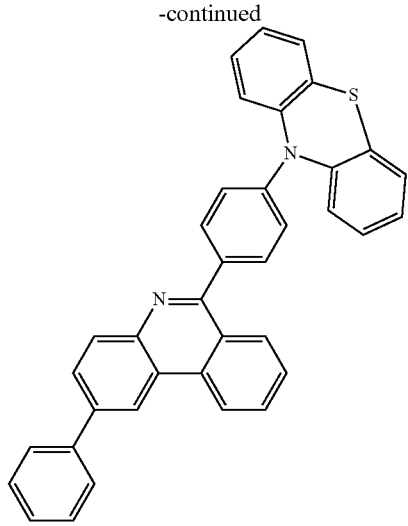
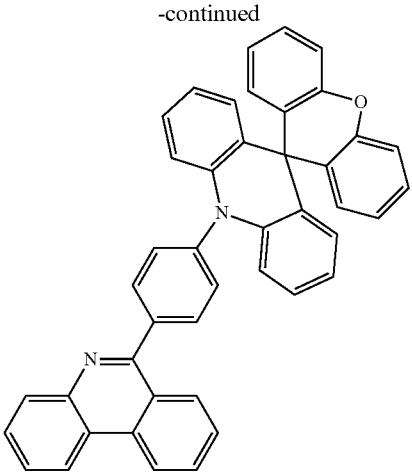
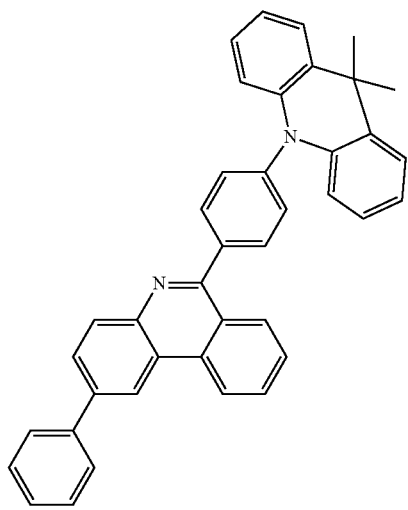
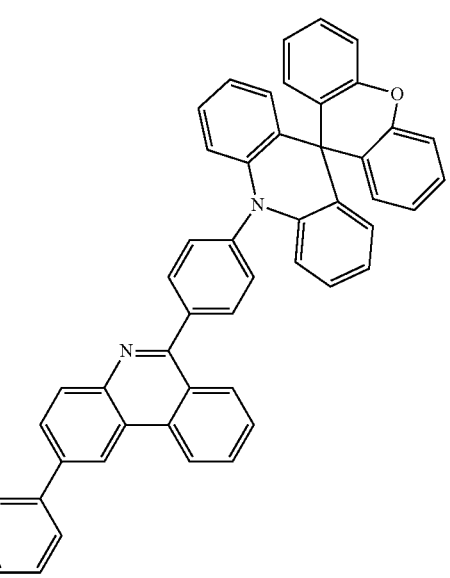
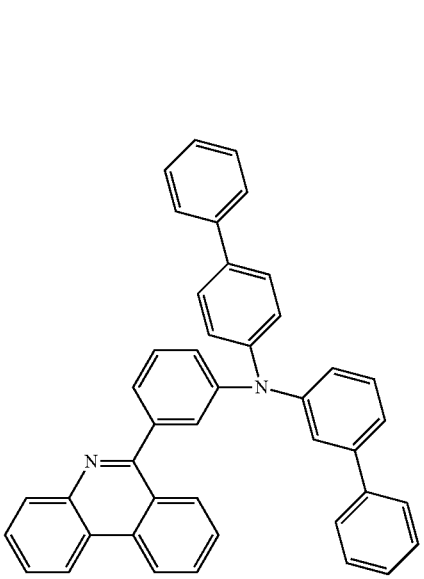

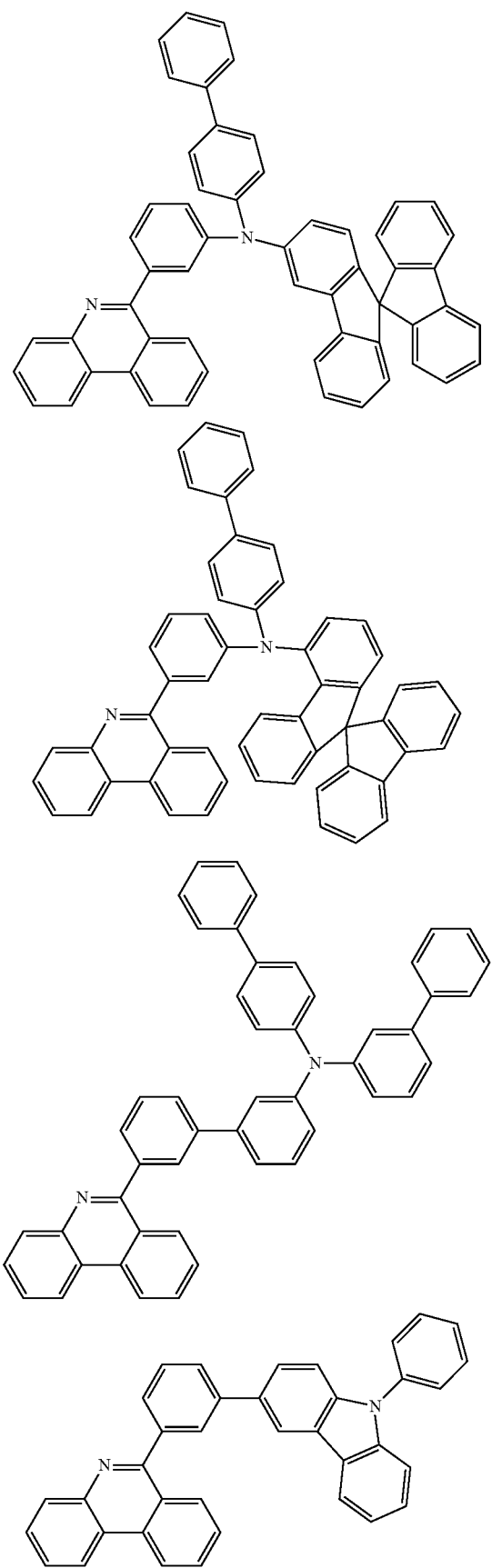
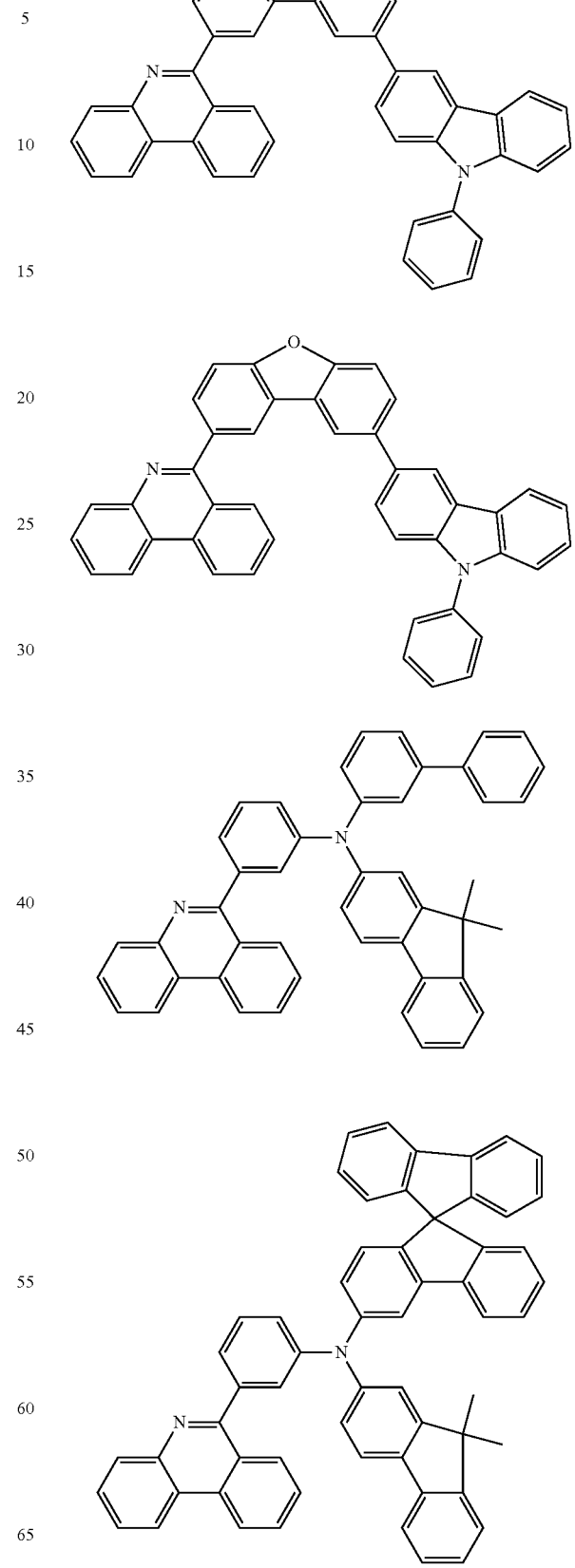

-continued
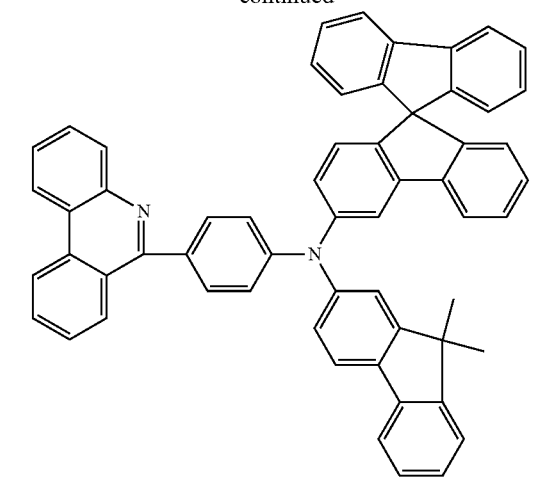
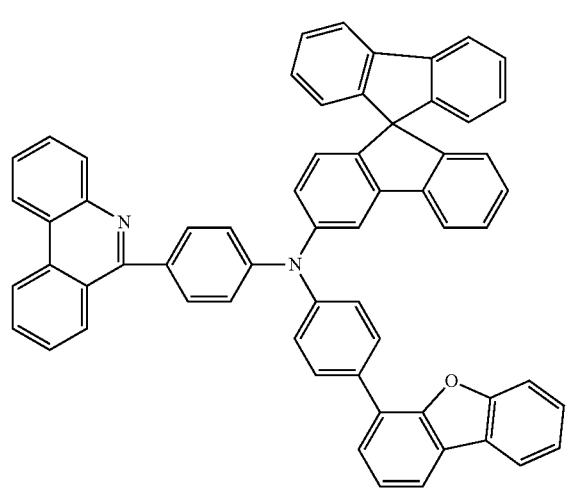
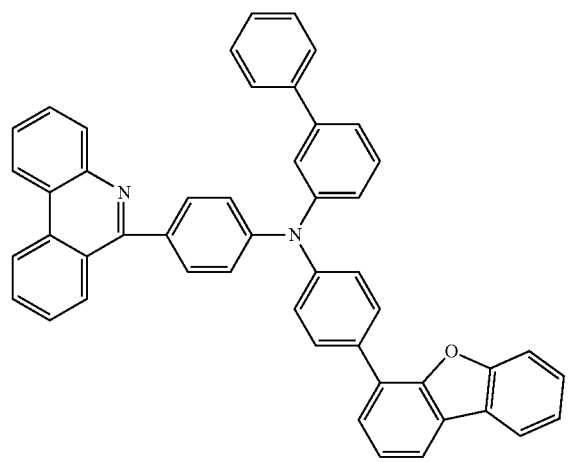
-continued
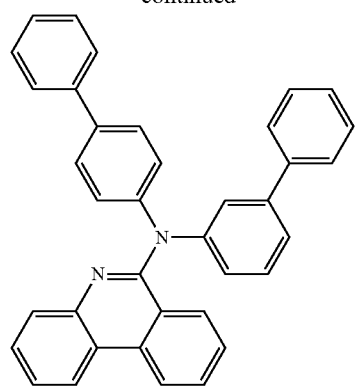
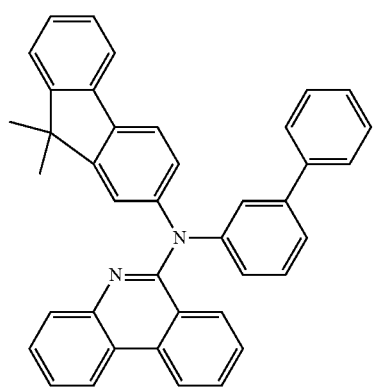
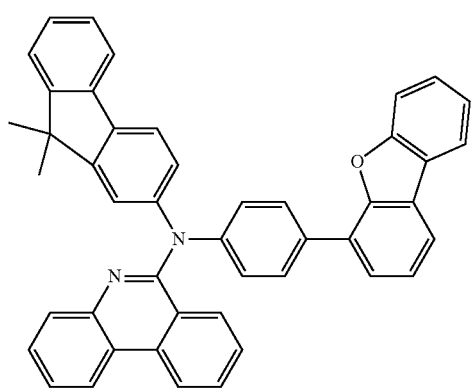
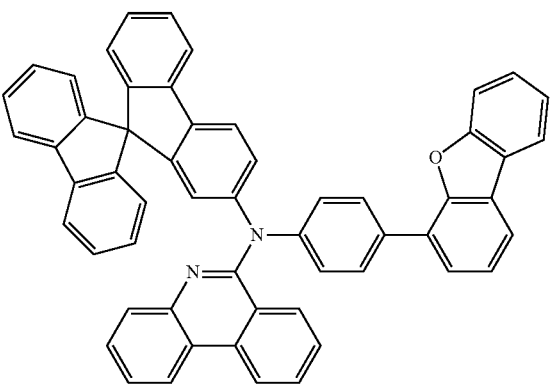

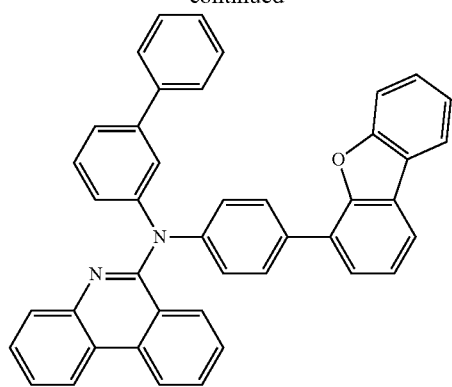
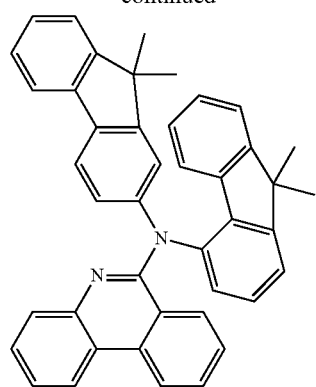
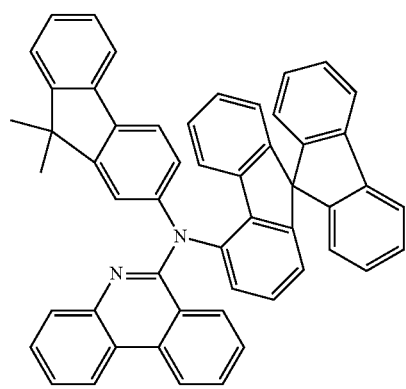
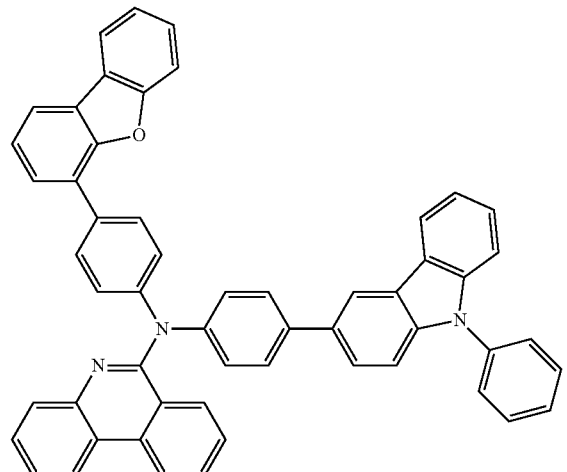
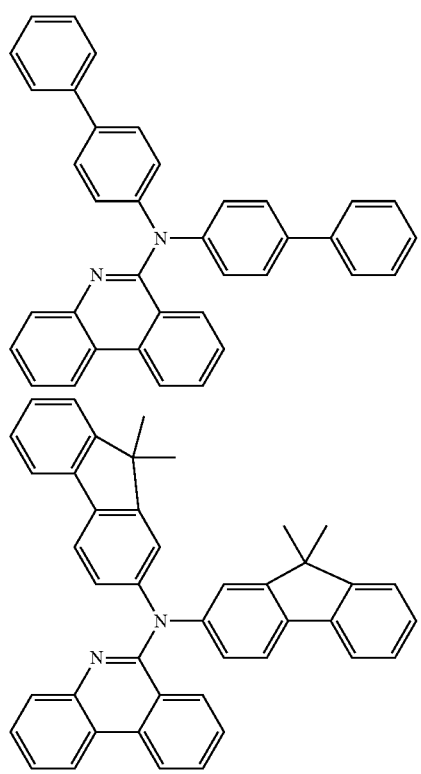
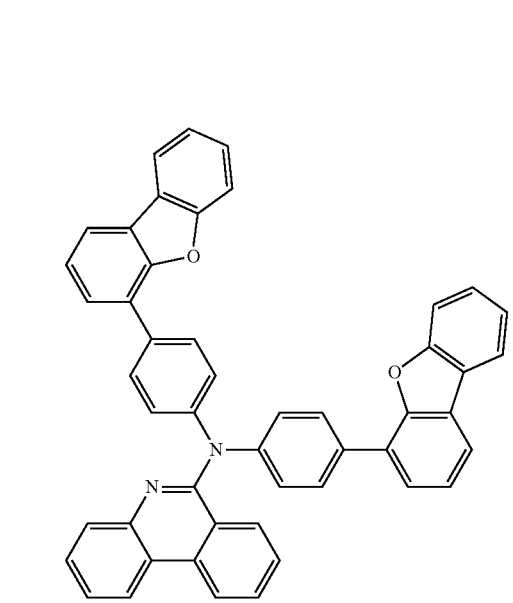

-continued
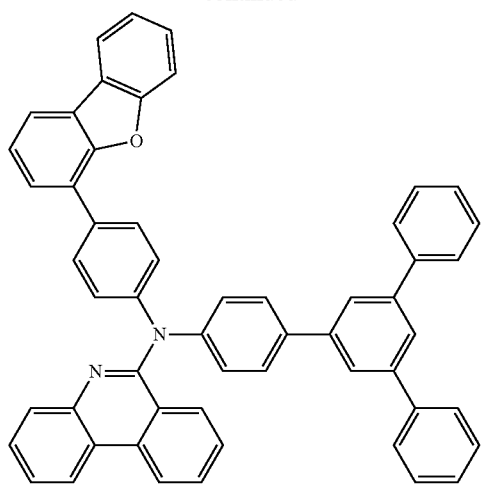
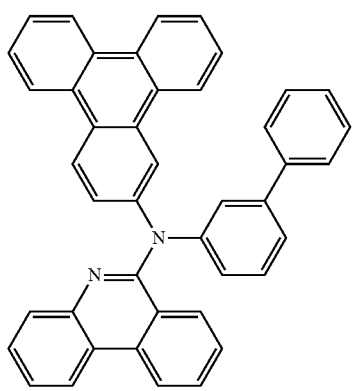
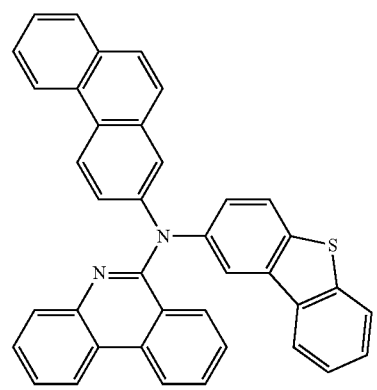
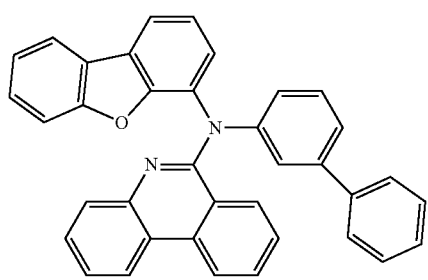
-continued
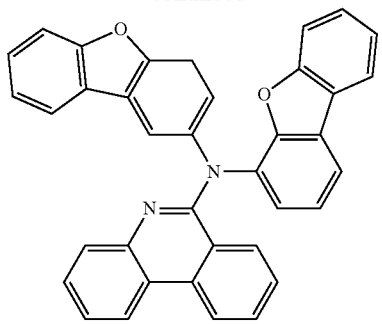
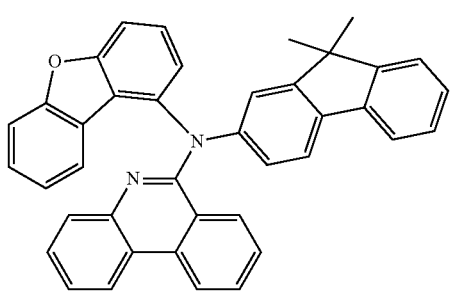
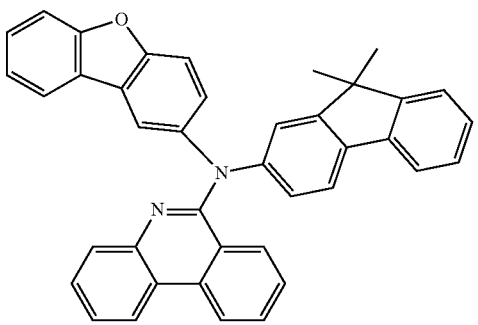
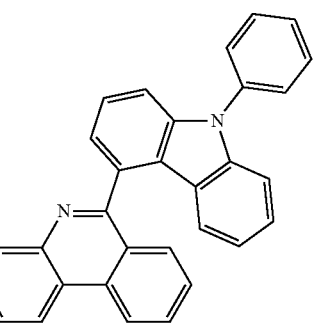
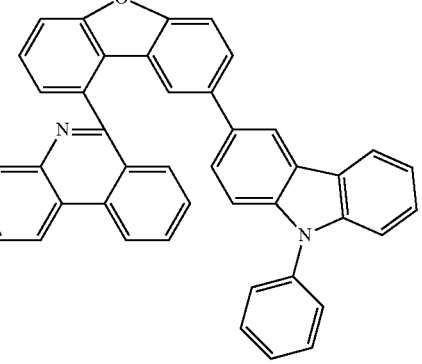

71
-continued
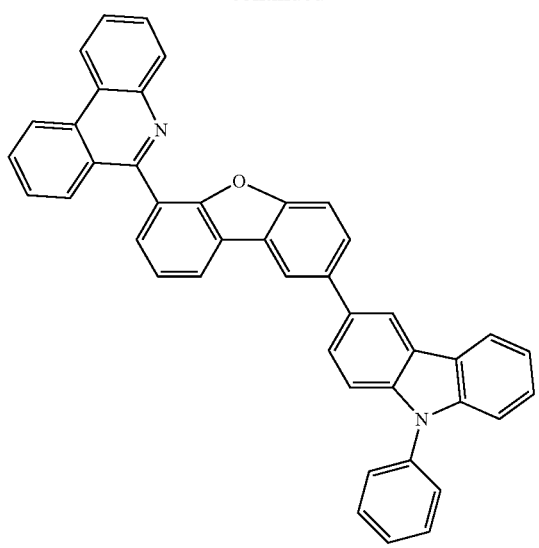
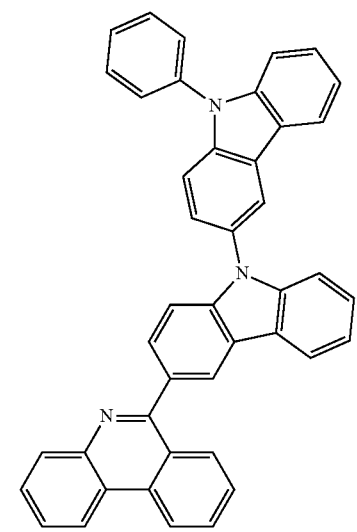
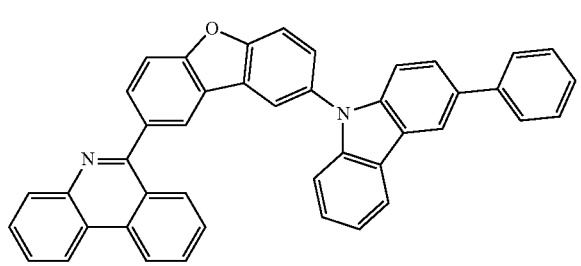
72
-continued
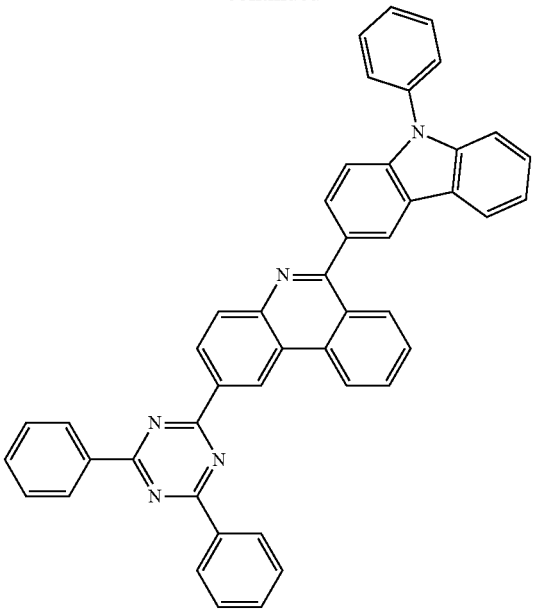
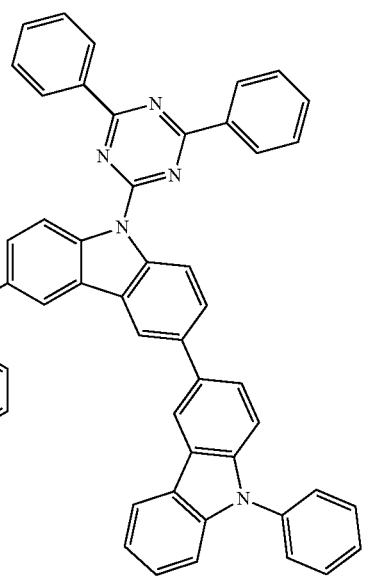

73
-continued
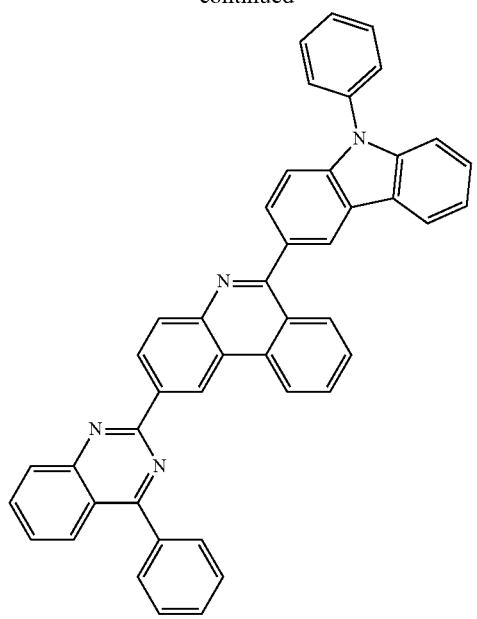
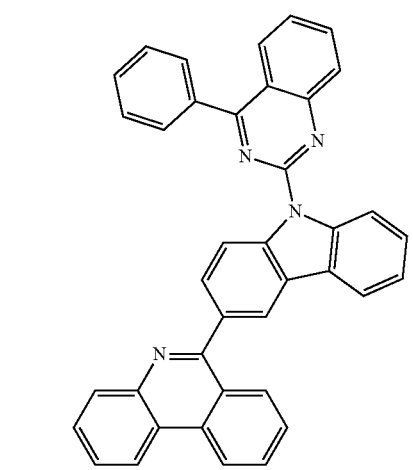
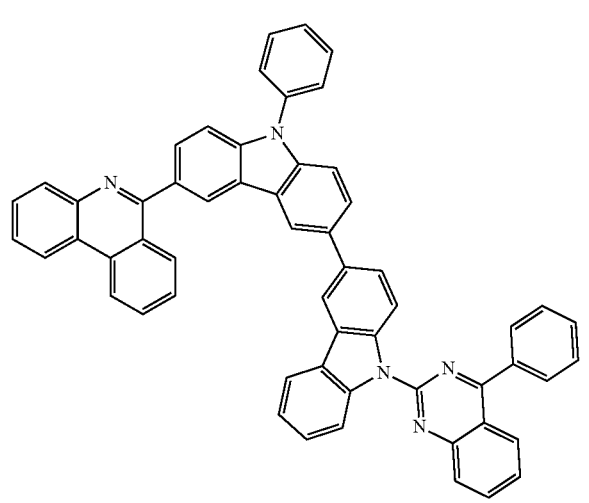
74
-continued
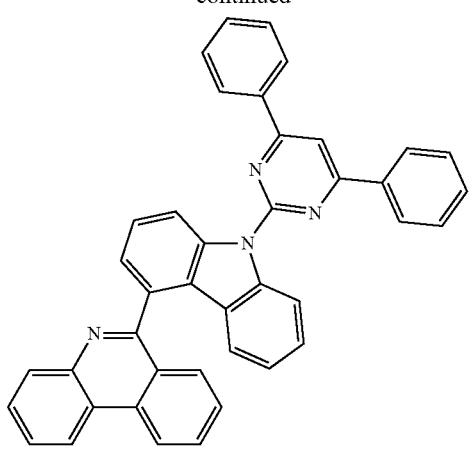
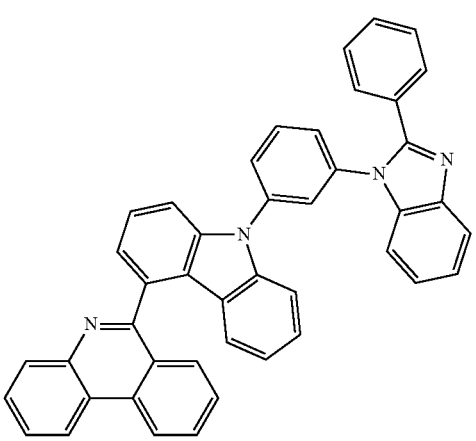
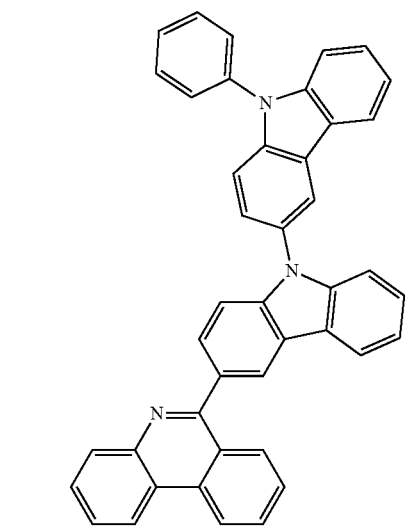

75
-continued
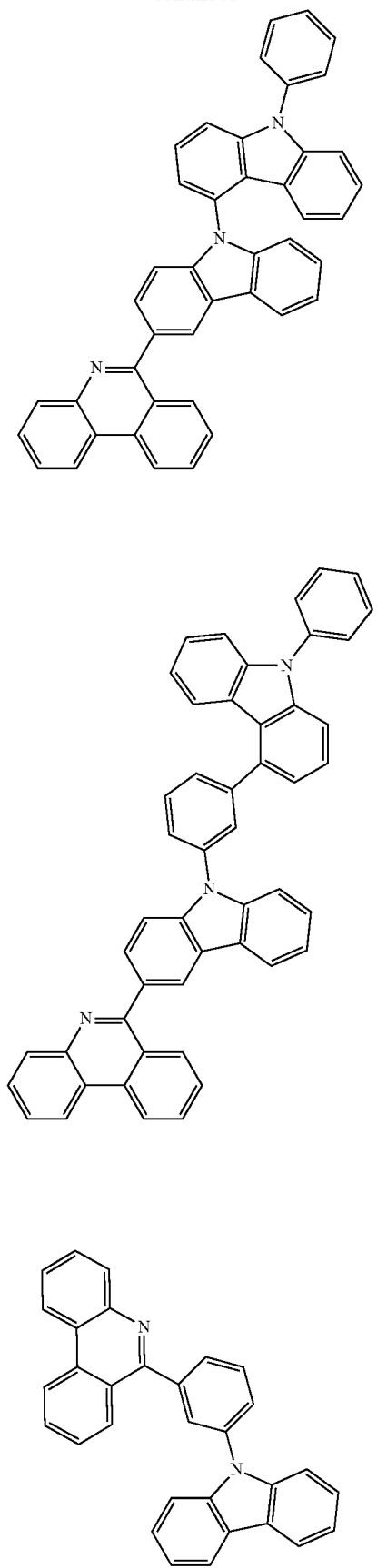
76
-continued
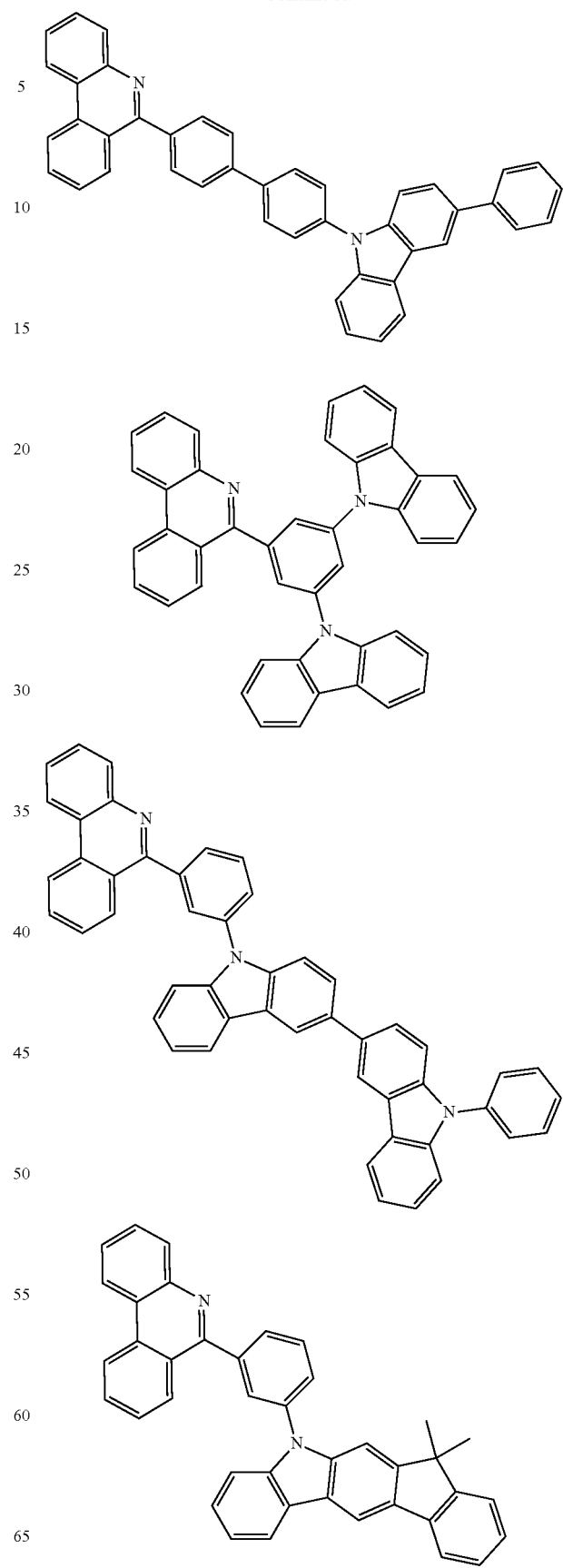

77
-continued
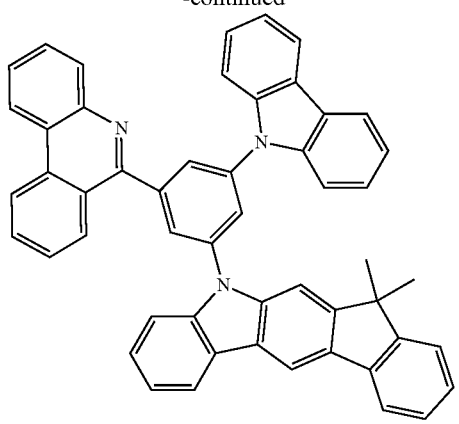
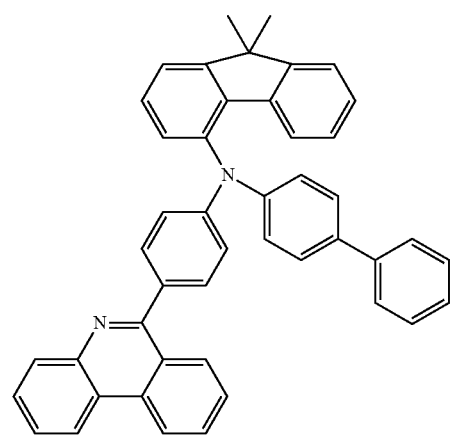
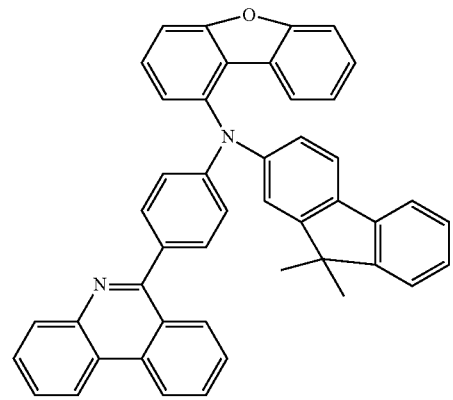
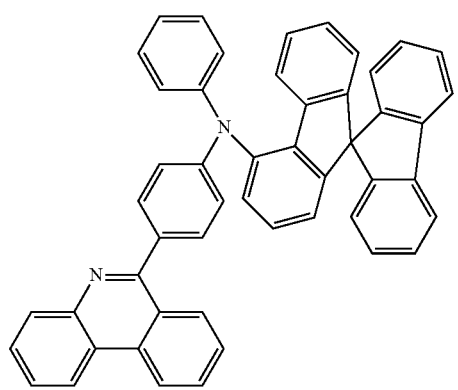
78
-continued
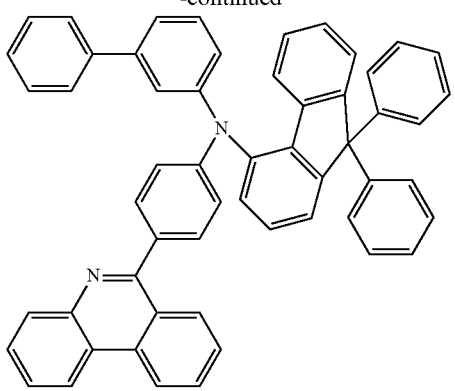
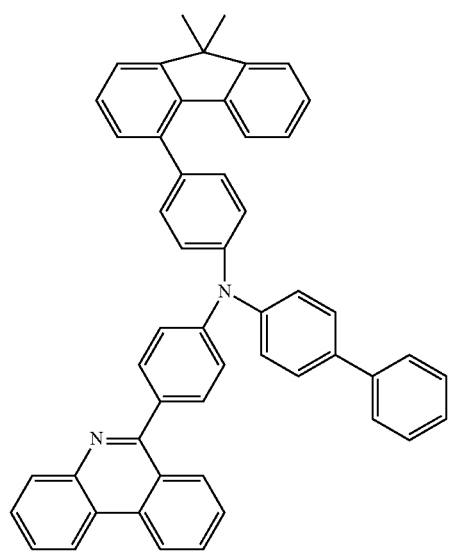

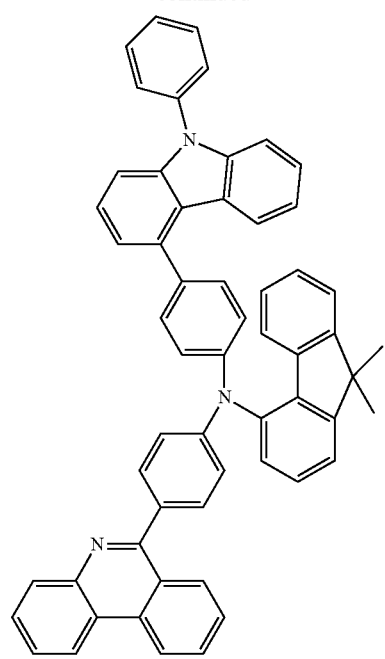
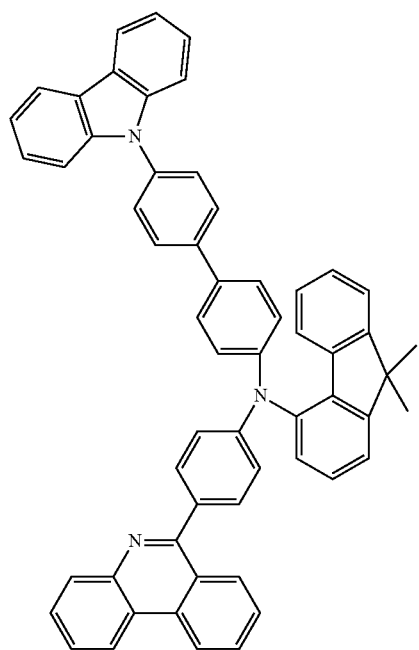
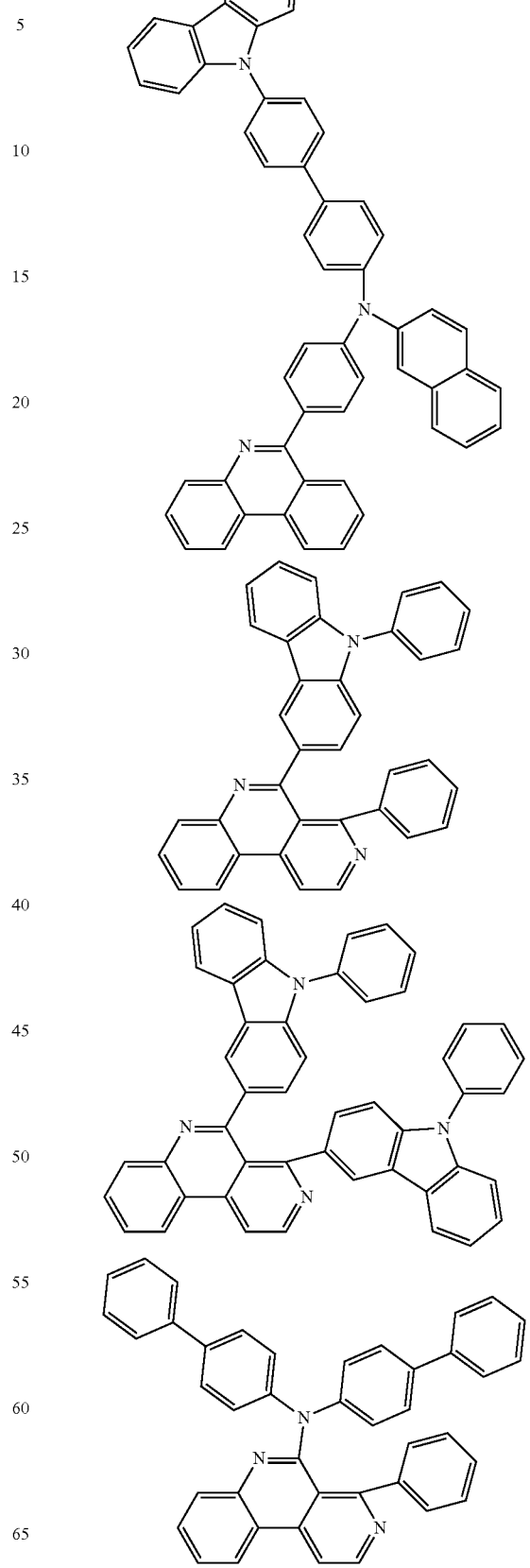

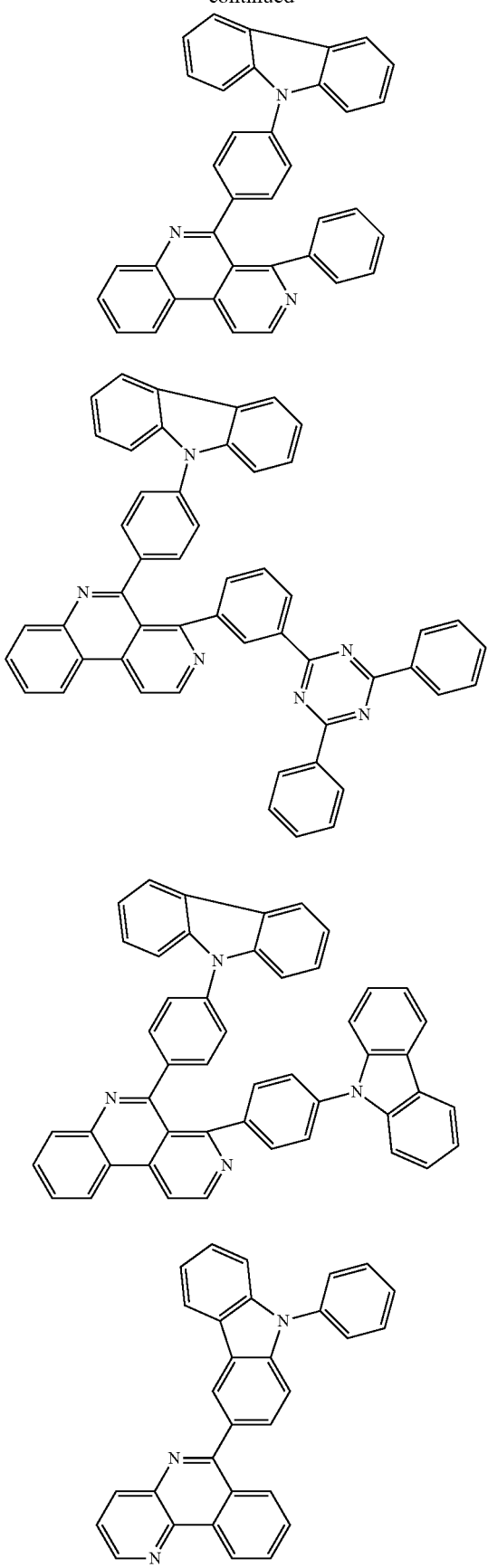

-continued

The inventive compounds can be prepared by synthesis steps known to those skilled in the art, for example bromination, Suzuki coupling, Ullmann coupling, Hartwig-Buchwald coupling, etc.

The phenanthridine base skeleton is prepared, for example, proceeding from fluoren-9-one with subsequent formation of an amide by a Beckmann rearrangement. The keto group of the amide obtained can be converted to a leaving group, for example a halide. By one or more coupling reactions, it is then possible to obtain a compound of the formula (1).

The present invention therefore further provides a process for preparing a compound of formula (1) wherein the compound of the formula (1) is formed by one or more coupling reactions, rearrangements and/or cyclizations.

The synthesis methods shown above are of illustrative character and can be modified in a suitable manner by the person skilled in the art in the field of organic synthesis if this is advantageous for the synthesis of particular embodiments of inventive compounds.

The above-described inventive compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C=C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (1), wherein the bond(s) to the polymer, oligomer or dendrimer, may be localized at any free positions in formula (1). According to the linkage of the inventive compound, the compound is part of a side chain of the oligomer or polymer or part of the main chain.

An oligomer in the context of this invention is understood to mean a compound formed from at least three monomer units. A polymer in the context of this invention is understood to mean a compound formed from at least ten monomer units.

The inventive polymers, oligomers and dendrimers may be conjugated, partly conjugated or nonconjugated. The inventive oligomers or polymers may be linear, branched or dendritic.

In the structures having linear linkage, the units of formula (1) may be joined directly to one another, or they may be joined to one another via a bivalent group, for example via a substituted or unsubstituted alkylene group, via a heteroatom or via a bivalent aromatic or heteroaromatic group.

In branched and dendritic structures, it is possible, for example, for 3, 5 or more units of formula (1) to be joined by a trivalent or higher-valency group, for example via a trivalent or higher-valency aromatic or heteroaromatic group, to give a branched or dendritic oligomer or polymer.

For the repeat units of formula (1) in oligomers, dendrimers and polymers, the same preferences apply as described above for the inventive compounds.

For preparation of the oligomers or polymers, the monomers of the invention are homopolymerized or copolymerized with further monomers.

Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The inventive polymers, oligomers and dendrimers have advantageous properties, especially high lifetimes, high efficiencies and good color coordinates.

The inventive polymers and oligomers are generally prepared by polymerization of one or more monomer types, of which at least one monomer leads to repeat units of the formula (1) in the polymer. Suitable polymerization reactions are known to those skilled in the art and are described in the literature. Particularly suitable and preferred polymerization reactions which lead to C—C and C—N bonds are as follows:

(A) SUZUKI polymerization
(B) YAMAMOTO polymerization
(C) STILLE polymerization and
(D) HARTWIG-BUCHWALD polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

The present invention thus also provides a process for preparing the inventive polymers, oligomers and dendrimers, which is characterized in that they are prepared by polymerization according to SUZUKI, polymerization according to YAMAMOTO, polymerization according to STILLE or polymerization according to HARTWIG-BUCHWALD. The inventive dendrimers can be prepared by processes known to those skilled in the art or in analogy thereto. Suitable processes are described in the literature, for example in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the inventive compounds from the liquid phase, for example by spin-coating or by printing methods, formulations of the inventive compounds are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (-)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (1) or at least one polymer, oligomer or dendrimer containing at least one unit of formula (1) and at least one solvent, preferably an organic solvent. The way in which such solutions can be prepared is known to those skilled in the art and is described, for example, in WO 2002/072714, WO 2003/019694 and the literature cited therein.

The present invention further provides mixtures comprising at least one inventive compound and at least one further compound. The further compound may, for example, be a fluorescent or phosphorescent dopant when the inventive compound is used as matrix material, especially a phosphorescent dopant. Suitable dopants are detailed below in connection with the organic electroluminescent devices and are also preferred for the inventive mixtures.

The inventive compounds and mixtures are suitable for use in an electronic device. An electronic device is understood to mean a device containing at least one layer containing at least one organic compound. This component may also contain inorganic materials or else layers formed entirely from inorganic materials.

The present invention therefore further provides for the use of the inventive compounds or mixtures in an electronic device, especially in an organic electroluminescent device.

The present invention still further provides an electronic device comprising at least one of the above-detailed inventive compounds or mixtures. In this case, the preferences detailed above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), preferably consisting of organic electroluminescent devices (OLEDs, PLEDs), especially phosphorescent OLEDs.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily each of these layers need be present. In this case, it is possible for the organic electroluminescent device to contain an emitting layer, or for it to contain a plurality of emitting layers. If a plurality of emission layers are present, these preferably have several emission maxima between 380 nm and 750 mm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction see, for example, WO 2005/011013). These may be fluorescent or phosphorescent emission layers or else hybrid systems in which fluorescent and phosphorescent emission layers are combined with one another.

The inventive compound according to the above-detailed embodiments may be used in different layers, according to the exact structure. Preference is given to an organic electroluminescent device containing a compound of formula (1) or according to the preferred embodiments as matrix material for fluorescent or phosphorescent emitters, especially for phosphorescent emitters, and/or in an electron transport layer and/or in an electron-blocking or exciton-blocking layer and/or in a hole transport layer, according to the exact substitution, more preferably as matrix material for fluorescent or phosphorescent emitters, especially for phosphorescent emitters, and/or in an electron transport layer and/or in a hole transport layer. In this context, the above-detailed preferred embodiments also apply to the use of the materials in organic electronic devices.

In a preferred embodiment of the invention, the compound of formula (1) or according to the preferred embodiments is used as matrix material for a fluorescent or phosphorescent compound, especially for a phosphorescent compound, in an emitting layer. In this case, the organic electroluminescent device may contain an emitting layer, or it may contain a plurality of emitting layers, where at least one emitting layer contains at least one inventive compound as matrix material.

A further preferred embodiment of the present invention is the use of the compound of formula (1) or according to the preferred embodiments as matrix material for a phosphorescent emitter in combination with a further matrix material. Particularly suitable matrix materials which can be used in combination with the compounds of formula (1) or according to the preferred embodiments are aromatic ketones, aromatic phosphine oxides or aromatic sulphoxides or sulphones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951. It is likewise possible for a further phosphorescent emitter which emits at a shorter wavelength than the actual emitter to be present as co-host in the mixture.

The mixture of the compound of formula (1) or according to the preferred embodiments and the emitting compound contains between 99% and 1% by volume, preferably between 98% and 10% by volume, more preferably between 97% and 60% by volume and especially between 95% and 80% by volume of the compound of formula (1) or according to the preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

The term "phosphorescent dopants (emitters)" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preferred phosphorescent dopants are compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices. It is also possible for the person skilled in the art, without exercising inventive skill, to use further phosphorescent complexes in combination with the inventive compounds in OLEDs.

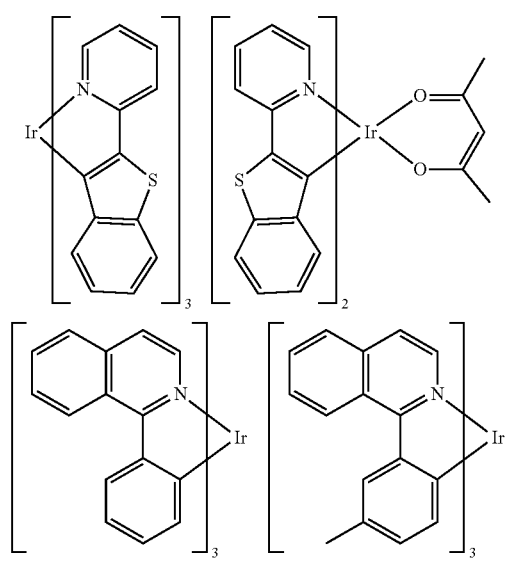

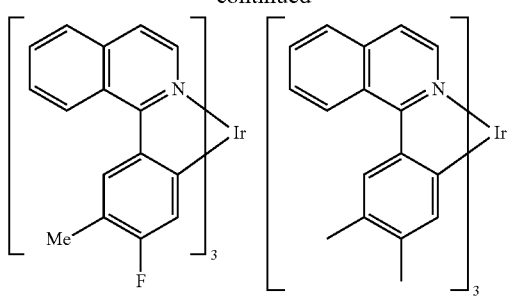
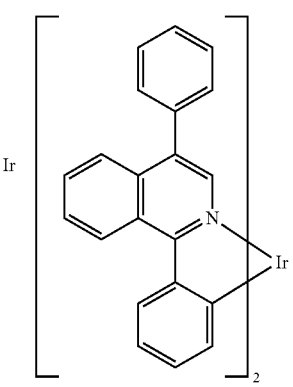
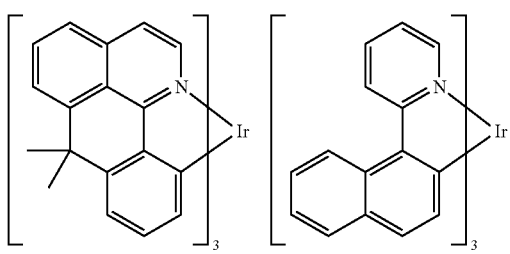
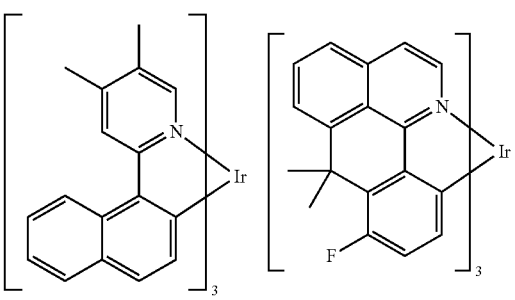
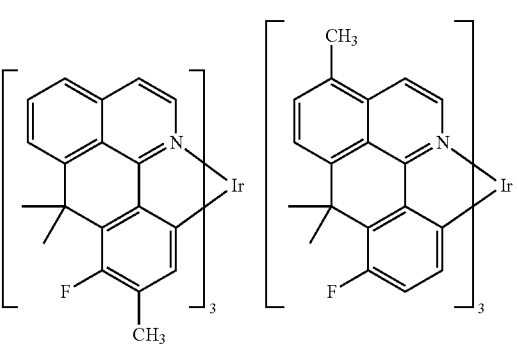
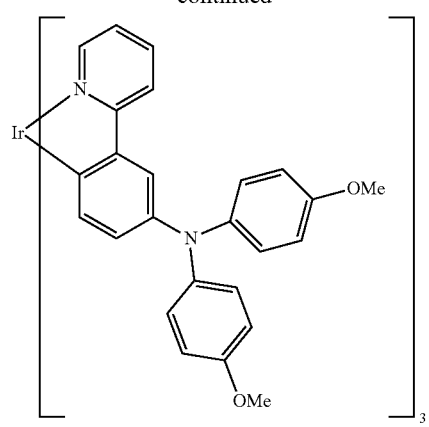
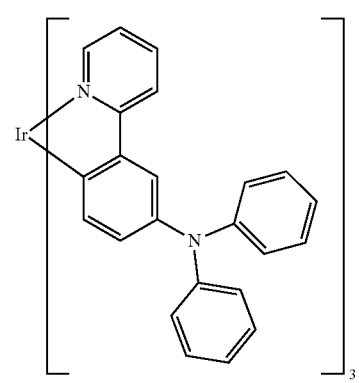
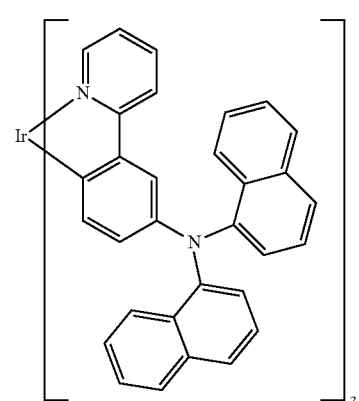
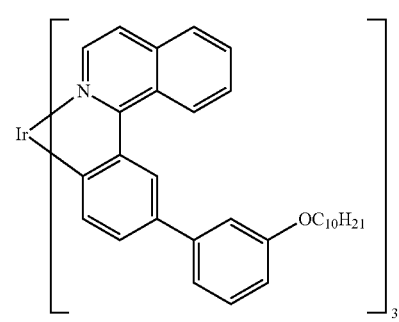

91
-continued
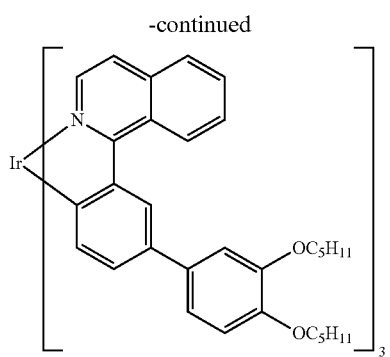
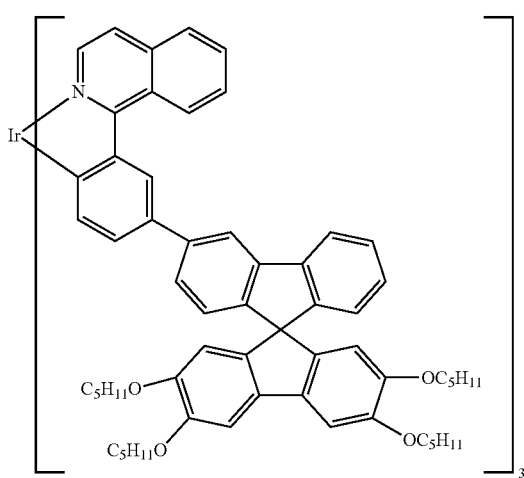
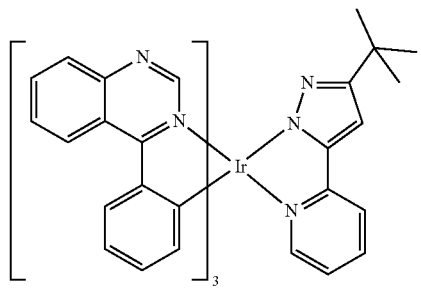
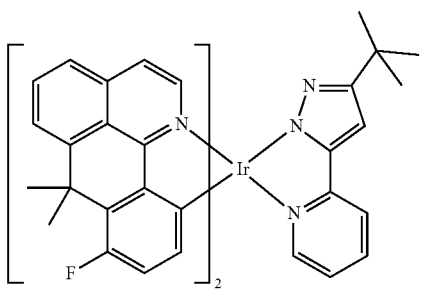
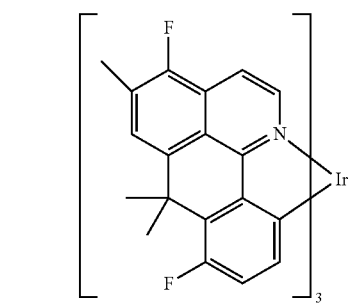
92
-continued
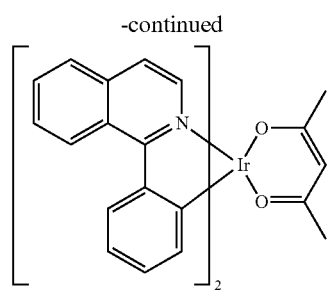
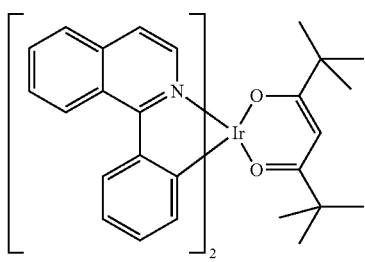
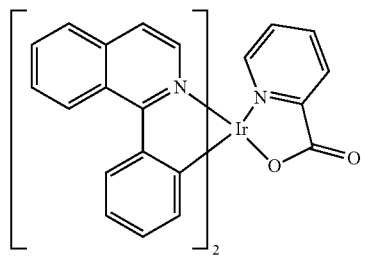
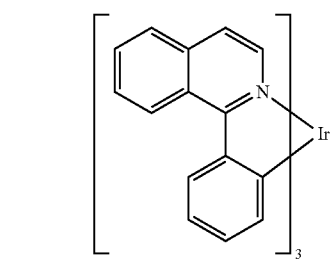
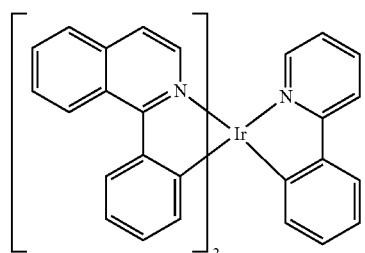
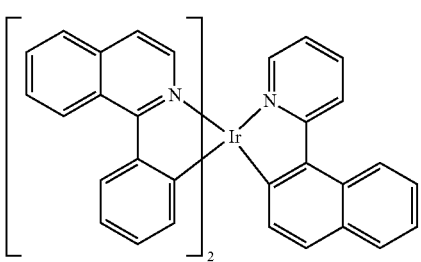

-continued
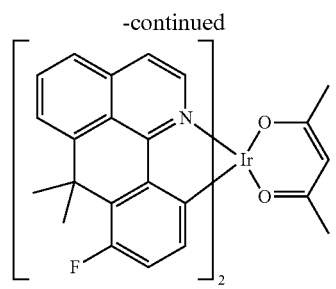
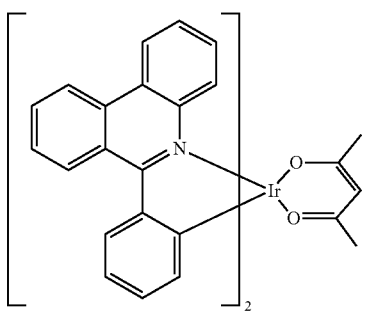
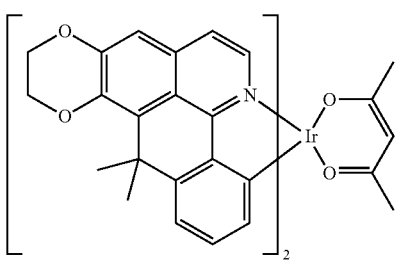
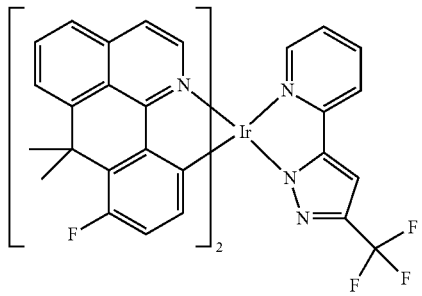
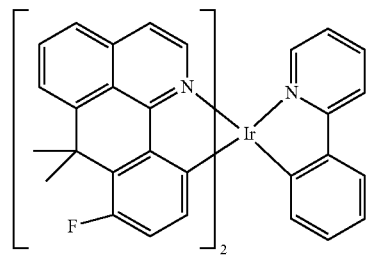
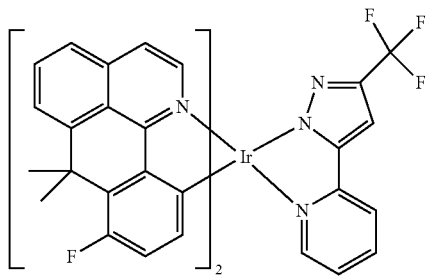
-continued
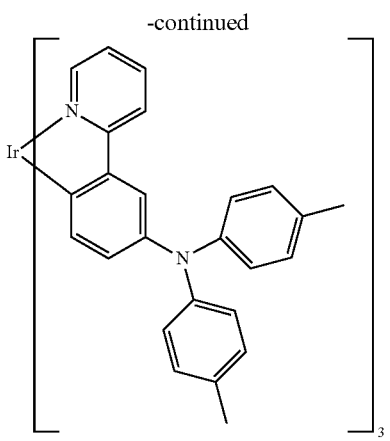
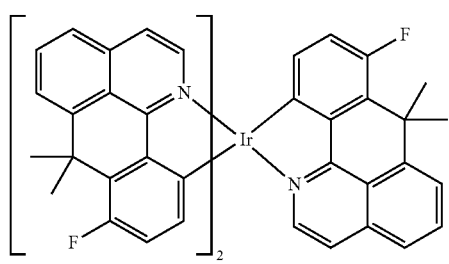
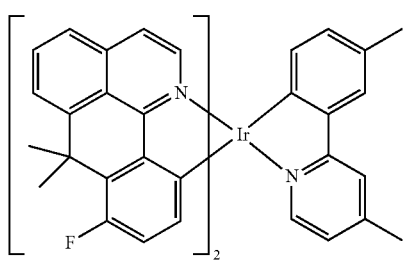
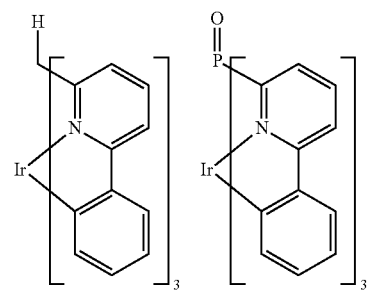
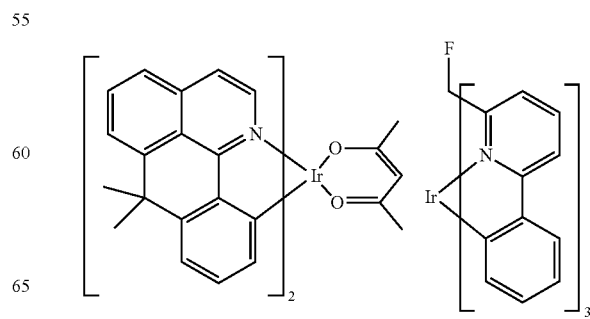

-continued
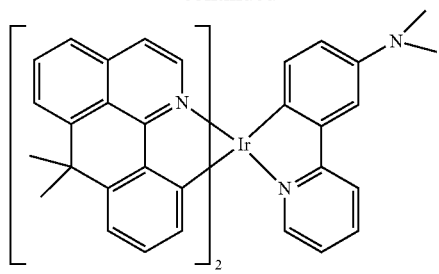
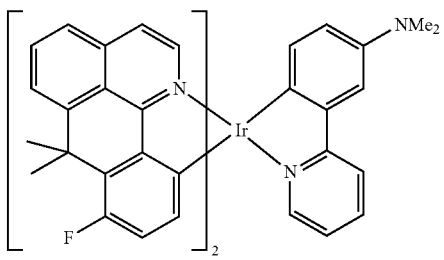
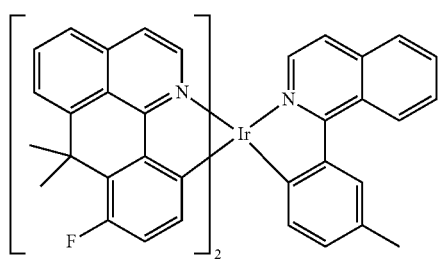
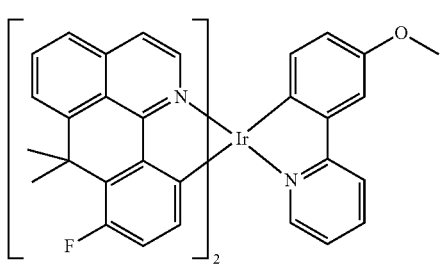
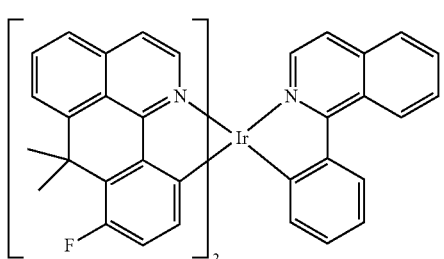
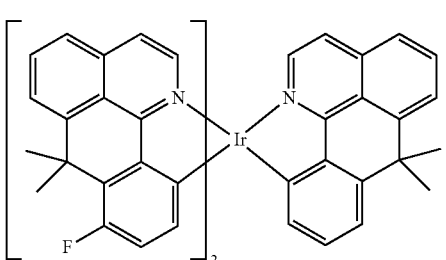
-continued
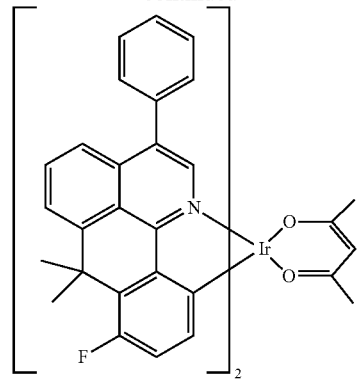
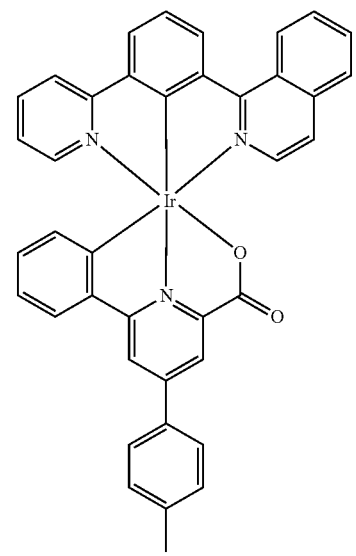
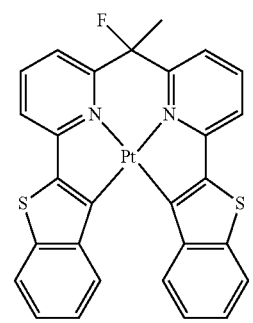

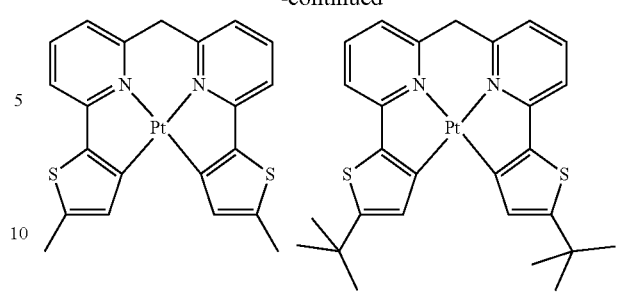
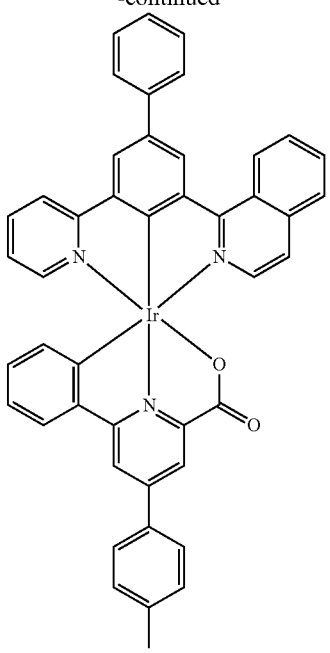
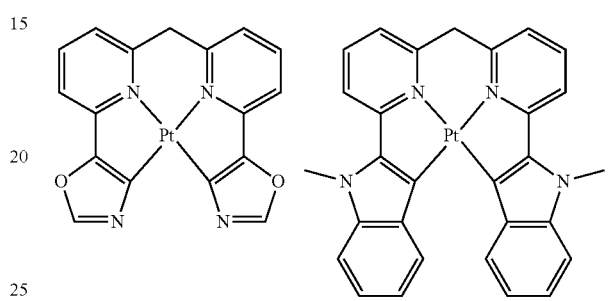
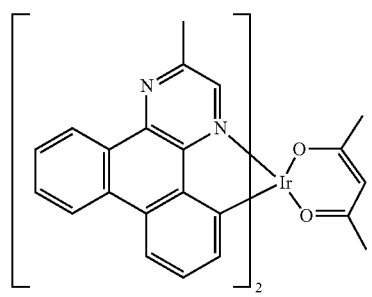
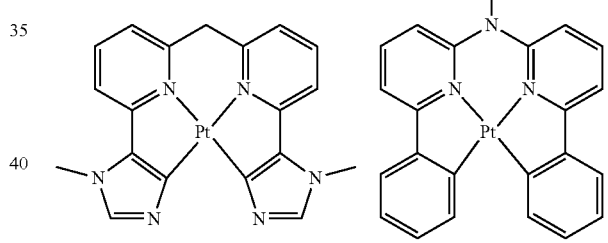
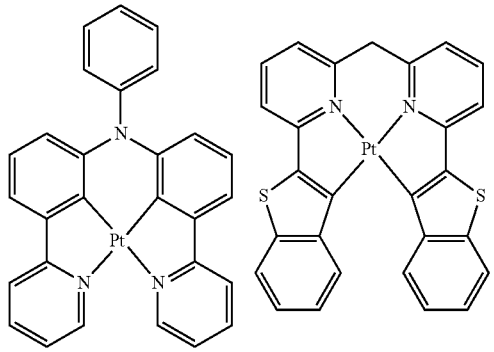
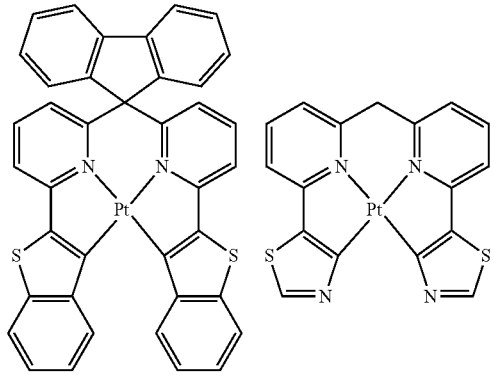
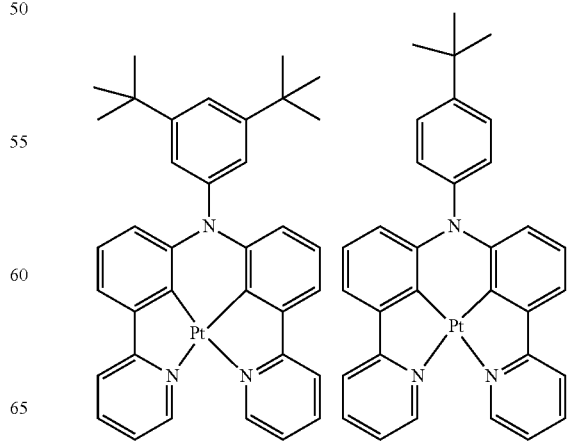

99
-continued
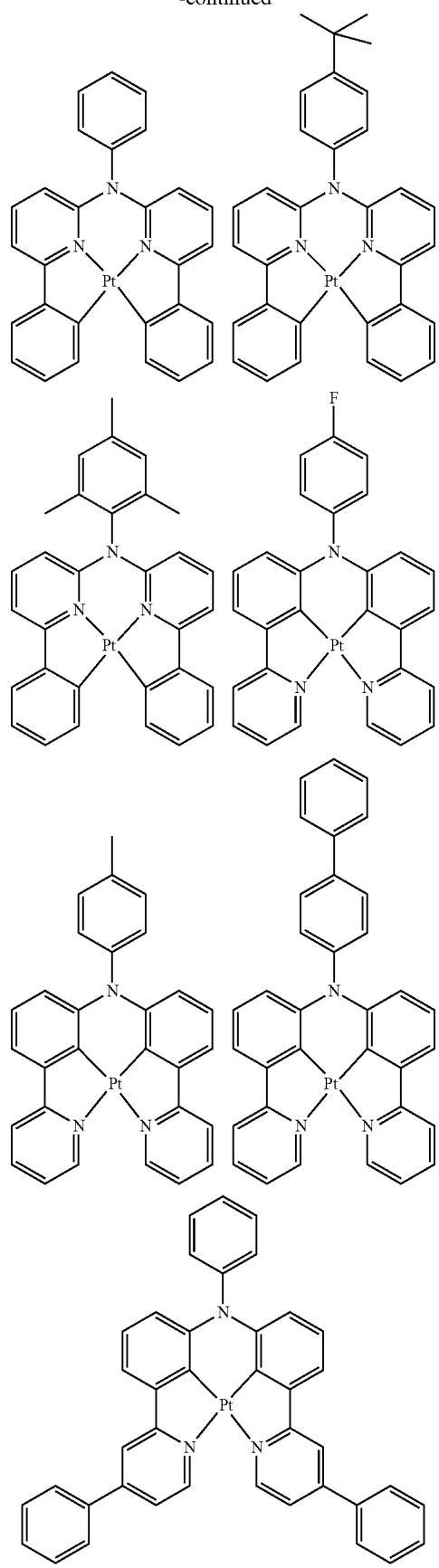
100
-continued
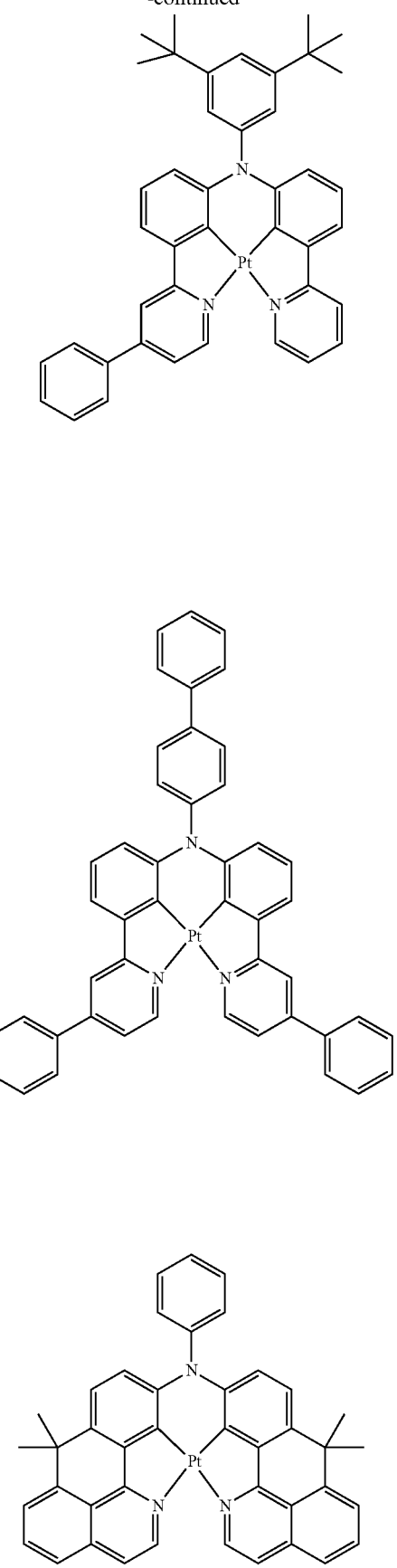

101
-continued
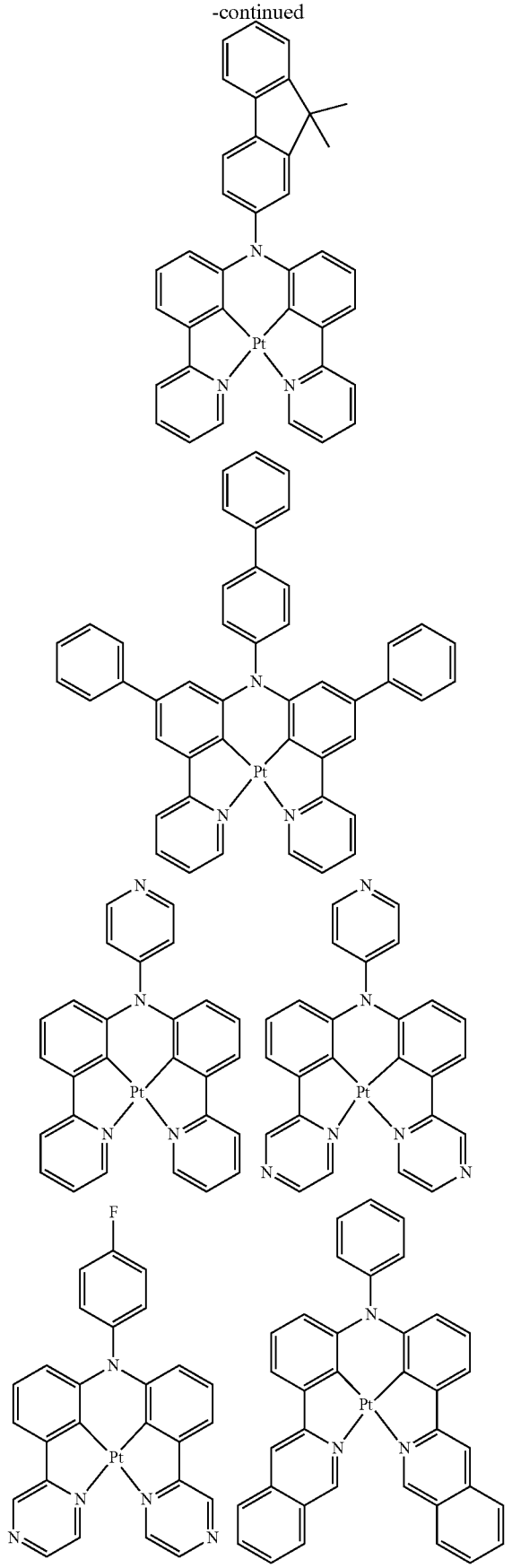
102
-continued
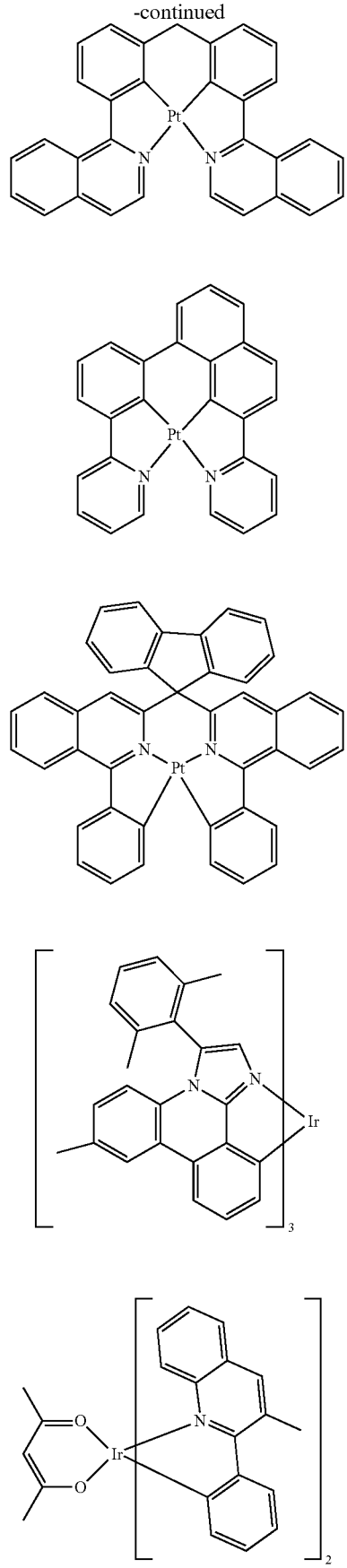

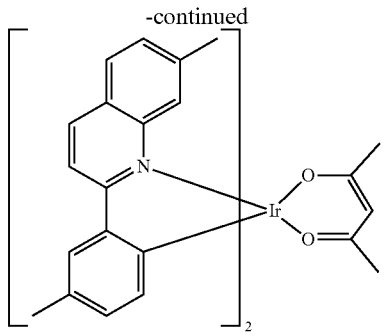
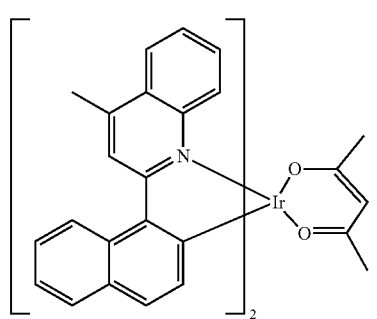
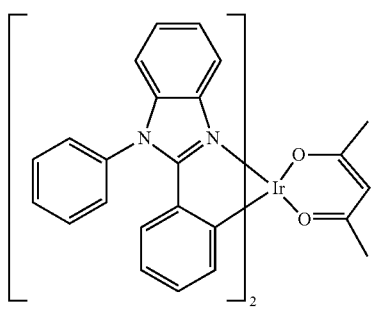
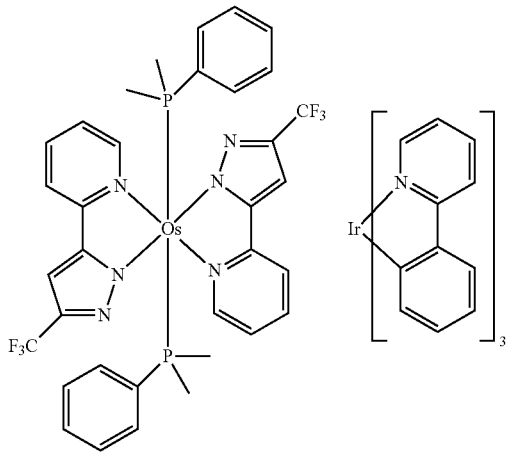
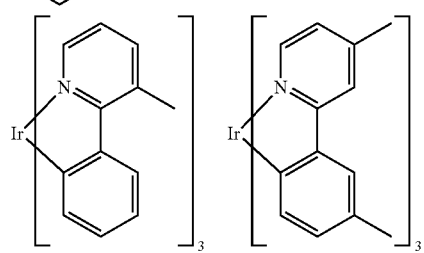
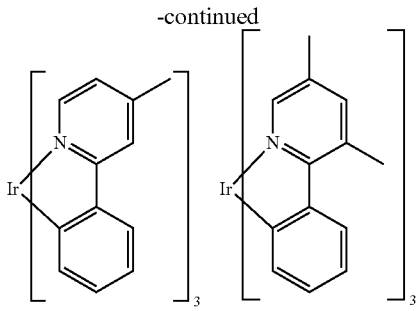
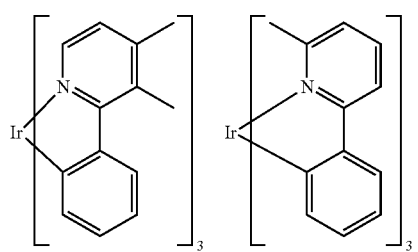
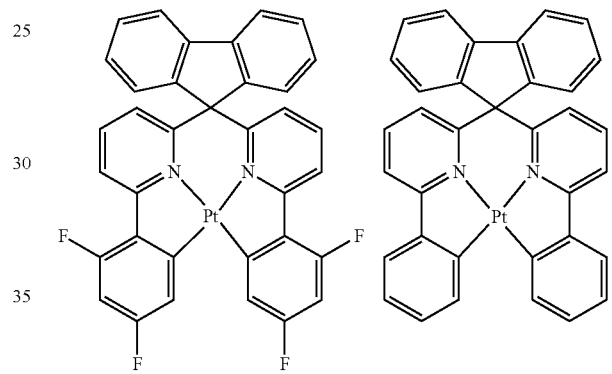
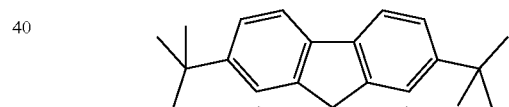
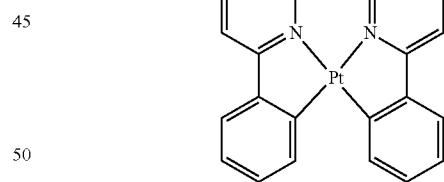
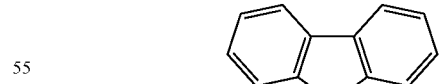
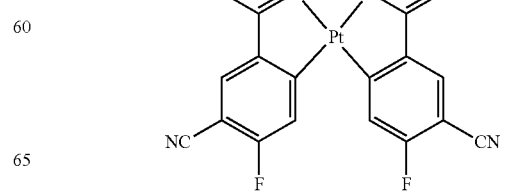

105
-continued
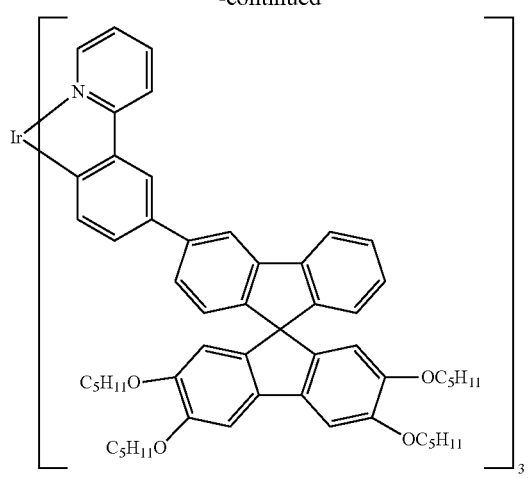
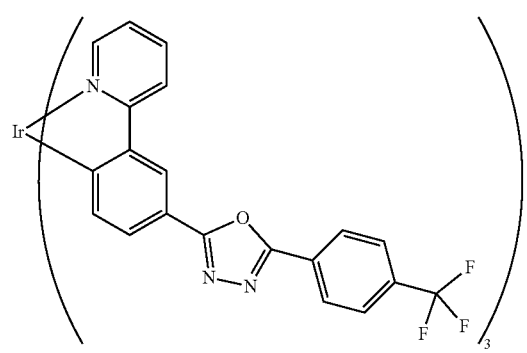
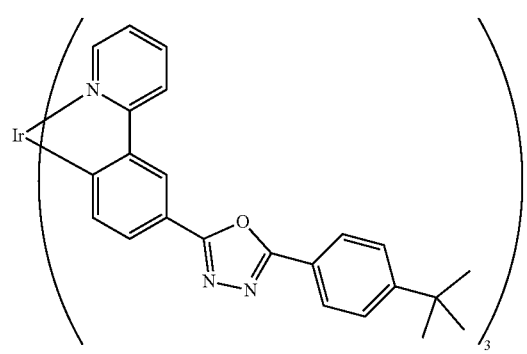
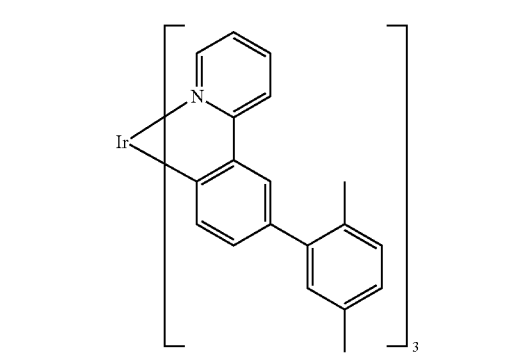
106
-continued
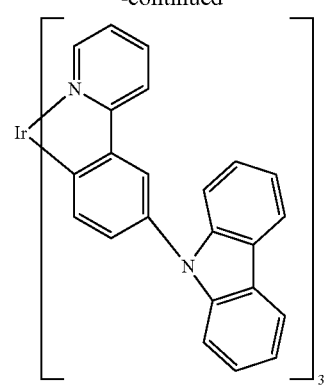
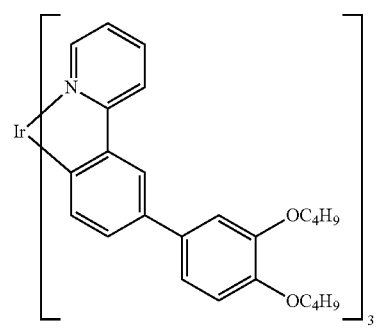
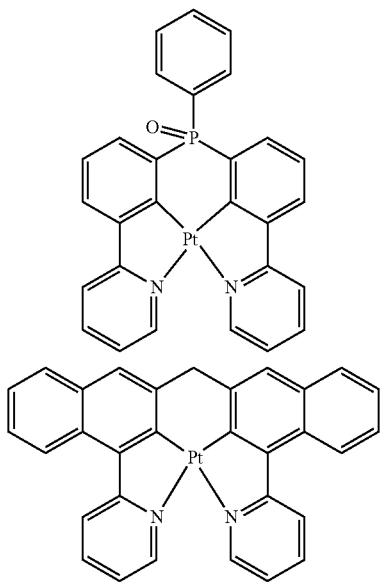
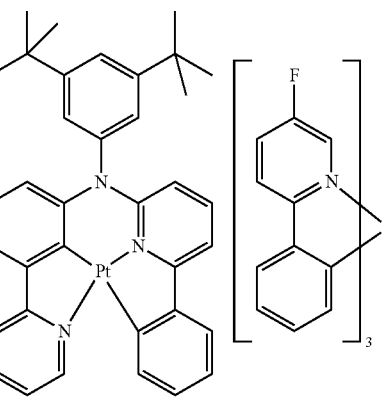

107
-continued
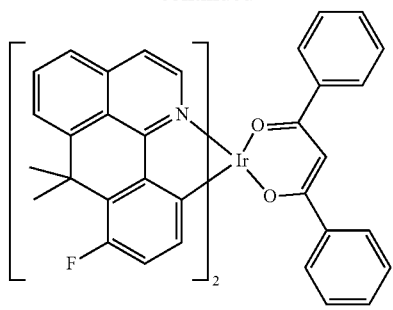
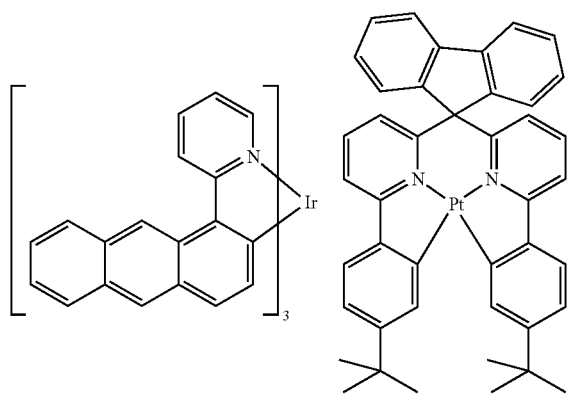
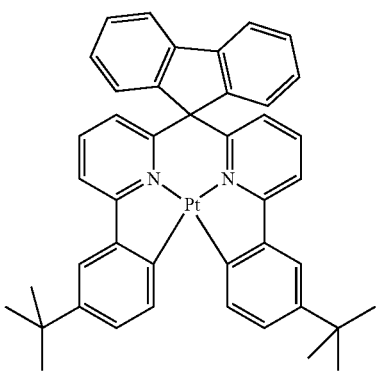
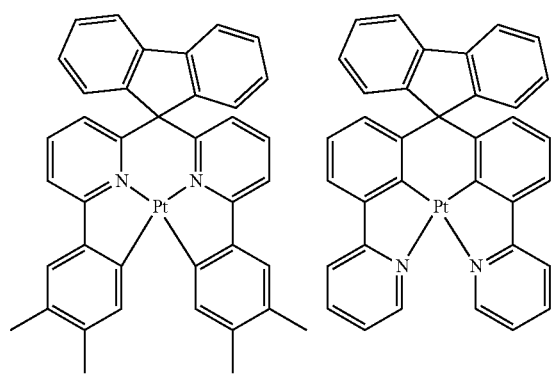
108
-continued
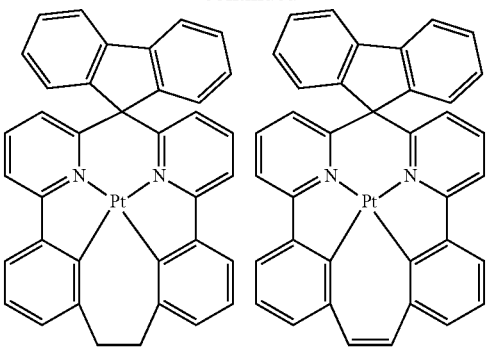
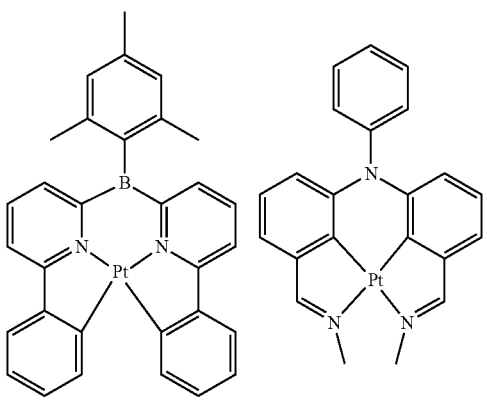
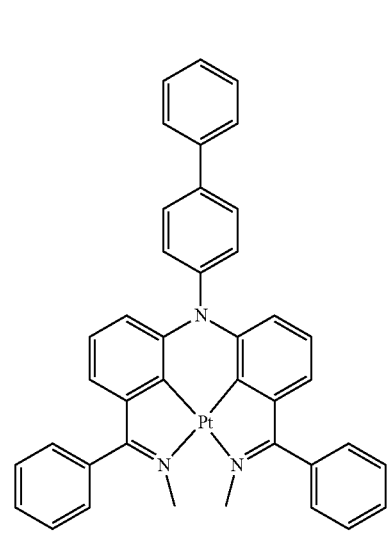
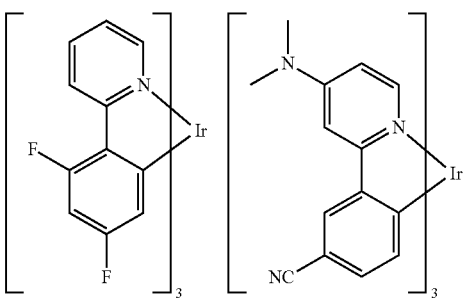

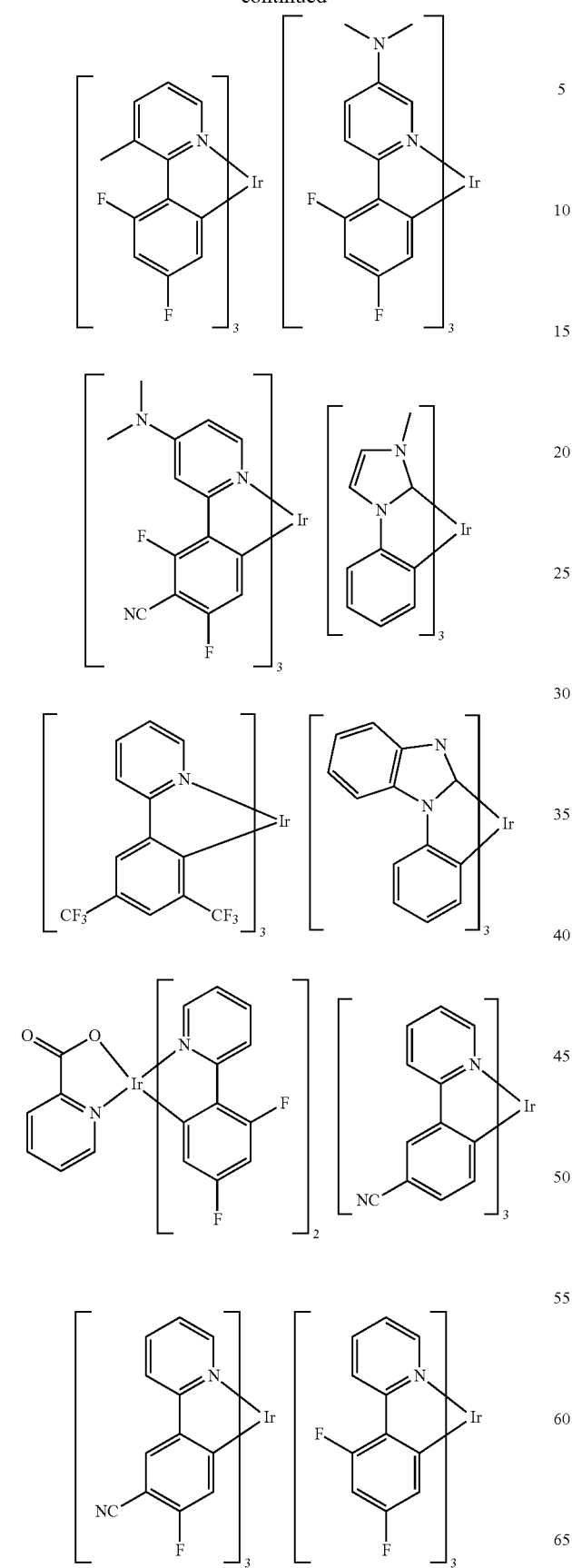
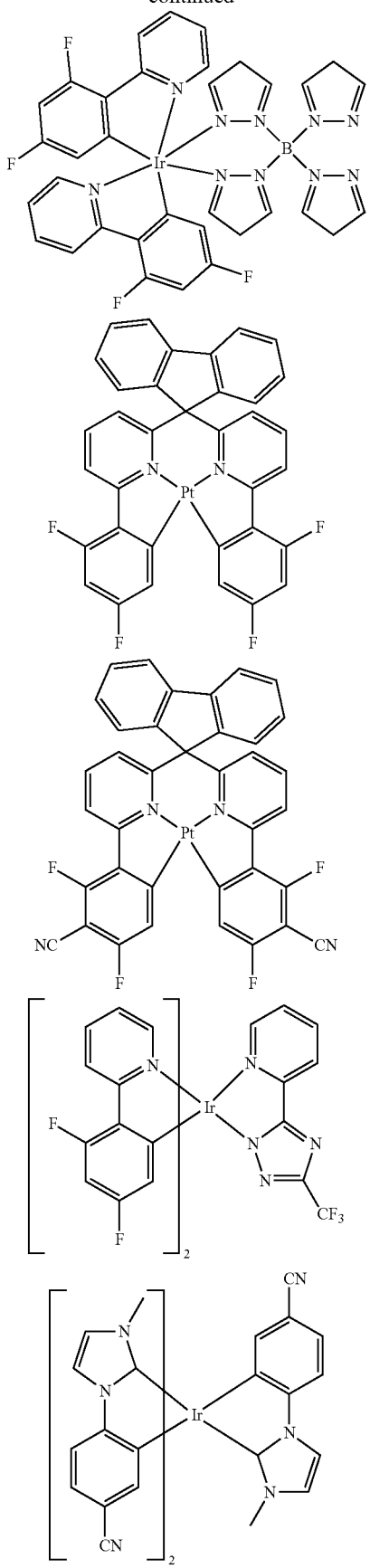

111
-continued
112
-continued
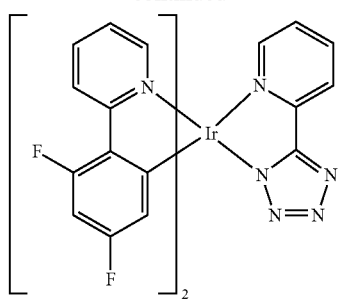
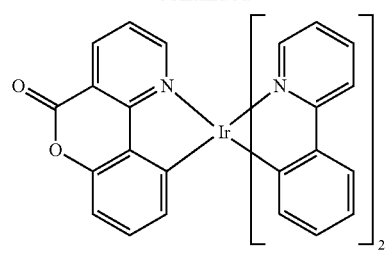
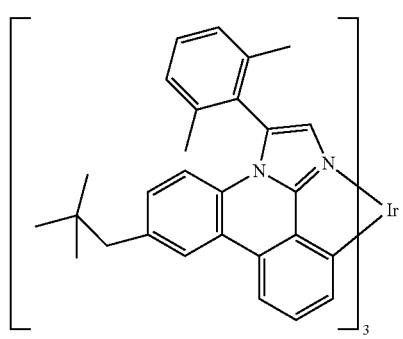
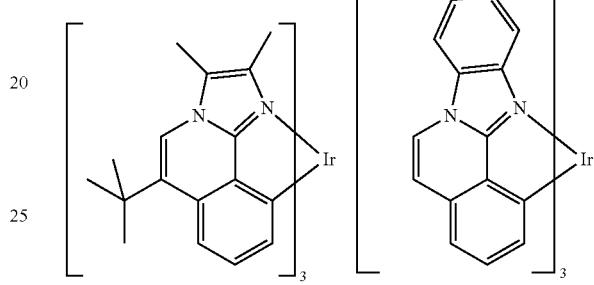
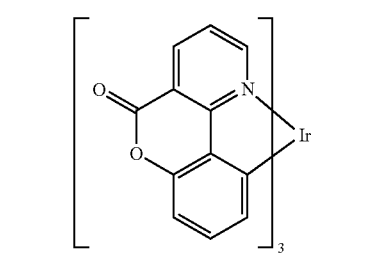
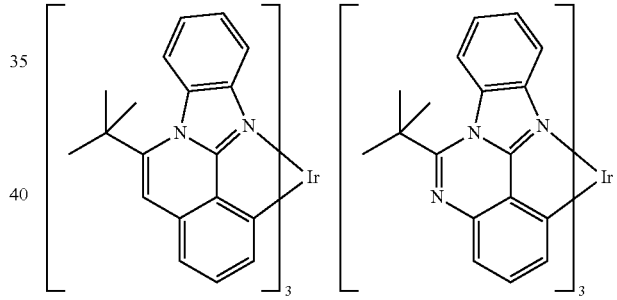
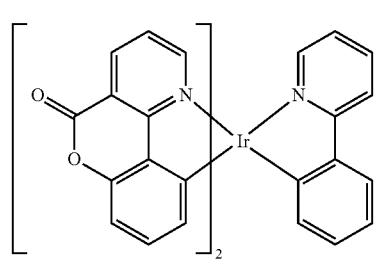

In a further embodiment of the invention, the inventive organic electroluminescent device does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the inventive organic electroluminescent device, it is possible to use any materials as typically used according to the prior art. The person skilled in the art is therefore able, without exercising inventive skill, to use any materials known for organic electroluminescent devices in combination with the inventive compounds of formula (1) or according to the preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. It is also possible that the initial pressure is even lower or higher, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example inkjet printing, LITI (light-induced thermal imaging, thermal transfer printing), screen printing, flexographic printing, offset printing or nozzle printing. For this purpose, soluble compounds are needed, which are obtained, for example, through suitable substitution. These methods are especially also suitable for oligomers, dendrimers and polymers.

In addition, hybrid methods are possible, in which, for example, one or more layers are applied from solution and one or more further layers are applied by vapour deposition. For example, it is possible to apply the emitting layer from solution and to apply the electron transport layer by vapour deposition.

These methods are known in general terms to those skilled in the art and can be applied without exercising inventive skill to organic electroluminescent devices comprising the inventive compounds.

The inventive compounds, when used in organic electroluminescent devices, have one or more of the following surprising advantages over the prior art:

1. Higher power efficiency of corresponding devices compared to systems according to the prior art.
2. Higher stability of corresponding devices compared to systems according to the prior art, which is manifested particularly in a much longer lifetime.
3. The inventive organic electroluminescent devices have a reduced operating voltage.
4. When the inventive compounds are used as matrix material for phosphorescent emitters, it is already possible to achieve very good results with only a low emitter concentration in the region of less than 10% by volume.
5. The inventive compounds have a very good thermal stability.

The invention is now illustrated in detail by the examples which follow, without any intention of restricting it thereby.

WORKING EXAMPLES

Scheme 1:

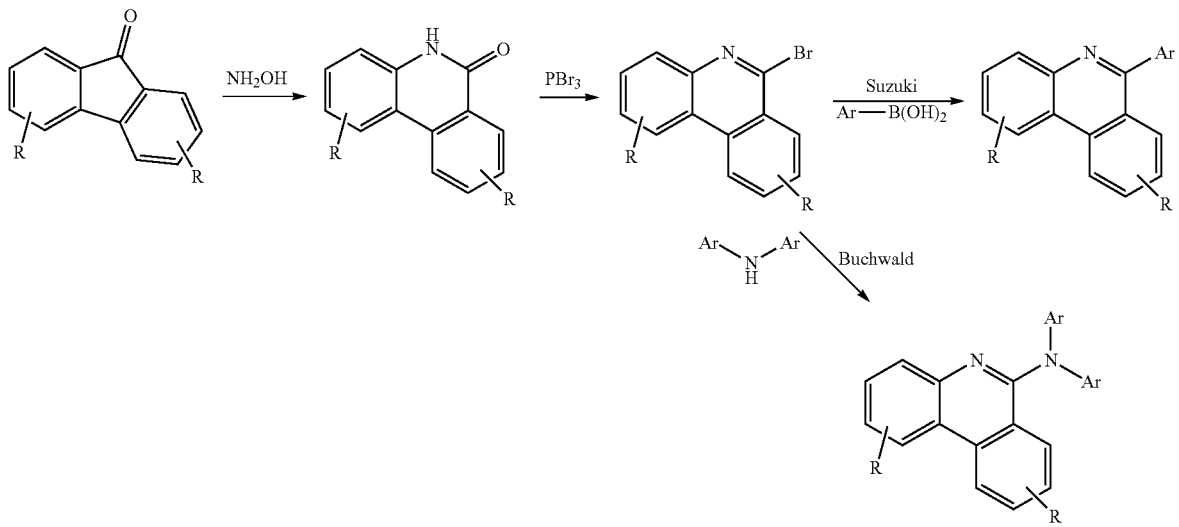

Scheme 1 shows one possible synthesis route. R is any radical and Ar is a heteroaromatic ring system of the formula $(Ar^2)_q N(Ar^1)_2$, or $Ar^1$ in the case of Buchwald coupling. Rather than Br, it is also possible for another group suitable for coupling to be present, such as a chlorine or iodine or a sulfonic acid group. Proceeding from fluorenone, via a Beckmann rearrangement, it is possible to obtain 5H-phenanthridin-6-one. From this, with PBr₃, it is possible to obtain 6-bromophenanthridine. This compound can be converted to the compounds of the invention by organometallic couplings such as Suzuki or Buchwald couplings.

Unless stated otherwise, the syntheses which follow are conducted under a protective gas atmosphere. The reactants can be sourced from ALDRICH or ABCR (palladium(II) acetate, tri-o-tolylphosphine, inorganic substances, solvents).

Example 1: 3-Bromo-9-[1,1';3',1"]terphenyl-5'-yl-9H-carbazole

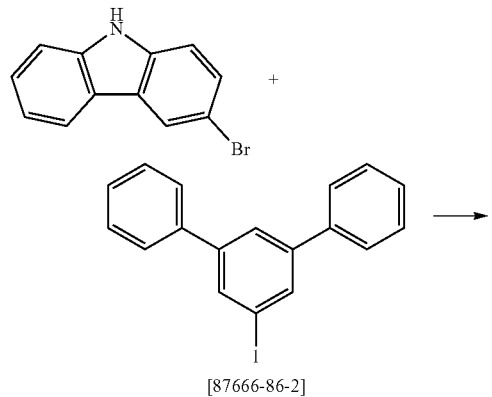

[87666-86-2]

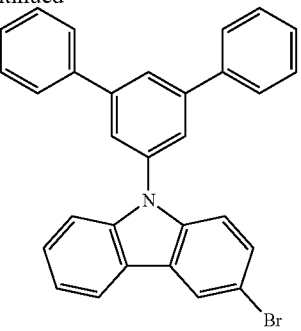

10 g (41 mmol) of 3-bromo-9H-carbazole (CAS 86-74-8) and 16 g (45 mmol, 1.1 eq) of 5'-iodo-[1,1';3',1"]terphenyl are dissolved together with 9.2 g (160 mmol, 4 eq) of potassium hydroxide, 300 mg (1.6 mmol, 0.04 eq) 1,10-phenanthroline and 160 mg (1.6 mmol, 0.04 eq) of copper(I) iodide in 250 ml of p-xylene, and the mixture is heated under reflux. After the reaction has ended, the mixture is extracted three times with water and the organic phase is dried over sodium sulfate, the solvent is removed under reduced pressure and the solids obtained are purified by means of column chromatography (ethyl acetate/heptane). 17 g (36 mmol, 88%) of the desired product are obtained.

In an analogous manner, it is possible to obtain the following compounds

| Ex. | Reactant 1 | Reactant 2 | Product | Yield [%] |
|---|---|---|---|---|
| 1a | CAS 86-74-8 | CAS 20442-79-9 | | 94 |
| 1b | CAS 86-74-8 | CAS 28320-31-2 | | 91 |

Example 2: 9-(9,9-Dimethyl-9H-fluoren-2-yl)-9H-carbazole-3-boronic Acid

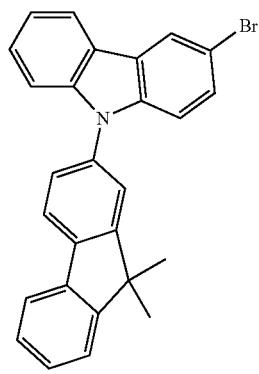

22.3 g (51 mmol) of 3-bromo-9-(9,9-dimethyl-9H-fluoren-2-yl)-9H-carbazole are dissolved in 600 ml of dry THF and cooled to −78° C. At this temperature, 26.2 ml (65.7 mmol/2.5 M in hexane) of n-BuLi are added within about 5 min. and then the mixture is stirred at −78° C. for 2.5 h. At this temperature, 7.3 ml (65.7 mmol) of trimethyl borate are added very rapidly and the reaction is allowed to come gradually to RT (about 18 h). The reaction solution is washed with water and the precipitated solids and the organic phase are subjected to azeotropic drying with toluene. The crude product is extracted by stirring from toluene/methylene chloride at about 40° C. and filtered with suction. 17.5 g (85%) of the product are obtained as a white solid.

In an analogous manner, it is possible to obtain the following compounds:

Example 3: 3-(5-Bromobiphenyl-3-yl)-9-phenyl-9H-carbazole

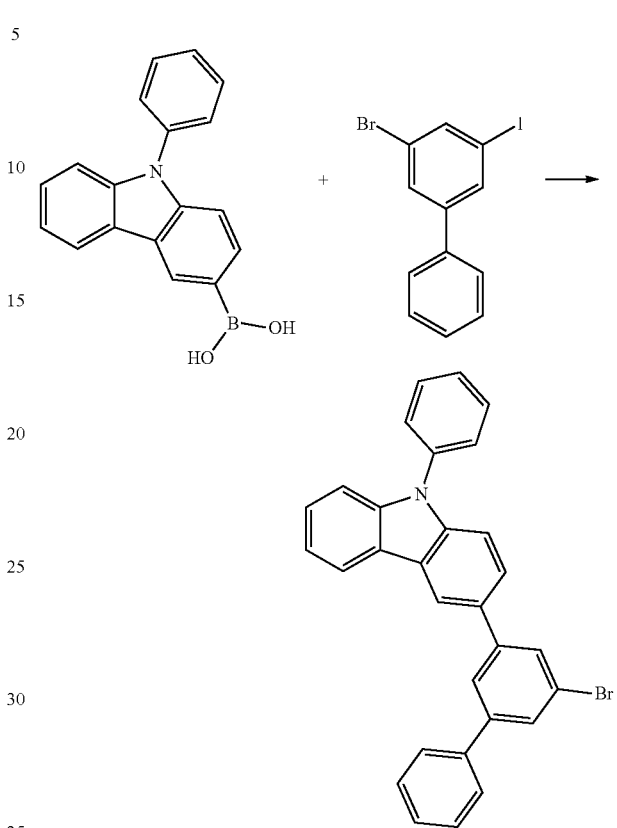

15.5 g (43.3 mmol) of 3-bromo-5-iodobiphenyl and 13.7 g (48 mmol) of (9-phenyl-9H-carbazol-3-yl)boronic acid are dissolved in 80 ml of toluene and degassed. 281 ml of a degassed 2 M $K_2CO_3$ solution and 2.5 g (2.2 mmol) of $Pd(OAc)_2$ are added. The reaction mixture is then stirred at 80° C. under a protective gas atmosphere for 48 h. The cooled solution is diluted with toluene, washed repeatedly with water, dried and concentrated. The product is purified via column chromatography on silica gel with toluene/heptane (1:2). The purity is 98%. Yield: 17.6 g (37 mmol, 78%) of theory.

| Ex. | Reactant 1 | Product | Yield [%] |
|---|---|---|---|
| 2a | ![structure] | ![structure] | 79 |

In an analogous manner, it is possible to obtain the following compounds:
| Ex. | Reactant 1 | Reactant 2 | Product | Yield [%] |
|---|---|---|---|---|
| 3a | 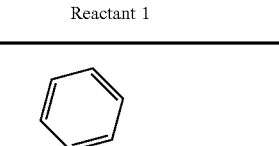 854952-60-6 | 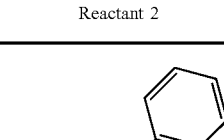 136649-44-0 | 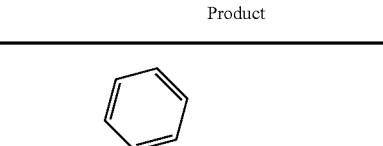 | 70 |
| 3b | 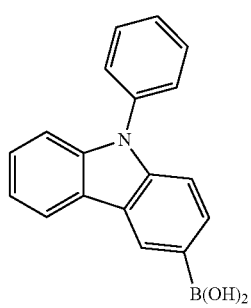 854952-58-2 | 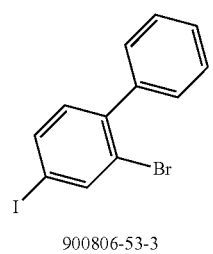 [SMILES: Brc1cc(I)ccc1-c1ccccc1] 900806-53-3 | 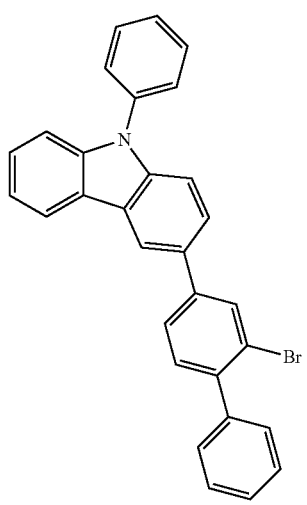 [SMILES: Brc1cc(-c2ccc3c(c2)c2ccccc2n3-c2ccccc2)ccc1-c1ccccc1] | 69 |

| Ex. | Reactant 1 | Reactant 2 | Product | Yield [%] |
|---|---|---|---|---|
| 3c | 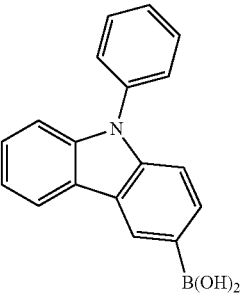 854952-58-2 | 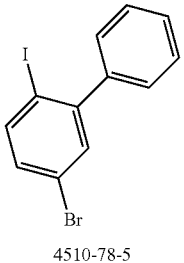 [SMILES: Brc1ccc(I)c(-c2ccccc2)c1] 4510-78-5 | 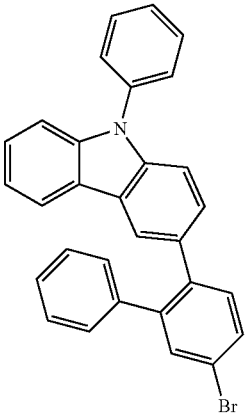 [SMILES: Brc1ccc(-c2ccc3c(c2)c2ccccc2n3-c2ccccc2)c(-c2ccccc2)c1] | 68 |
| 3d | 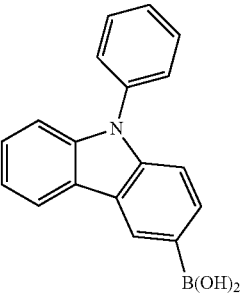 854952-58-2 | 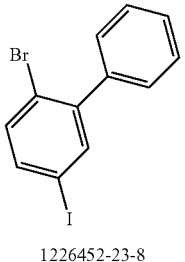 [SMILES: Brc1ccc(I)cc1-c1ccccc1] 1226452-23-8 | 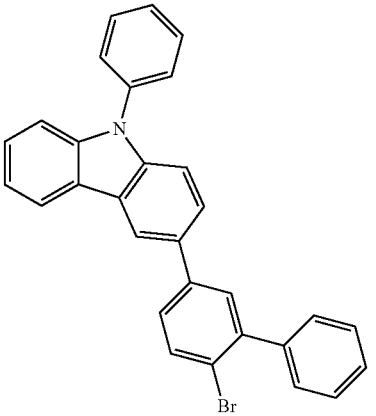 [SMILES: Brc1ccc(-c2ccc3c(c2)c2ccccc2n3-c2ccccc2)cc1-c1ccccc1] | 83 |
Example 4: 3-(5-boronic acid-biphenyl-3-yl)-9-phenyl-9H-carbazole
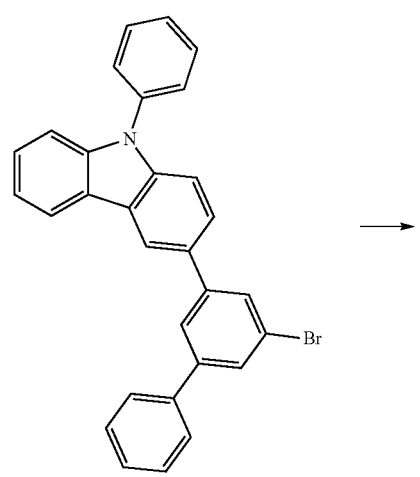 → 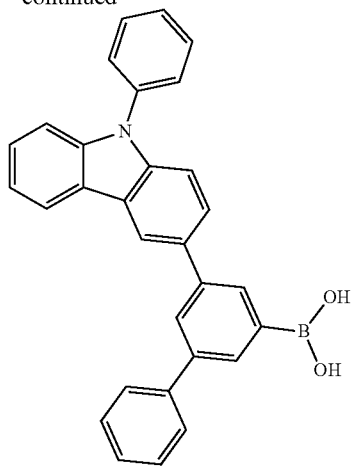
To a solution, cooled to −78° C., of 128 g (270 mmol) of 3-(5-bromobiphenyl-3-yl)-9-phenyl-9H-carbazole in 1500 ml of diethyl ether are added dropwise 110 ml (276 mmol) of n-butyllithium (2.5 M in hexane). The reaction mixture is stirred at −78° C. for 30 minutes. The mixture is allowed to come to room temperature and cooled again to −78° C., and then a mixture of 40 ml (351 mmol) of trimethyl borate in 50 ml of diethyl ether is added rapidly. After warming to −10° C., hydrolysis is effected with 135 ml of 2 N hydrochloric acid. The organic phase is removed, washed with water, dried over sodium sulfate and concentrated to dryness. The residue is taken up in 300 ml of n-heptane, and the colourless solids are filtered off with suction, washed with n-heptane and dried under reduced pressure. Yield: 112 g (256 mmol), 95% of theory.

In an analogous manner, it is possible to obtain the following compounds:

| Ex. | Reactant 1 | Product | Yield [%] |
|---|---|---|---|
| 4a | | | 59 |
| 4b | | | 60 |
| 4e | | | 59 |

| Ex. | Reactant 1 | Product | Yield [%] |
|---|---|---|---|
| 4f | 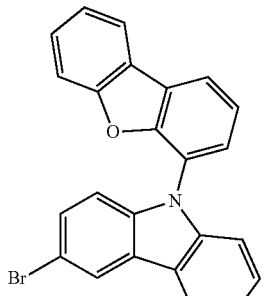 1345970-20-8 | 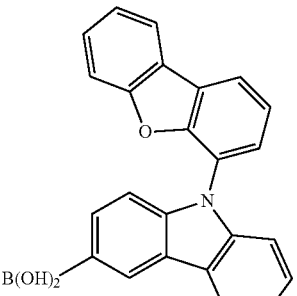 | 83 |

Example 5: 6-(9-Phenyl-9H-carbazol-3-yl)phenanthridine

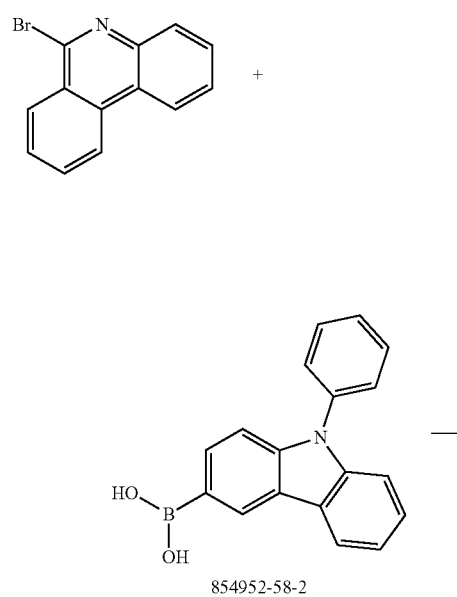

854952-58-2

→

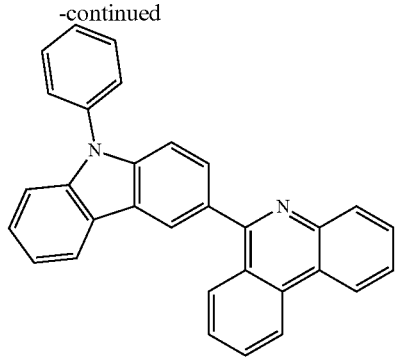

28.9 g (43.3 mmol) of 6-bromophenanthridine and 13.7 g (48 mmol) of 9-phenyl-9H-carbazole-3-boronic acid are dissolved in 80 ml of toluene and degassed. 281 ml of a degassed solution of 2 M $K_2CO_3$ and 2.5 g (2.2 mmol) of $Pd(OAc)_2$ are added. The reaction mixture is then stirred under a protective gas atmosphere at 80° C. for 48 h. The cooled solution is supplemented with toluene, washed repeatedly with water, dried and concentrated. The product is purified via column chromatography on silica gel with toluene/heptane (1:2) and finally sublimed under high vacuum ($p=5\times10^{-7}$ mbar). The purity is 99.9%. Yield: 28 g (31 mmol), 80% of theory.

In an analogous manner, it was possible to obtain the following compounds:

| Ex. | Reactant 1 | Reactant 2 | Product | Yield [%] |
|---|---|---|---|---|
| 5a | 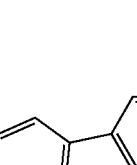 [17613-40-0] | 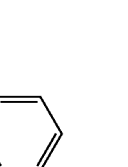 1333002-37-1 |  | 59 |
| 5b | 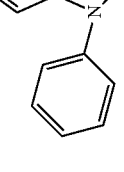 [17613-40-0] | 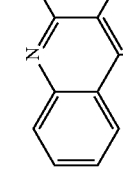 1338488-91-7 | 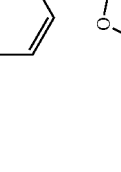 | 60 |

| Ex. | Reactant 1 | Reactant 2 | Product | Yield [%] |
|---|---|---|---|---|
| 5c | 6-bromophenanthridine [17613-40-0] | 9-phenyl-9'-phenyl-[3,3'-bicarbazole]-6-boronic acid | | 67 |
| 5d | 6-bromophenanthridine [17613-40-0] | 9-(dibenzofuran-4-yl)-[9,3'-bicarbazole]-6'-boronic acid 918137-86-7 | | 69 |

-continued

| Ex. | Reactant 1 | Reactant 2 | Product | Yield [%] |
|---|---|---|---|---|
| 5e | [17613-40-0] | 854952-60-6 | | 71 |
| 5f | [17613-40-0] | | | 73 |

| Ex. | Reactant 1 | Reactant 2 | Product | Yield [%] |
|---|---|---|---|---|
| 5g | 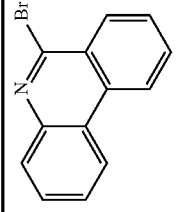 [17613-40-0] | 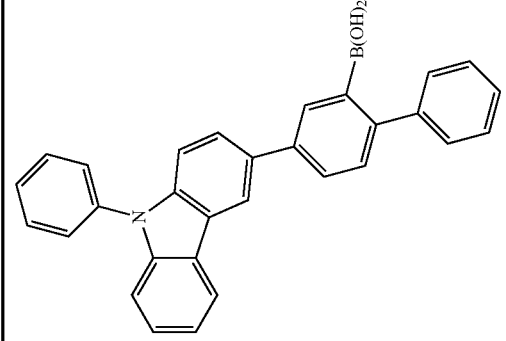 | 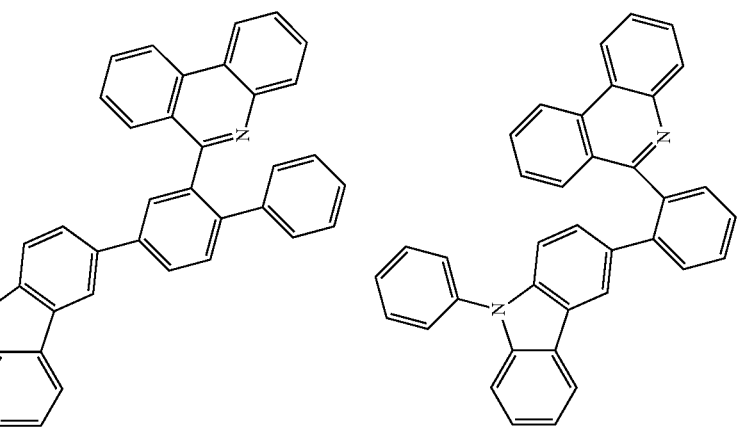 | 66 |
| 5h | 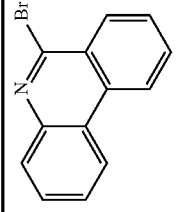 [17613-40-0] | 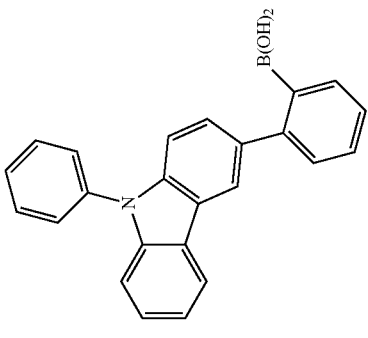 | 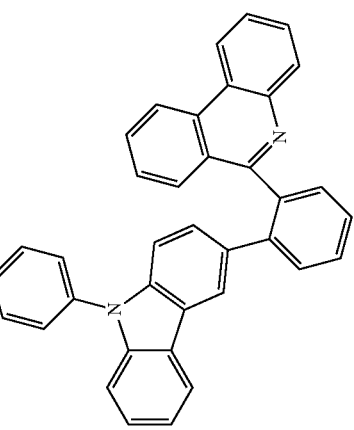 | 75 |

-continued
| Ex. | Reactant 1 | Reactant 2 | Product | Yield [%] |
|---|---|---|---|---|
| 5i | 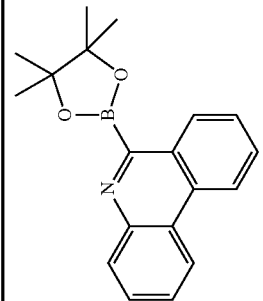 [890042-19-0] | 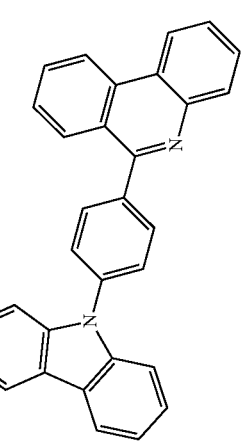 1361126-22-8 | 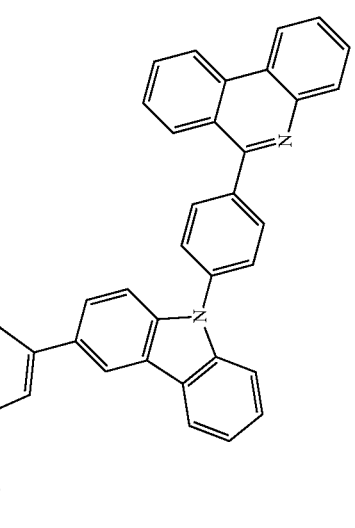 | 78 |
| 5j | 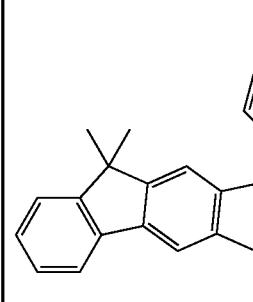 [890042-19-0] | 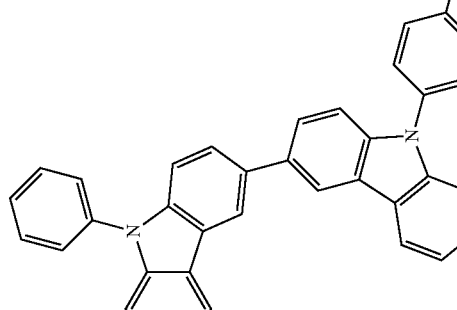 | 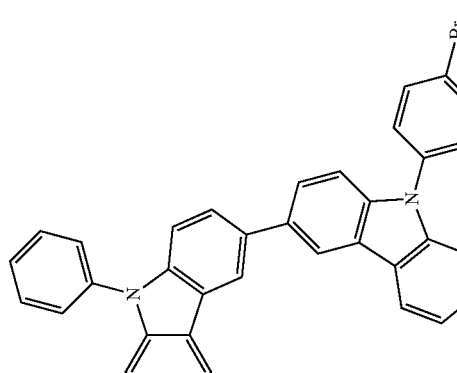 | 81 |

-continued

| Ex. | Reactant 1 | Reactant 2 | Product | Yield [%] |
|---|---|---|---|---|
| 5k | [17613-40-0] | [1379585-25-7] | | 82 |
| 5l | [124662-60-1] | 854952-58-2 | | 84 |

| Ex. | Reactant 1 | Reactant 2 | Product | Yield [%] |
|---|---|---|---|---|
| 5m | 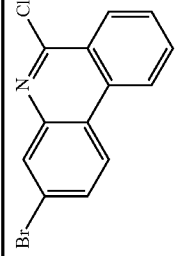 [847900-59-8] | 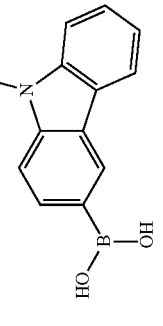 854952-58-2 | 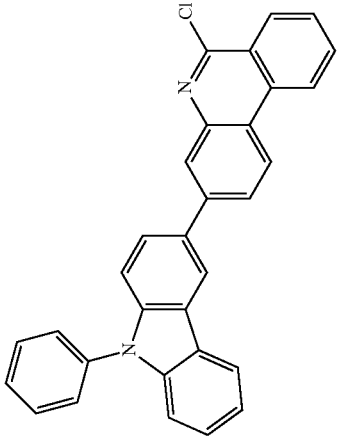 | 80 |
| 5n | 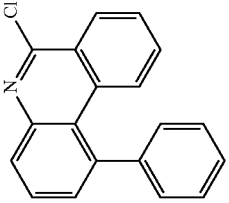 [17613-46-6] | 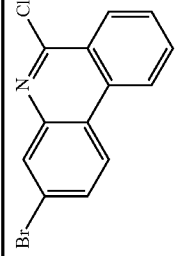 B(OH)$_2$ | 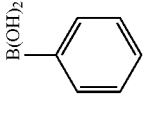 | 84 |

| Ex. | Reactant 1 | Reactant 2 | Product | Yield [%] |
|---|---|---|---|---|
| 5o | (phenyl-carbazole-phenanthridine-Cl) | (N-phenylcarbazole-3-boronic acid) [854952-58-2] | (bis-carbazole phenanthridine product) | 79 |
| 5p | (Cl-phenanthridine-carbazole-phenyl) | (dimethylfluorene-carbazole-boronic acid) [1379585-25-7] | (indenocarbazole-phenanthridine-carbazole product) | 78 |

-continued

| Ex. | Reactant 1 | Reactant 2 | Product | Yield [%] |
|---|---|---|---|---|
| 5q | (6-chloro-phenyl-phenanthridine) | (9-phenyl-carbazole-3-boronic acid) 854952-58-2 | | 77 |
| 5r | (6-bromophenanthridine) [17613-40-0] | (triazine-carbazole pinacol boronate) 1381094-91-8 | | 89 |

-continued

| Ex. | Reactant 1 | Reactant 2 | Product | Yield [%] |
|---|---|---|---|---|
| 5r1 | ![Br-phenanthridine] [17613-40-0] | ![boronic ester reactant] 1346010-98-7 | ![product] | 82 |

In an analogous manner, it is possible to obtain the following compounds with 0.5 eq. of phenanthridine:

| Ex. | Reactant 1 | Reactant 2 | Product | Yield [%] |
|---|---|---|---|---|
| 5s | 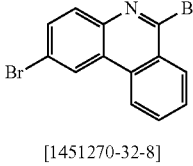 [1451270-32-8] | 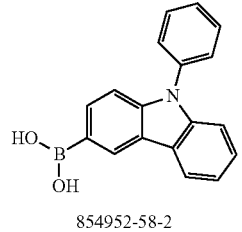 [SMILES: OB(O)c1ccc2c(c1)c1ccccc1n2-c1ccccc1] 854952-58-2 | 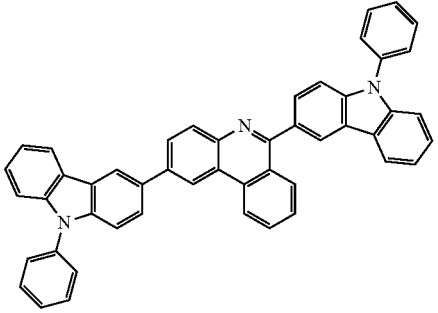 [SMILES: c1ccc(-n2c3ccccc3c3cc(-c4ccc5nc(-c6ccc7c(c6)c6ccccc6n7-c6ccccc6)c6ccccc6c5c4)ccc32)cc1] | 69 |

Example 6: (9,9-Dimethyl-9H-fluoren-2-yl)-{4-[(Z)-1-eth-(E)-ylidene-penta-2,4-dienyl]phenyl}amine

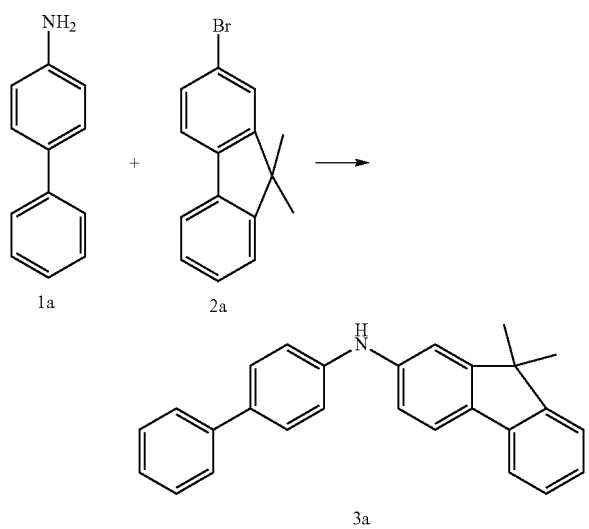

24.0 g (142 mmol, 1.2 eq.) of 4-aminobiphenyl 1a (CAS 92-67-1) are initially charged together with 32.0 g (117 mmol, 1.0 eq) of 2-bromo-9,9'-dimethylfluorene 2a (CAS 28320-31-2) in 950 ml of toluene, and the mixture is saturated with argon for 30 minutes. Subsequently, 1.0 g (1.8 mmol, 0.02 eq) of 1,1'-bis(diphenylphosphino)ferrocene (CAS 12150-46-8), 350 mg (1.6 mmol, 0.01 eq) of palladium(II) acetate (CAS 3375-31-3) and 29 g (300 mmol, 2.6 eq) of sodium tert-butoxide (CAS 865-48-5) are added and heated under reflux overnight. After the reaction has ended, the mixture is diluted with 300 ml of toluene and extracted with water. The organic phase is dried over sodium sulfate and the solvent is removed by rotary evaporator. The brown oil is admixed with 50 ml of ethyl acetate and added to a mixture of heptane/ethyl acetate 20:1. The resultant solids are filtered off with suction and washed with heptane. After drying, 29 g (80 mmol, 69%) of the desired product 3a are obtained with an HPLC purity of 99.1%.

In an analogous manner, it is possible to obtain the following compounds:

| Ex. | Reactant 1 | Reactant 2 | Product | Yield [%] |
|---|---|---|---|---|
| 6a | 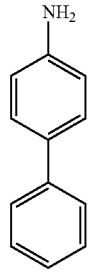 92-67-1 | 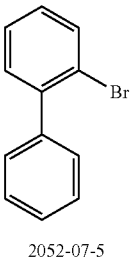 [SMILES: Brc1ccccc1-c1ccccc1] 2052-07-5 | 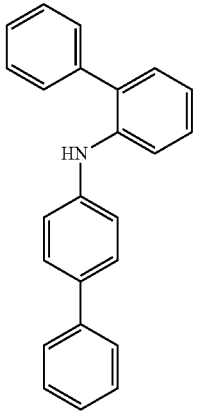 [SMILES: c1ccc(-c2ccc(Nc3ccccc3-c3ccccc3)cc2)cc1] | 71 |

-continued
| Ex. | Reactant 1 | Reactant 2 | Product | Yield [%] |
|---|---|---|---|---|
| 6b | 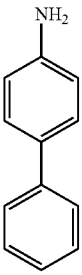<br>92-67-1 | 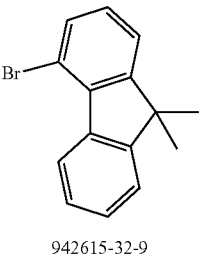 [SMILES: CC1(C)c2ccccc2-c2c(Br)cccc21]<br>942615-32-9 | 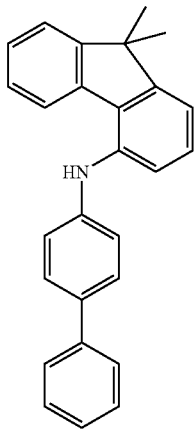 [SMILES: CC1(C)c2ccccc2-c2c(Nc3ccc(-c4ccccc4)cc3)cccc21] | 61 |
| 6c | 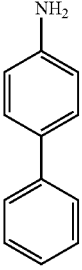<br>92-67-1 | 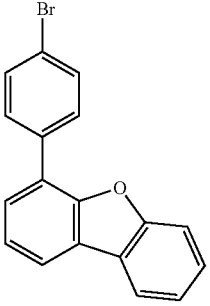<br>955959-84-9 | 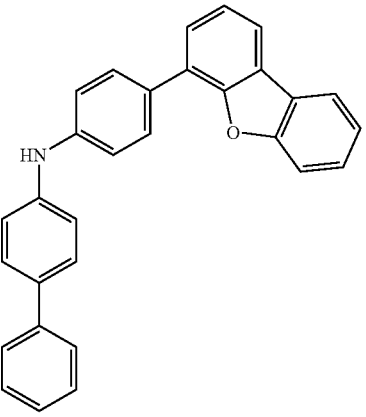 [SMILES: c1ccc(-c2ccc(Nc3ccc(-c4cccc5c4oc4ccccc45)cc3)cc2)cc1] | 78 |
| 6d | 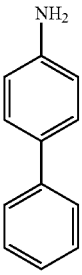<br>92-67-1 | 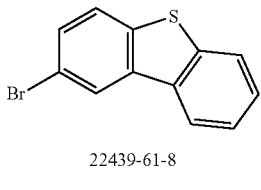 [SMILES: Brc1ccc2sc3ccccc3c2c1]<br>22439-61-8 | 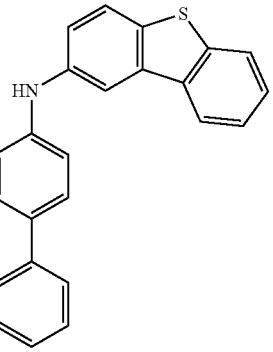 | 82 |

-continued
| Ex. | Reactant 1 | Reactant 2 | Product | Yield [%] |
|---|---|---|---|---|
| 6e | 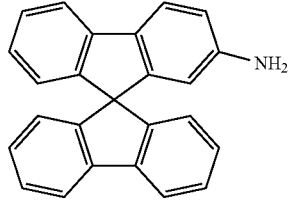<br>118951-68-1 | 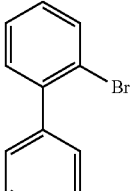<br>2052-07-5 | 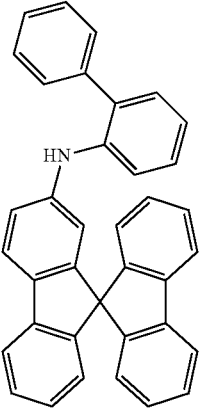 [SMILES: c1ccc(-c2ccccc2Nc2ccc3c(c2)C2(c4ccccc4-c4ccccc42)c2ccccc2-3)cc1] | 62 |
| 6f | 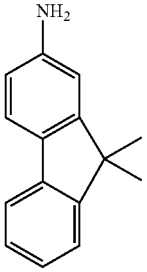<br>108714-73-4 | 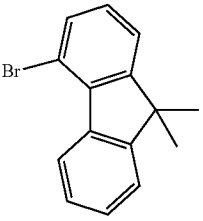<br>942615-32-9 | 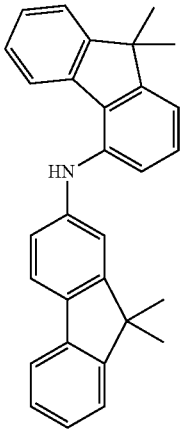 [SMILES: CC1(C)c2ccccc2-c2ccc(Nc3cccc4c3-c3ccccc3C4(C)C)cc21] | 47 |
| 6g | 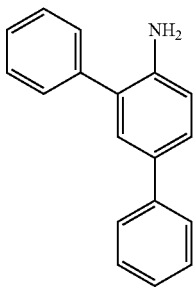<br>63344-48-9 | 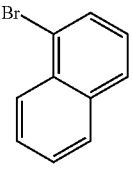<br>90-11-9 | 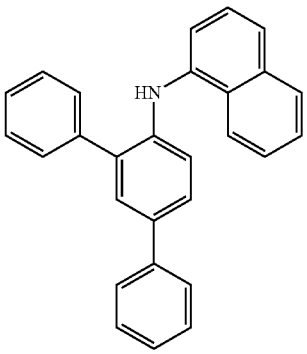 [SMILES: c1ccc(-c2ccc(Nc3cccc4ccccc34)c(-c3ccccc3)c2)cc1] | 92 |

-continued
| Ex. | Reactant 1 | Reactant 2 | Product | Yield [%] |
|---|---|---|---|---|
| 6h | 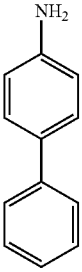  92-67-1 | 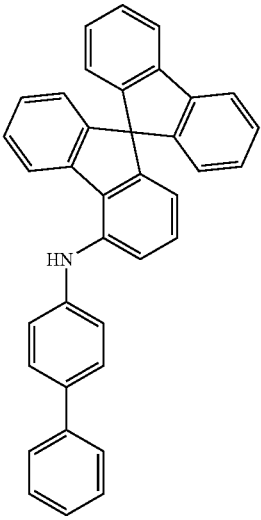 [SMILES: c1ccc(-c2ccc(Nc3cccc4c3-c3ccccc3C43c4ccccc4-c4ccccc43)cc2)cc1]  171408-76-7 | 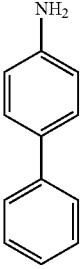 | 75 |
| 6i | 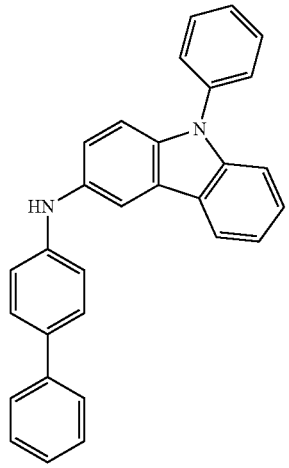 [SMILES: c1ccc(-c2ccc(Nc3ccc4c(c3)c3ccccc3n4-c3ccccc3)cc2)cc1]  92-67-1 | 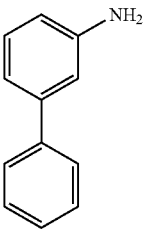  1153-85-1 | 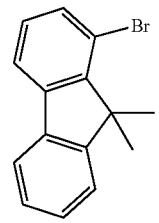 | 84 |
| 6j | 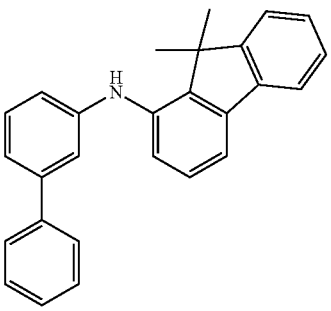 [SMILES: CC1(C)c2ccccc2-c2cccc(Nc3cccc(-c4ccccc4)c3)c21]  90-41-5 | 1225053-54-2 | | 62 |

-continued
| Ex. | Reactant 1 | Reactant 2 | Product | Yield [%] |
|---|---|---|---|---|
| 6k | 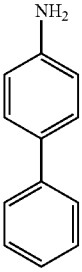<br>92-67-1 | 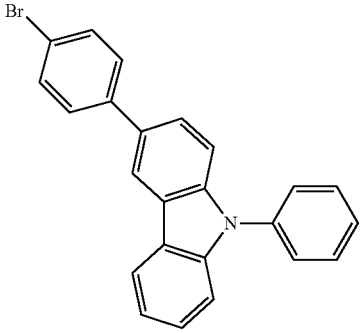<br>1028647-93-9 | 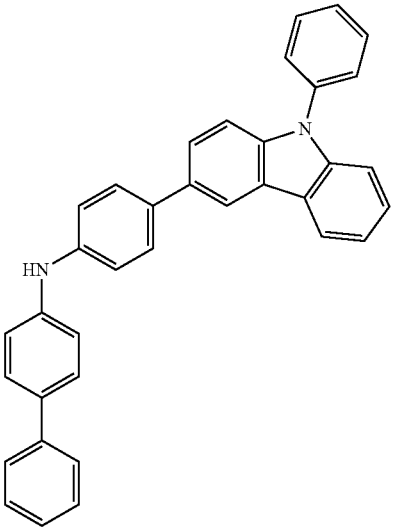 [SMILES: c1ccc(-c2ccc(Nc3ccc(-c4ccc5c(c4)c4ccccc4n5-c4ccccc4)cc3)cc2)cc1] | 78 |
| 6l | 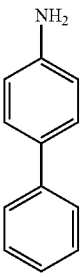<br>92-67-1 | 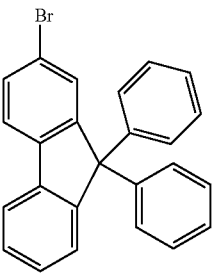<br>474918-32-6 | 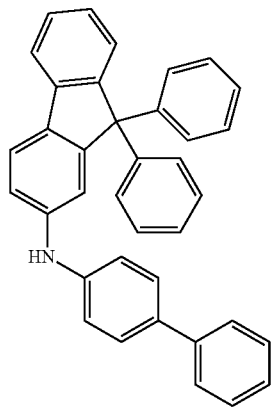 [SMILES: c1ccc(-c2ccc(Nc3ccc4c(c3)C(c3ccccc3)(c3ccccc3)c3ccccc3-4)cc2)cc1] | 74 |
| 6m | 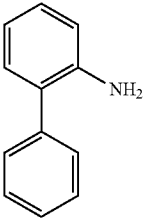<br>90-41-5 | 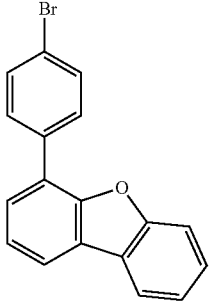<br>955959-84-9 | 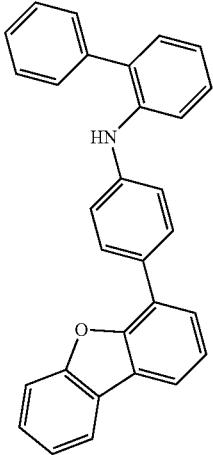 [SMILES: c1ccc(-c2ccccc2Nc2ccc(-c3cccc4c3oc3ccccc34)cc2)cc1] | 62 |

| Ex. | Reactant 1 | Reactant 2 | Product | Yield [%] |
|---|---|---|---|---|
| 6n | 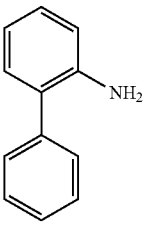<br>90-41-5 | 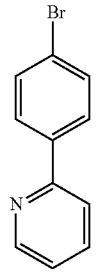<br>129013-83-8 | 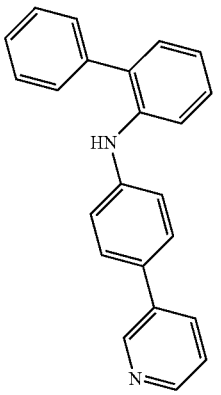 [SMILES: c1ccc(-c2ccccc2Nc2ccc(-c3cccnc3)cc2)cc1] | 67 |
| 6o | 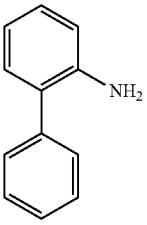<br>90-41-5 | 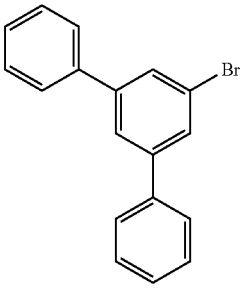<br>103068-20-8 | 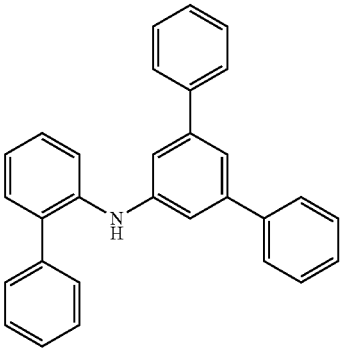 [SMILES: c1ccc(-c2cc(Nc3ccccc3-c3ccccc3)cc(-c3ccccc3)c2)cc1] | 93 |
| 6p | 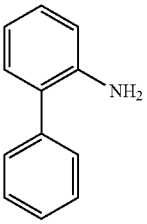<br>90-41-5 | 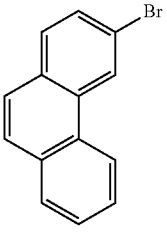<br>715-50-4 | 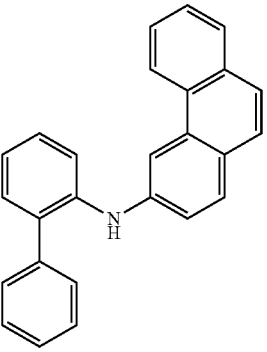 [SMILES: c1ccc(-c2ccccc2Nc2ccc3ccc4ccccc4c3c2)cc1] | 88 |
| 6q | 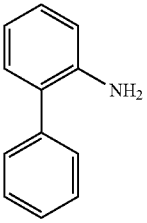<br>90-41-5 | 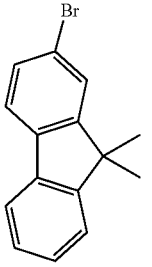<br>28320-31-2 | 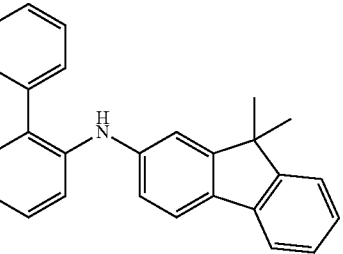 | 74 |

Example 7: Biphenyl-4-yl-(3'-bromobiphenyl-3-yl)-(9,9-dimethyl-9H-fluoren-2-yl)amine

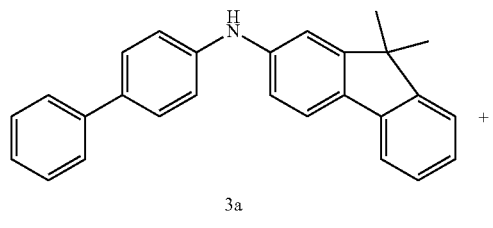

3a

+

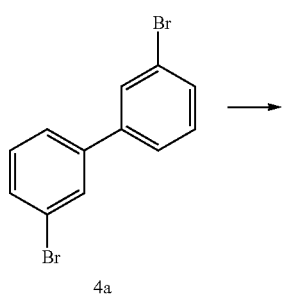

4a

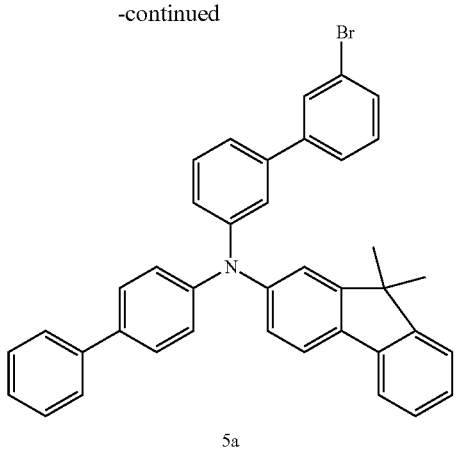

5a 29 g (80 mmol, 1.0 eq) of the intermediate 3a are dissolved together with 25 g (80 mmol, 1.0 eq) of 3,3'-dibromo-1,1'-biphenyl 4a (CAS 16400-51-4) in 600 ml of toluene and degassed for 30 minutes. Subsequently, 45 g (240 mmol, 3.0 eq) of sodium tert-butoxide, 890 mg (0.40 mmol, 0.050 eq) of palladium(II) acetate and 8 ml (8.0 mmol, 0.10 eq.) of a 1M tri-tert-butylphosphine solution are added. The mixture is heated under reflux overnight and, after the reaction has ended, filtered twice through alumina with toluene. After the solvent has been removed by rotary evaporator, the oil is dissolved in a little THF and introduced into heptane. The resultant solids are filtered off with suction and purified by means of hot extraction in heptane/toluene 1:1. 16.6 g (28 mmol, 35%) of the desired product 5a are obtained.

In an analogous manner, it is possible to obtain the following compounds:

| Ex. | Reactant 3 | Reactant 4 | Product | Yield [%] |
|---|---|---|---|---|
| 7a | 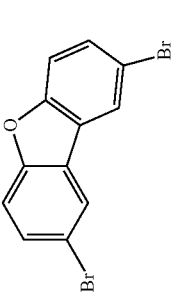 | 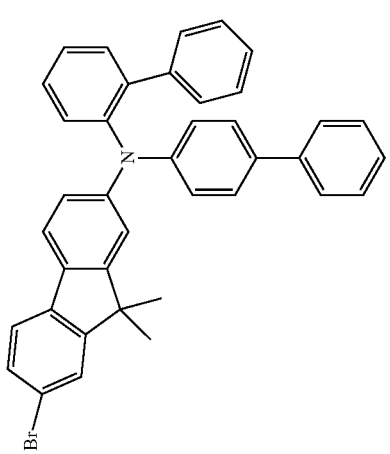28320-32-3 | 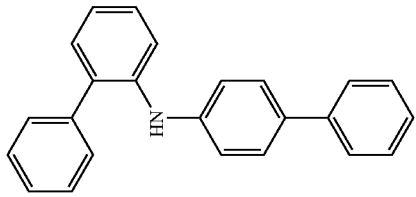 | 49 |
| 7b | 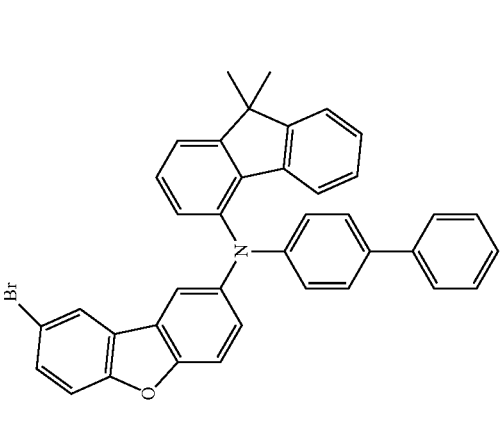 | 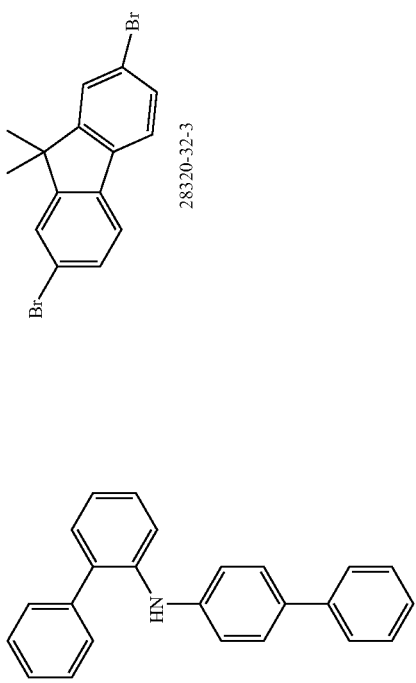10016-52-1 | 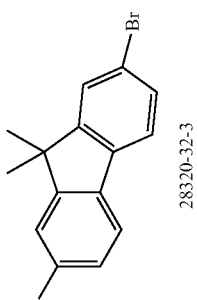 | 37 |

| Ex. | Reactant 3 | Reactant 4 | Product | Yield [%] |
|---|---|---|---|---|
| 7c | (dibenzofuran-phenyl-NH-biphenyl) | 3,3'-dibromobiphenyl  16400-51-4 | (triarylamine product) | 72 |
| 7d | (dibenzothiophene-phenyl-NH-biphenyl) | 6,6'-dibromo-2,2'-bipyridine  49669-22-9 | (triarylamine product) | 28 |

-continued
| Ex. | Reactant 3 | Reactant 4 | Product | Yield [%] |
|---|---|---|---|---|
| 7e | 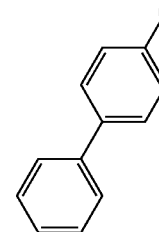 | 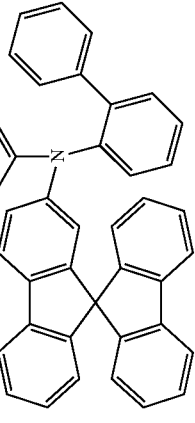
105946-82-5 | 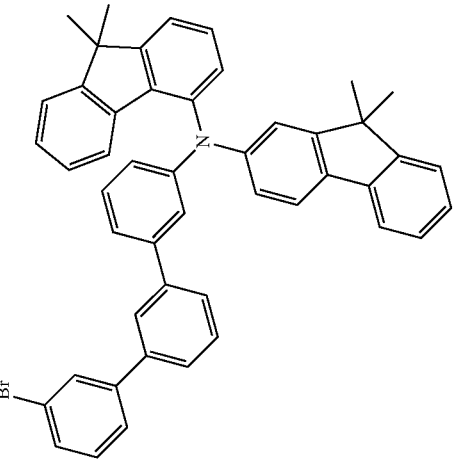 | 82 |
| 7f | 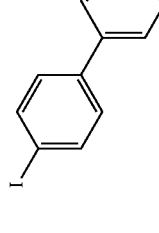 | 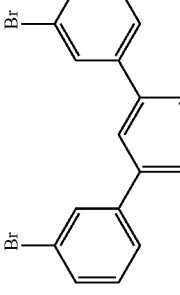
95962-62-2 | 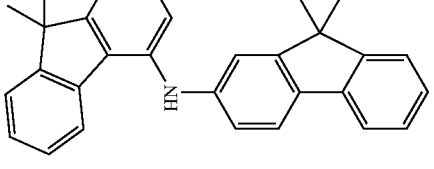 | 32 |

| Ex. | Reactant 3 | Reactant 4 | Product | Yield [%] |
|---|---|---|---|---|
| 7g | 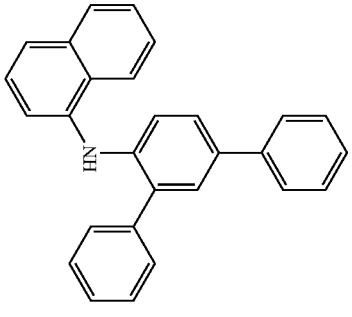 | 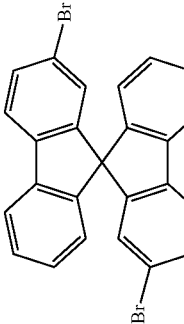 67665-47-8 | 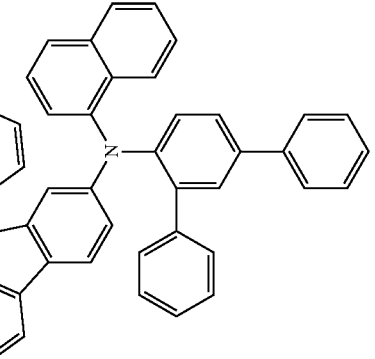 | 46 |
| 7h | 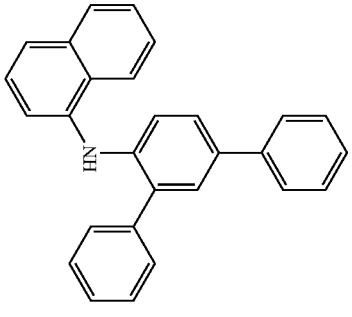 | 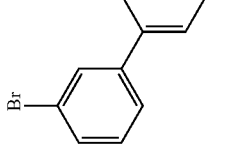 16400-51-4 | 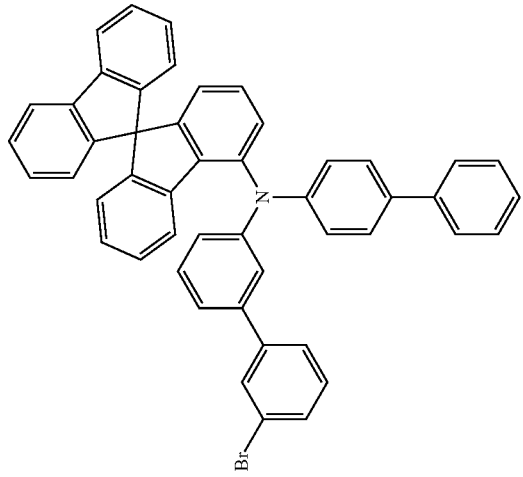 | 41 |

-continued
| Ex. | Reactant 3 | Reactant 4 | Product | Yield [%] |
|---|---|---|---|---|
| 7i | 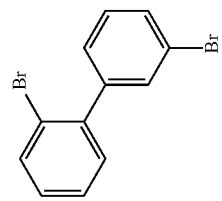 | 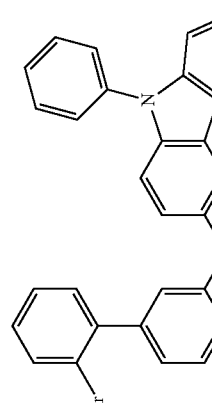 49602-90-6 | 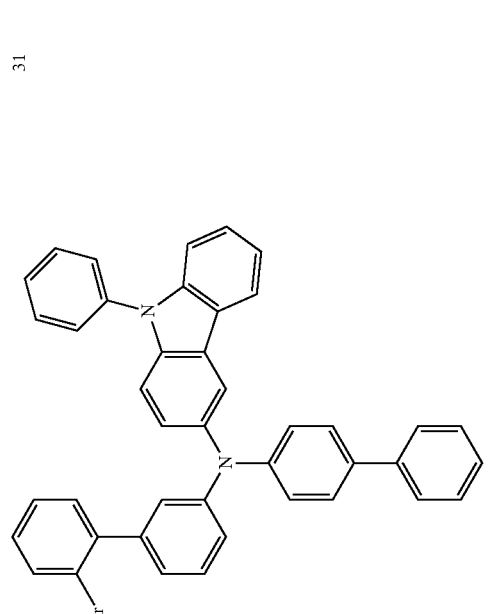 | 31 |
| 7j | 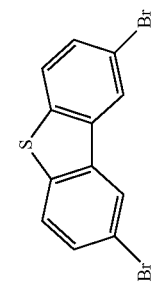 | 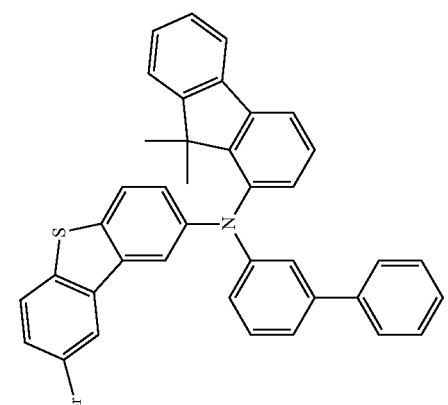 31574-87-5 | 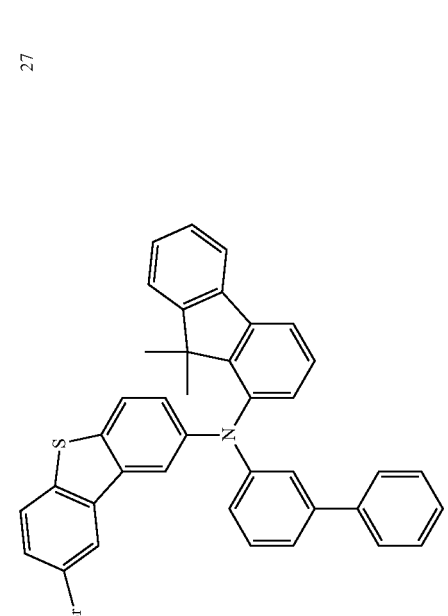 | 27 |

| Ex. | Reactant 3 | Reactant 4 | Product | Yield [%] |
|---|---|---|---|---|
| 7k | 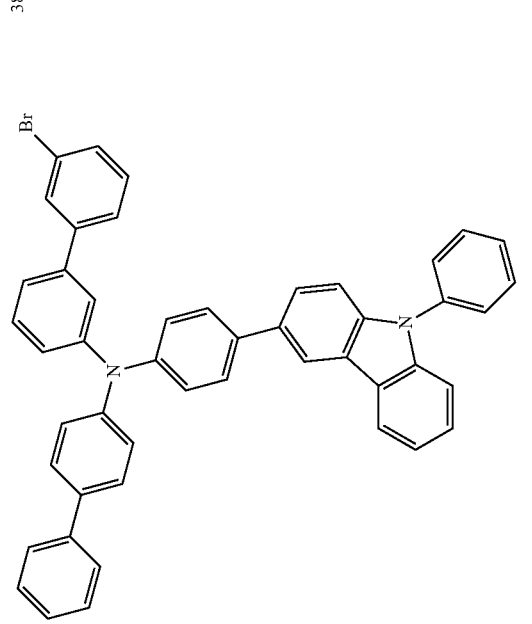 | 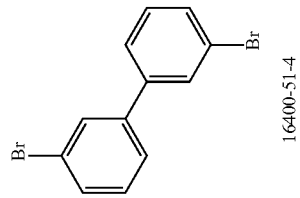 16400-51-4 | 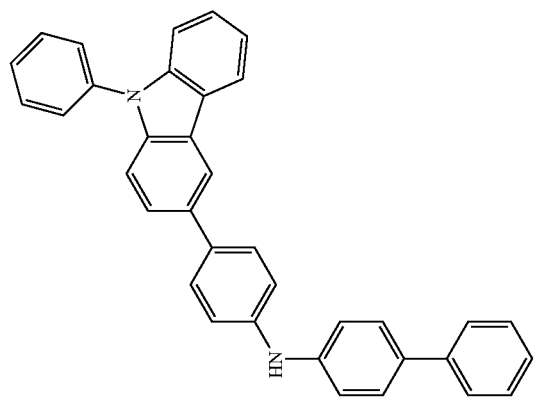 | 38 |

| Ex. | Reactant 3 | Reactant 4 | Product | Yield [%] |
|---|---|---|---|---|
| 71 | 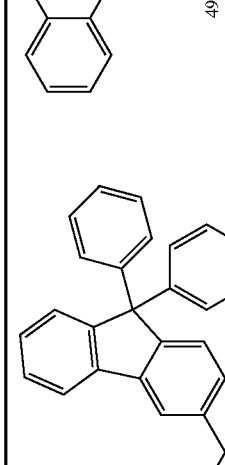 | 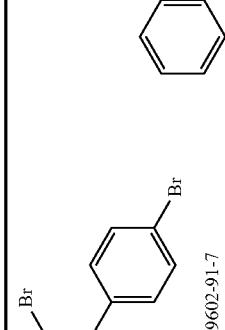  49602-91-7 | 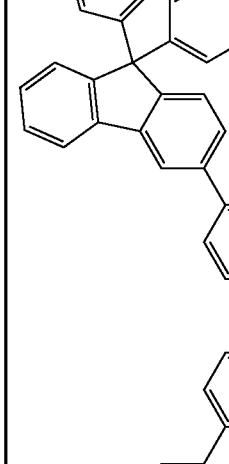 | 56 |

| Ex. | Reactant 3 | Reactant 4 | Product | Yield [%] |
|---|---|---|---|---|
| 7m | 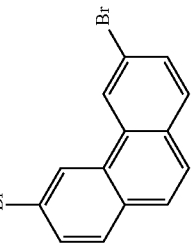 | 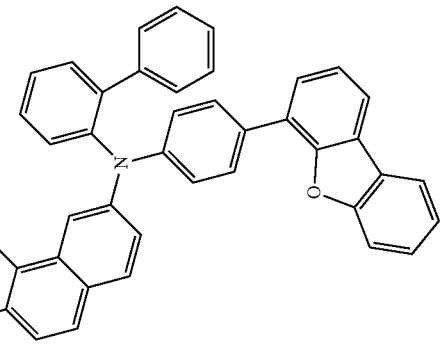 174735-02-5 | 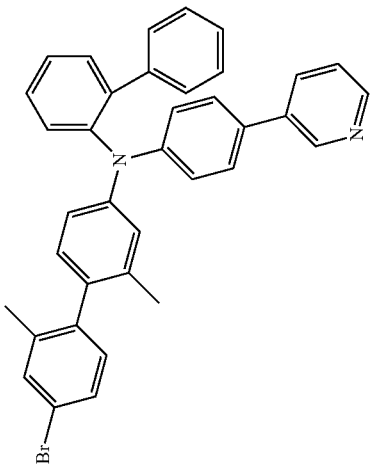 | 33 |
| 7n | 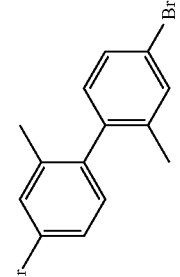 | 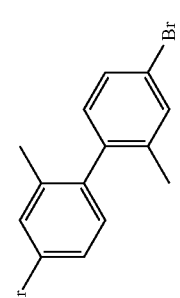 31458-17-0 | 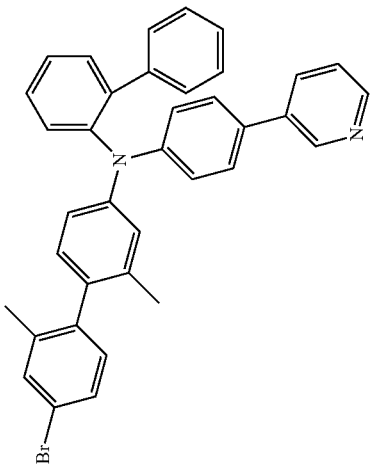 | 47 |

| Ex. | Reactant 3 | Reactant 4 | Product | Yield [%] |
|---|---|---|---|---|
| 7o | | 888041-37-0 | | 24 |
| 7p | | 626-05-1 | | 81 |

| Ex. | Reactant 3 | Reactant 4 | Product | Yield [%] |
|---|---|---|---|---|
| 7q | (9,9-dimethylfluoren-2-yl)(2-biphenylyl)amine | 3,3'-dibromobiphenyl (16400-51-4) | N-(3'-bromobiphenyl-3-yl)-N-(2-biphenylyl)-9,9-dimethylfluoren-2-amine | 57 |
| 7r | N,4'-diphenyl-[1,1'-biphenyl]-4-amine | 2,7-dibromo-9,9-dimethyl-10-phenyl-9,10-dihydroacridine (1333316-36-1) | 7-bromo-N,N-bis(biphenyl-4-yl)-9,9-dimethyl-10-phenyl-9,10-dihydroacridin-2-amine | 29 |

| Ex. | Reactant 3 | Reactant 4 | Product | Yield [%] |
|---|---|---|---|---|
| 7s | 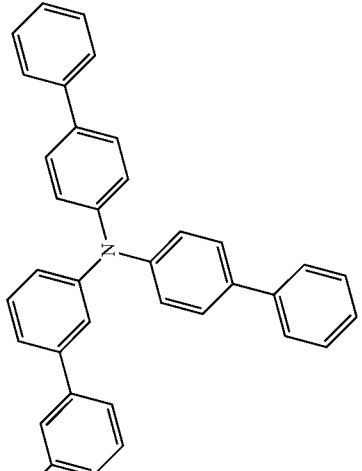 102113-98-4 | 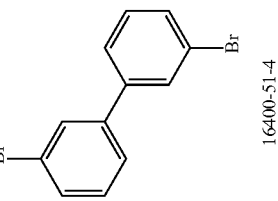 16400-51-4 | 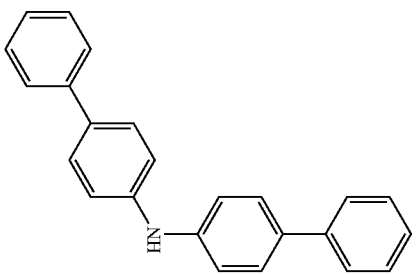 | 36 |

Example 8: Biphenyl-4-yl-(9,9-dimethyl-9H-fluoren-2-yl)-[3'-(4,4,5,5-tetramethyl-[1,3,2]dioxaborolan-2-yl)biphenyl-3-yl]amine

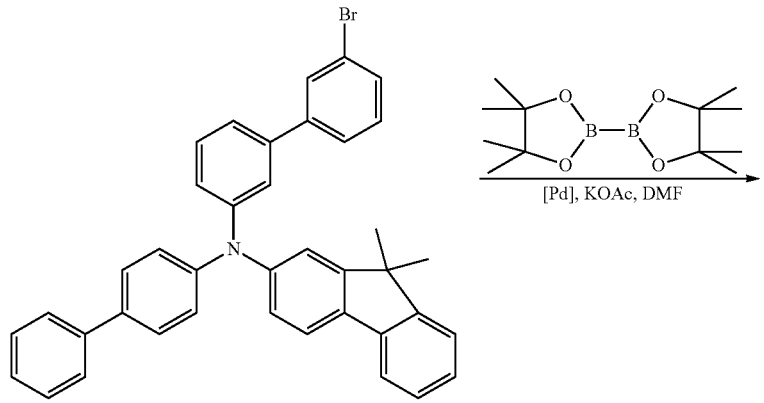

In a 500 ml flask, under protective gas, 16.6 g (28 mmol, 35%) of the bromide 5a are dissolved together with 8.5 g (34 mmol, 1.2 eq) of bis-(pinacolato)diborane (CAS 73183-34-3) in 120 ml of dry DMF and degassed for 30 minutes. Subsequently, 8.2 g (84 mmol, 3.0 eq) of potassium acetate and 690 mg (0.84 mmol, 3 mol %) of [1,1'-bis(diphenylphosphino)ferrocene]-dichloropalladium(II) complex are added together with dichloromethane (CAS 95464-05-4), and the mixture is heated at 90° C. overnight. After the reaction has ended, the mixture is diluted with 300 ml of toluene and the mixture is extracted with water. The solvent is removed by rotary evaporator and the solids obtained (14.7 g (23 mmol, 82%)) are dried. The boronic ester 6a is converted without further purification.

In an analogous manner, it is possible to obtain the following compounds:

| Ex. | Reactant 5 | Product 6 | Yield [%] |
|---|---|---|---|
| 8a | | | 88 |
| 8b | | | 81 |
| 8c | | | 75 |
| 8d | | | 67 |

| Ex. | Reactant 5 | Product 6 | Yield [%] |
|---|---|---|---|
| 8e | | | 79 |
| 8f | | | 93 |
| 8g | | | 44 |

-continued

| Ex. | Reactant 5 | Product 6 | Yield [%] |
|---|---|---|---|
| 8h | | | 87 |
| 8i | | | 28 |
| 8j | | | 35 |
| 8k | | | 77 |

| Ex. | Reactant 5 | Product 6 | Yield [%] |
|---|---|---|---|
| 8l | | | 38 |
| 8m | | | 55 |
| 8n | | | 41 |
| 8o | | | 67 |

-continued

| Ex. | Reactant 5 | Product 6 | Yield [%] |
|---|---|---|---|
| 8p | | | 82 |
| 8q | | | 91 |
| 8r | | | 87 |
| 8s | | | 96 |

Example 9
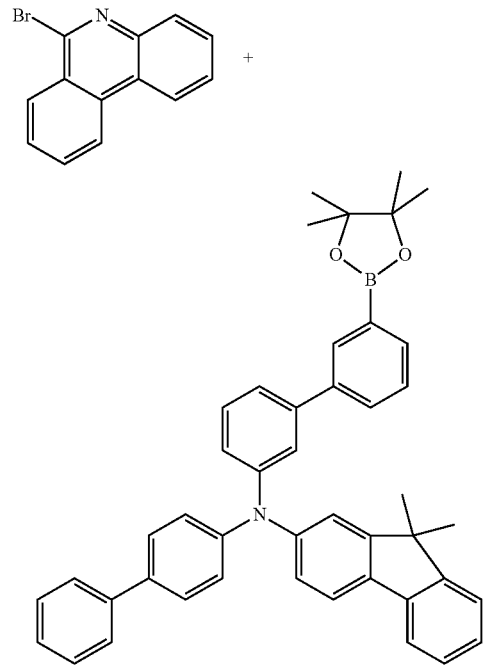 +
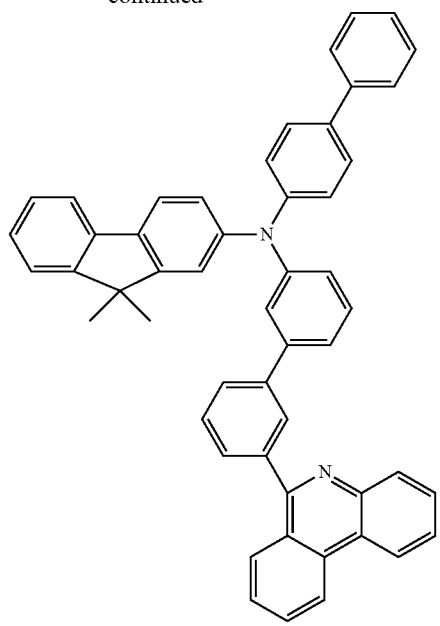
Analogously to Example 5, it is possible to prepare the following molecules:

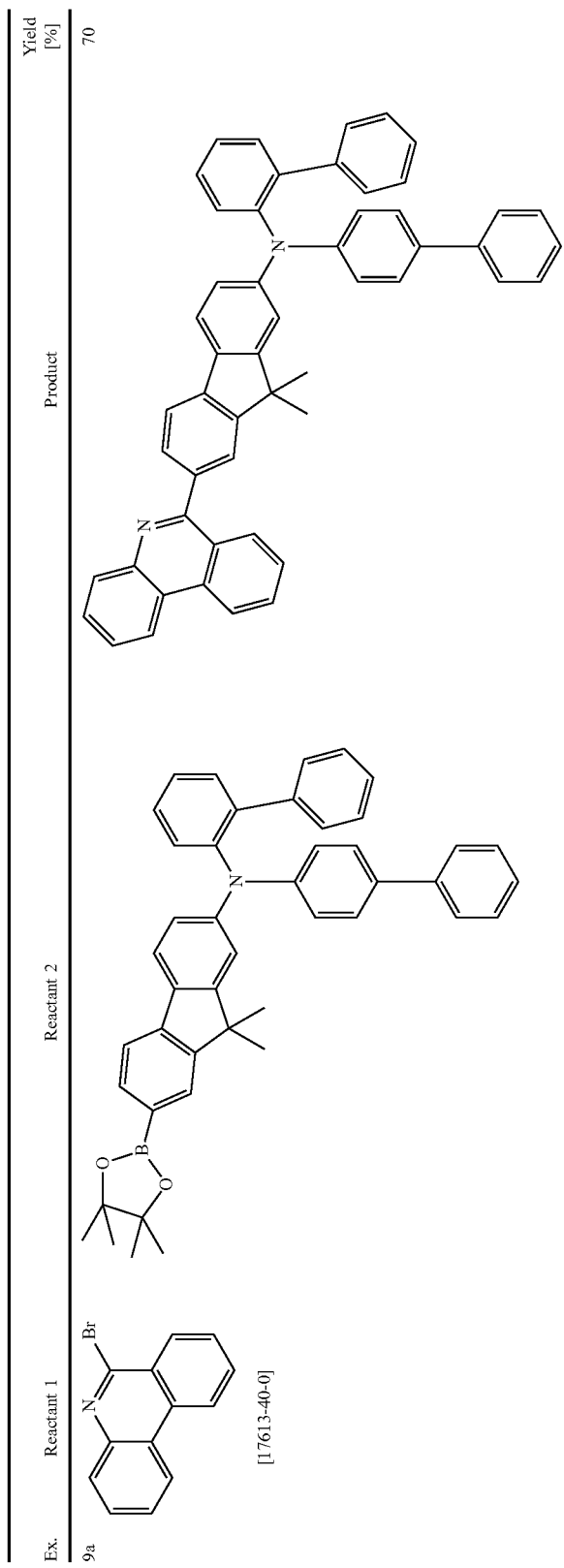

| Ex. | Reactant 1 | Reactant 2 | Product | Yield [%] |
|---|---|---|---|---|
| 9b | 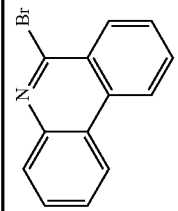 [17613-40-0] | 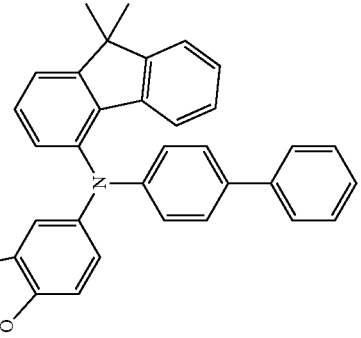 | 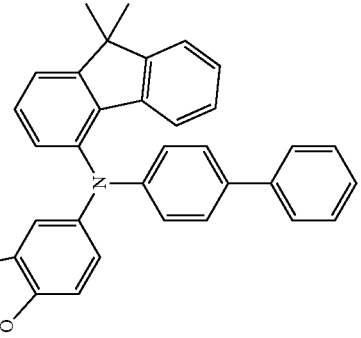 | 71 |

-continued
| Ex. | Reactant 1 | Reactant 2 | Product | Yield [%] |
|---|---|---|---|---|
| 9d | 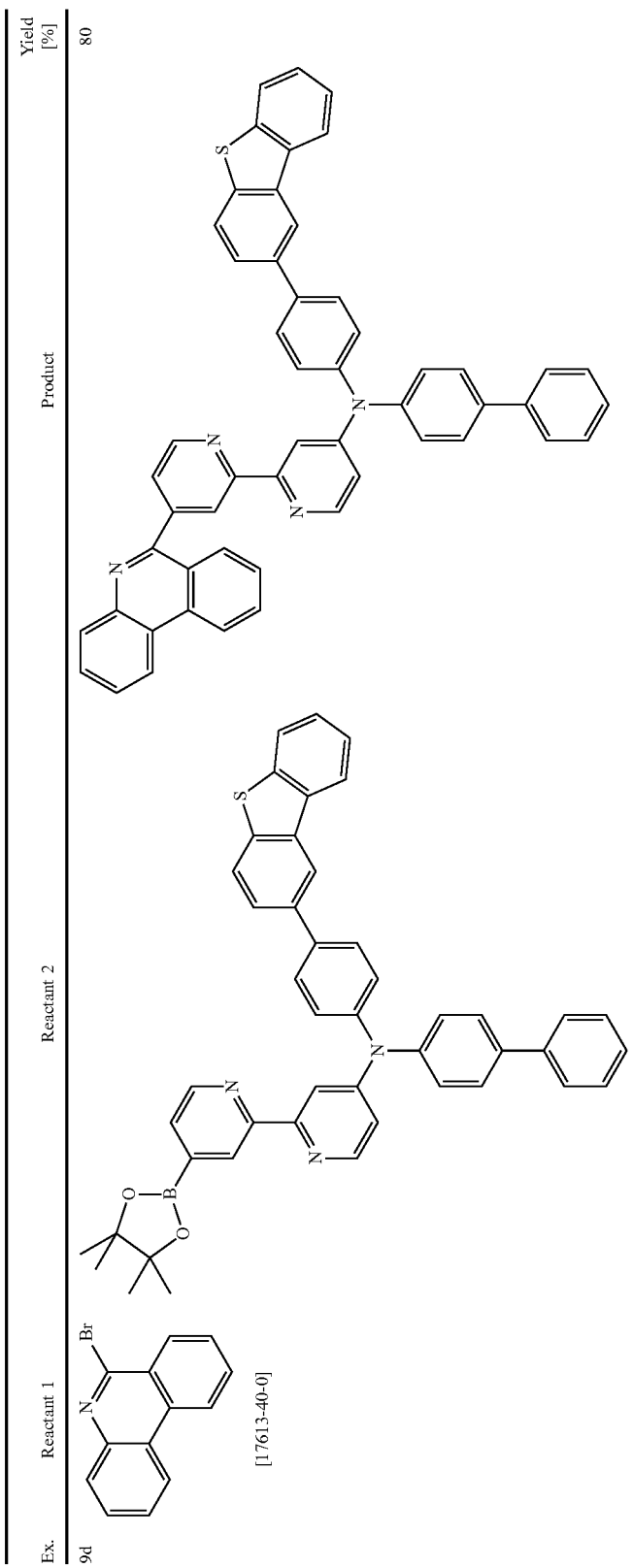 | | | 80 |

| Ex. | Reactant 1 | Reactant 2 | Product | Yield [%] |
|---|---|---|---|---|
| 9e | [structure, 17613-40-0] | [structure] | [structure] | 74 |

| Ex. | Reactant 1 | Reactant 2 | Product | Yield [%] |
|---|---|---|---|---|
| 9f | [17613-40-0] | | | 57 |
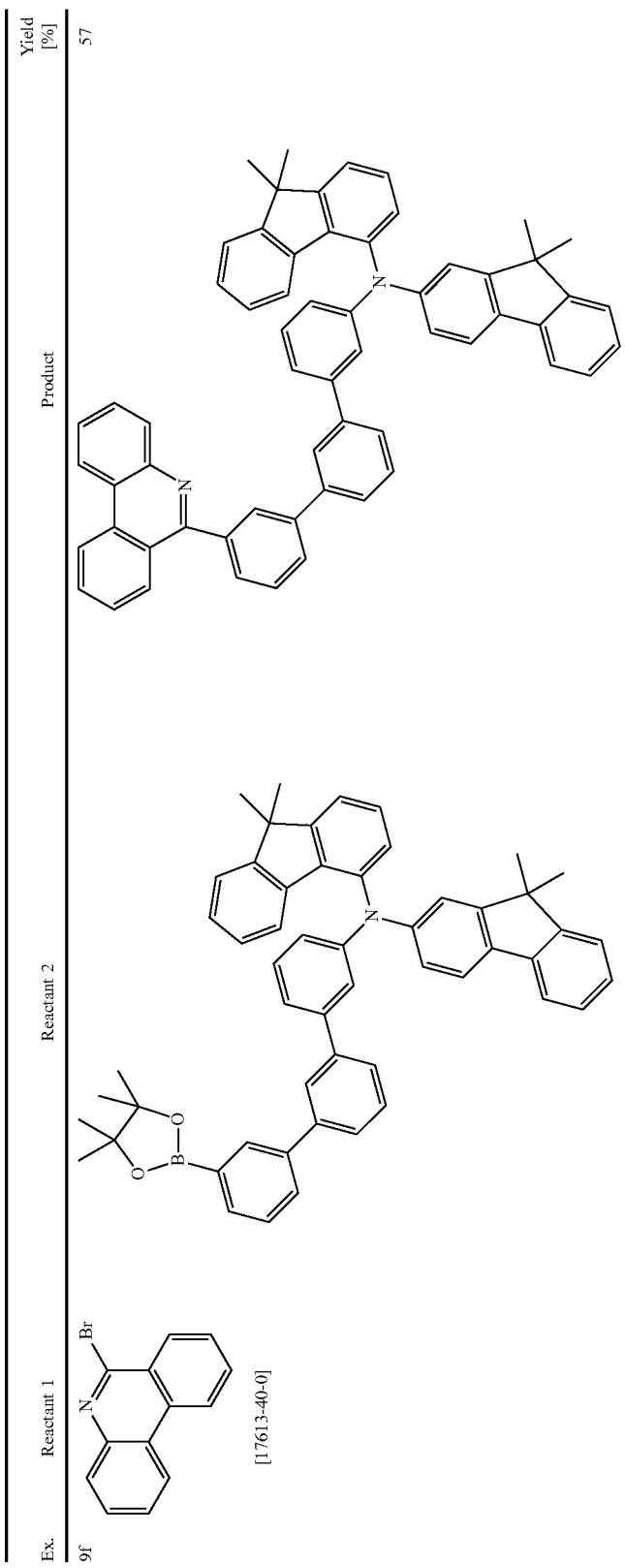

| Ex. | Reactant 1 | Reactant 2 | Product | Yield [%] |
|---|---|---|---|---|
| 9g | [17613-40-0] | | | 72 |

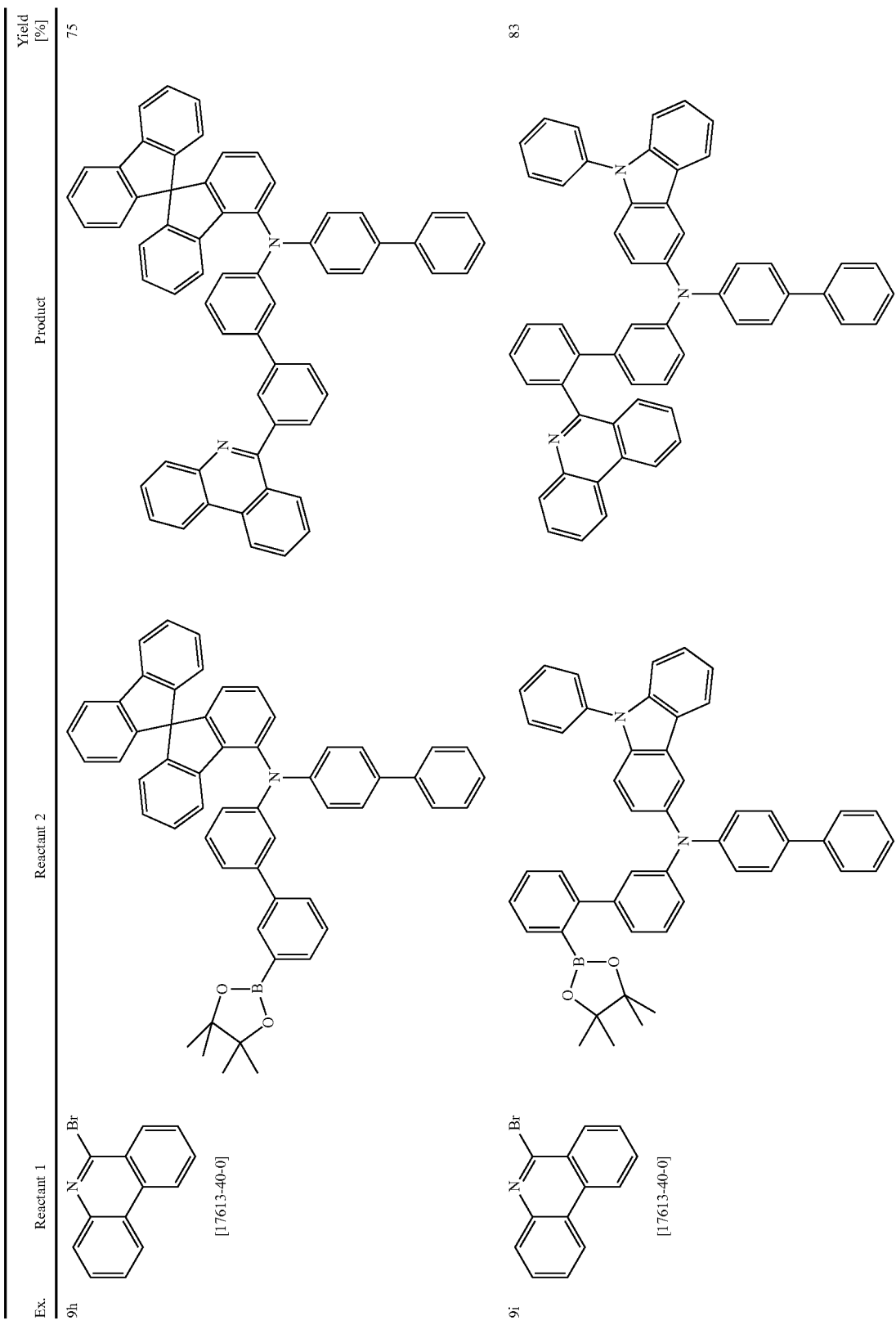

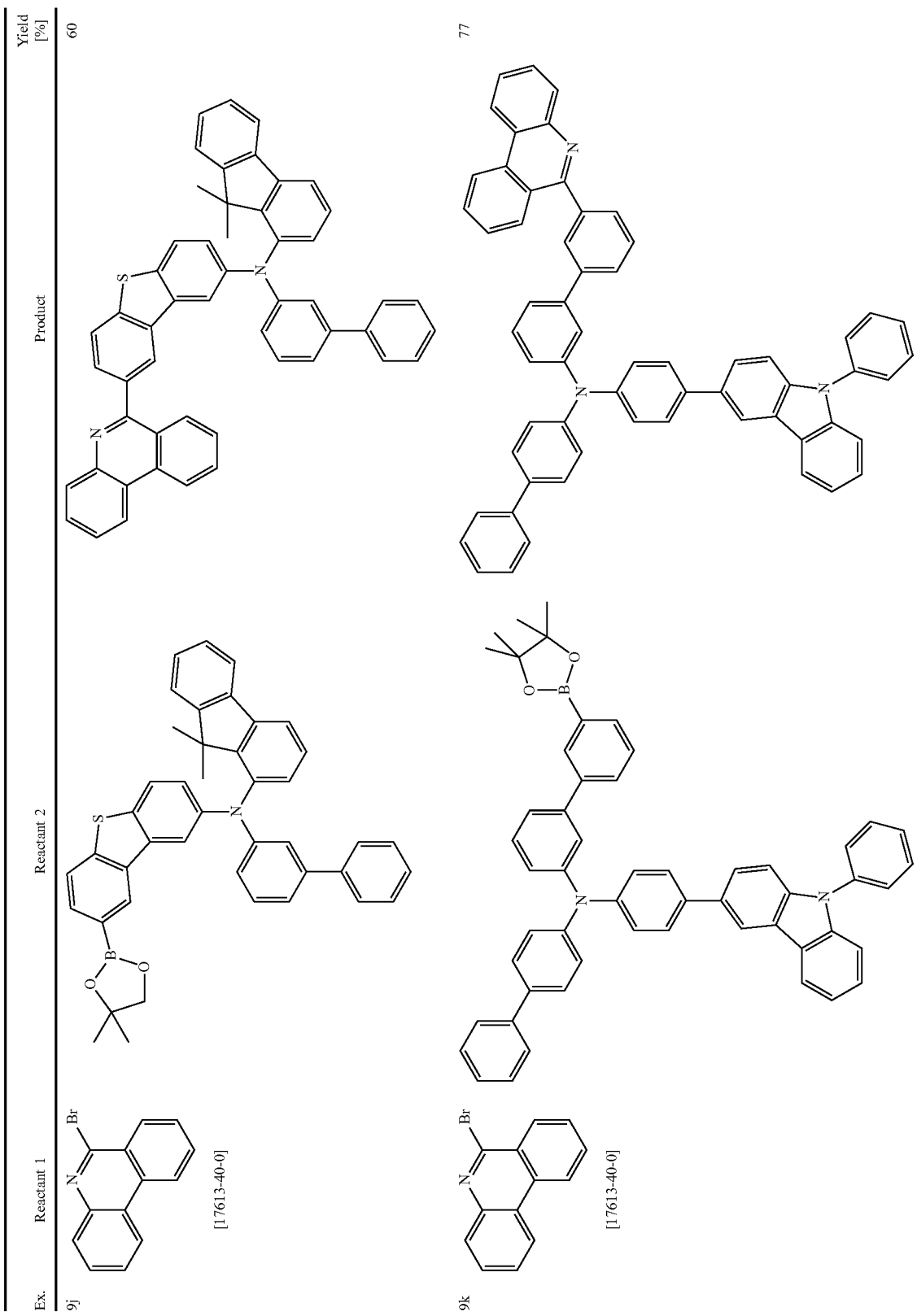

| Ex. | Reactant 1 | Reactant 2 | Product | Yield [%] |
|---|---|---|---|---|
| 91 | 6-bromophenanthridine [176133-40-0] | boronic ester intermediate with fluorene-triarylamine | phenanthridine-coupled fluorene-triarylamine product | 72 |

| Ex. | Reactant 1 | Reactant 2 | Product | Yield [%] |
|---|---|---|---|---|
| 9m | 6-bromophenanthridine [17613-40-0] | phenanthrene-boronic acid pinacol ester with N-biphenyl-N-(4-dibenzofuranyl-phenyl)amine substituent | phenanthridine-phenanthrene-N-biphenyl-N-(4-dibenzofuranyl-phenyl)amine product | 73 |

| Ex. | Reactant 1 | Reactant 2 | Product | Yield [%] |
|---|---|---|---|---|
| 9n | 6-bromophenanthridine [17613-40-0] | (boronate ester intermediate) | (coupled product) | 66 |

| Ex. | Reactant 1 | Reactant 2 | Product | Yield [%] |
|---|---|---|---|---|
| 9o | 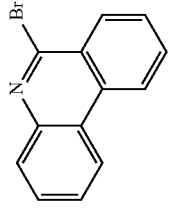 [17613-40-0] | 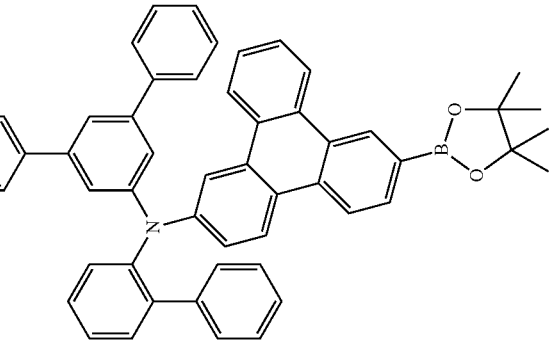 | 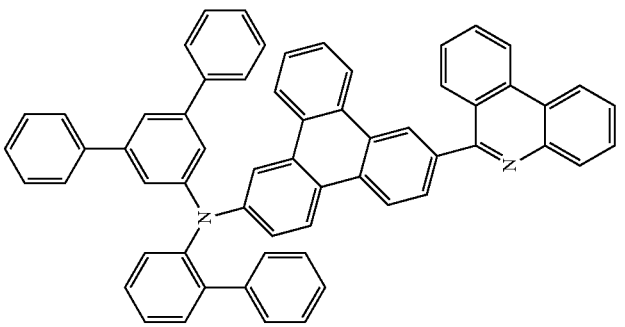 | 87 |
| 9p | 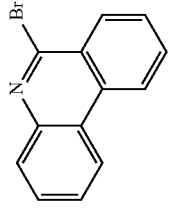 [17613-40-0] | 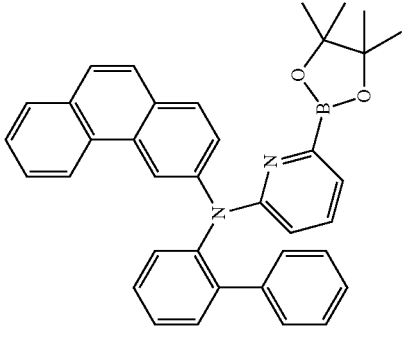 | 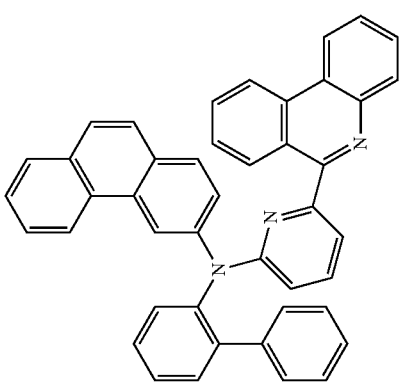 | 84 |

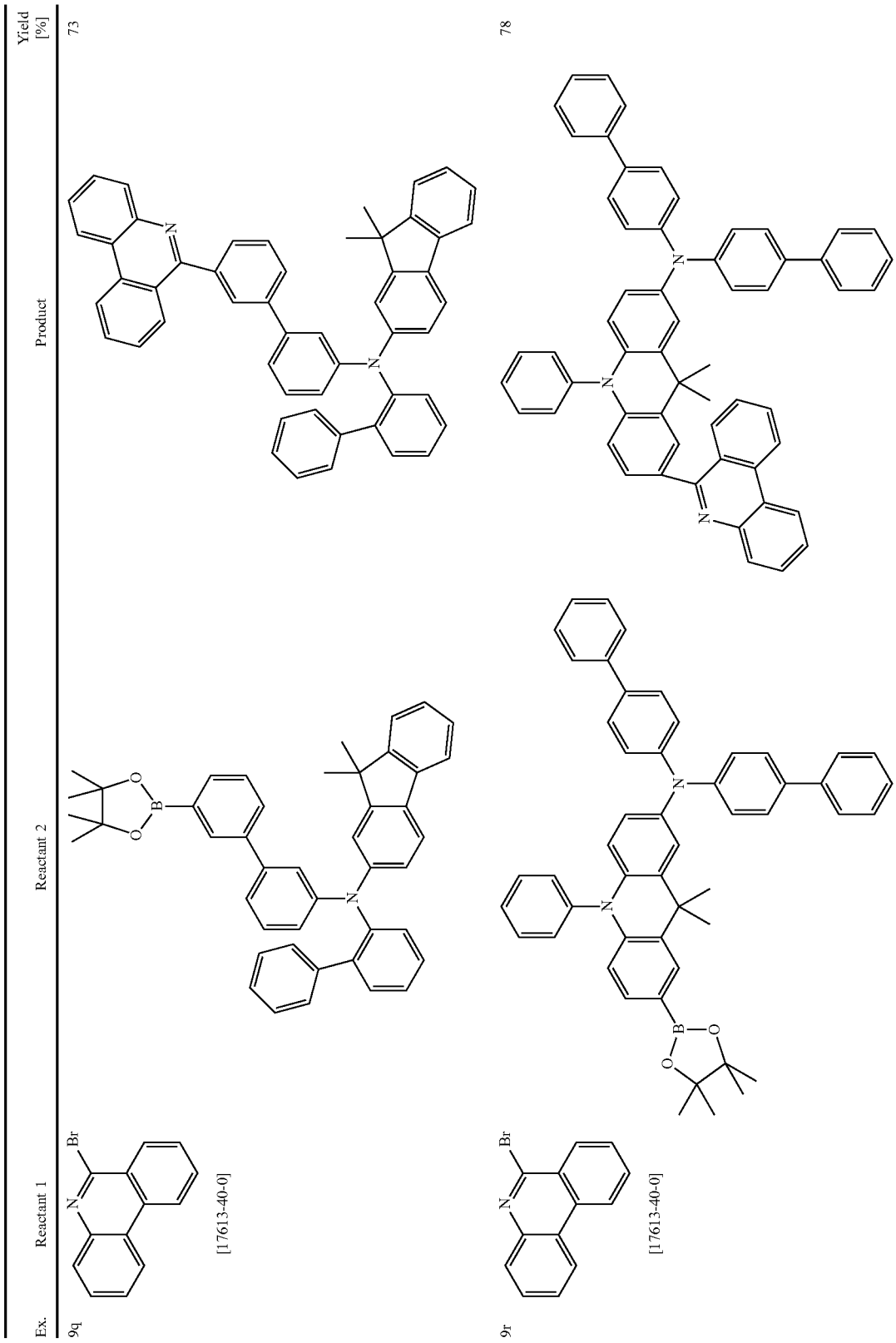

-continued
| Ex. | Reactant 1 | Reactant 2 | Product | Yield [%] |
|---|---|---|---|---|
| 9s | 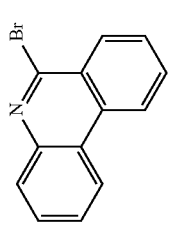 [17613-40-0] | 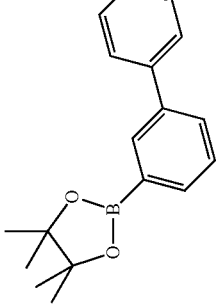 | 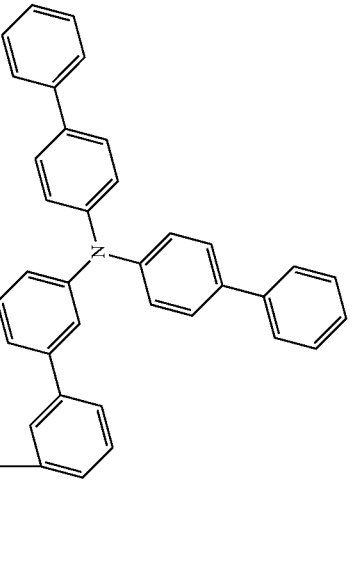 | 91 |
| 9t | 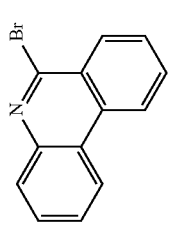 [17613-40-0] | 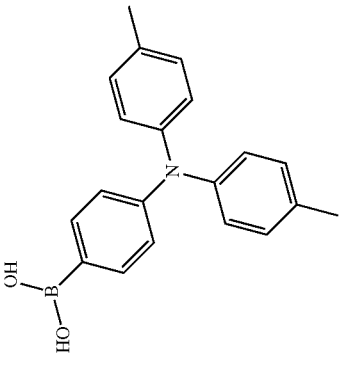 654067-65-9 | 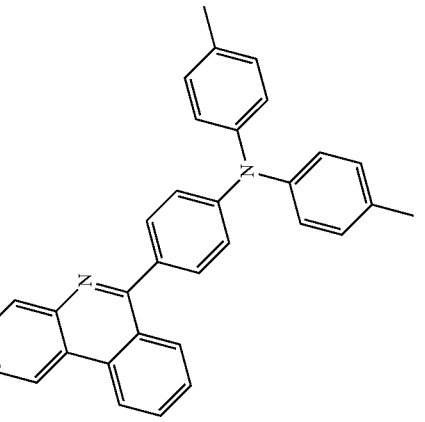 | 85 |

-continued

| Ex. | Reactant 1 | Reactant 2 | Product | Yield [%] |
|---|---|---|---|---|
| 9u | [17613-40-0] 6-bromophenanthridine | 4-(phenoxazin-10-yl)phenylboronic acid | 6-[4-(phenoxazin-10-yl)phenyl]phenanthridine | 79 |

Example 10: Biphenyl-4-yl-(9,9-dimethyl-9H-fluoren-2-yl)phenanthridin-6-ylamine

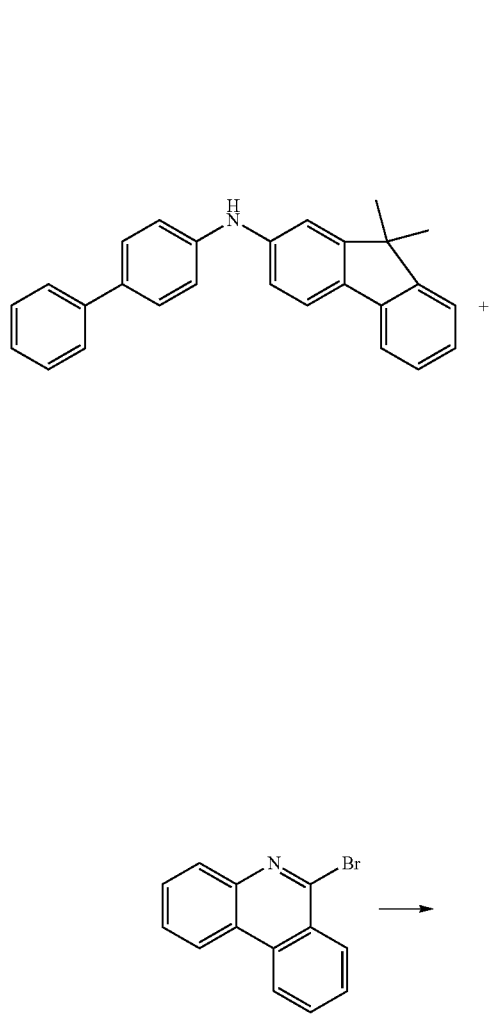

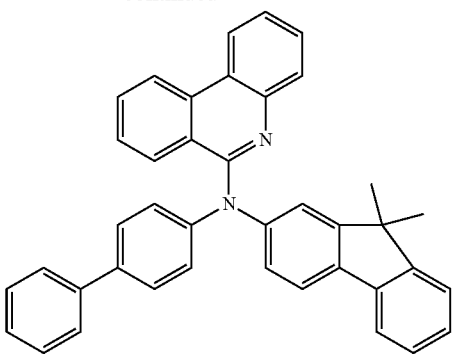

29 g (80 mmol, 1.0 eq) of biphenyl-4-yl-(9,9-dimethyl-9H-fluoren-2-yl)amine are dissolved together with 20 g (80 mmol, 1.0 eq) of 6-bromophenanthridine in 600 ml of toluene and degassed for 30 minutes. Subsequently, 45 g (240 mmol, 3.0 eq) of sodium tert-butoxide, 890 mg (0.40 mmol, 0.050 eq) of palladium(II) acetate and 8 ml (8.0 mmol, 0.10 eq.) of a 1M tri-tert-butylphosphine solution are added. The mixture is heated under reflux overnight and, after the reaction has ended, filtered twice through an alumina with toluene. After the solvent has been removed on a rotary evaporator, the oil is dissolved in a little THF and introduced into heptane. The product is purified via column chromatography on silica gel with toluene/heptane (1:2) and finally sublimed under high vacuum ($p=5\times10^{-7}$ mbar). 29 g (28 mmol, 69%) of the desired product with purity <99.9% are obtained.

In an analogous manner, it is possible to obtain the following compounds:

| Ex. | Reactant 1 | Reactant 2 | Product | Yield [%] |
|---|---|---|---|---|
| 10a | 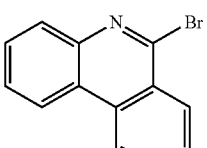 [17613-40-0] | 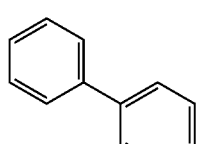 | 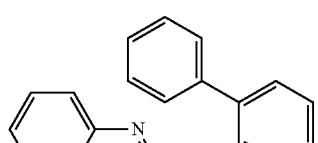 | 49% |

| Ex. | Reactant 1 | Reactant 2 | Product | Yield [%] |
|---|---|---|---|---|
| 10b | 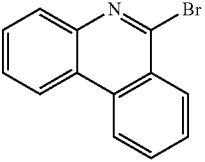 [17613-40-0] | 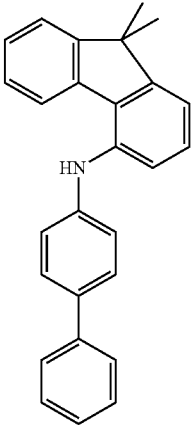 [SMILES: CC1(C)c2ccccc2-c2c(Nc3ccc(-c4ccccc4)cc3)cccc21] | 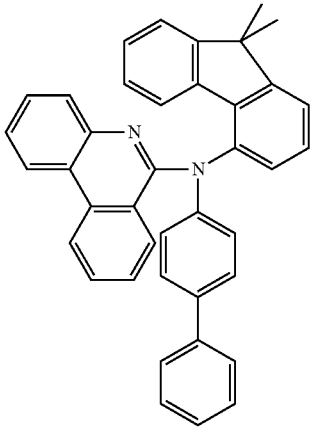 [SMILES: CC1(C)c2ccccc2-c2c(N(c3ccc(-c4ccccc4)cc3)c3nc4ccccc4c4ccccc34)cccc21] | 53 |
| 10c | 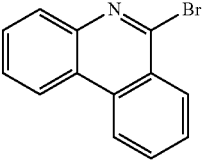 [17613-40-0] | 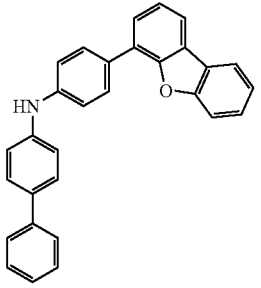 [SMILES: c1ccc(-c2ccc(Nc3ccc(-c4cccc5c4oc4ccccc45)cc3)cc2)cc1] | 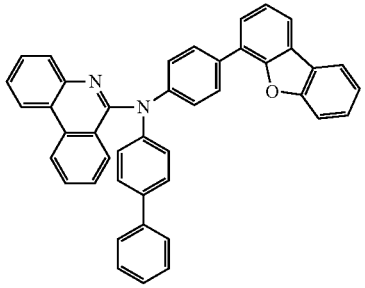 [SMILES: c1ccc(-c2ccc(N(c3ccc(-c4cccc5c4oc4ccccc45)cc3)c3nc4ccccc4c4ccccc34)cc2)cc1] | 68 |
| 10d | 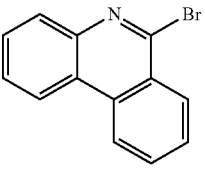 [17613-40-0] | 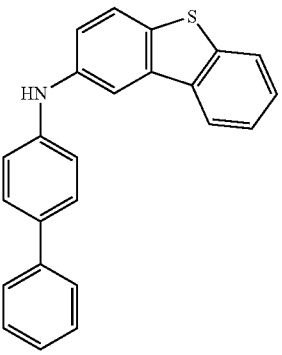 [SMILES: c1ccc(-c2ccc(Nc3ccc4sc5ccccc5c4c3)cc2)cc1] | 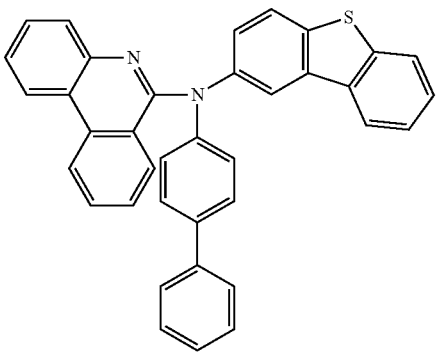 [SMILES: c1ccc(-c2ccc(N(c3ccc4sc5ccccc5c4c3)c3nc4ccccc4c4ccccc34)cc2)cc1] | 69 |
| 10e | 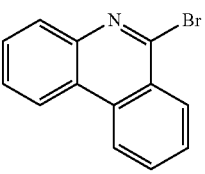 [17613-40-0] | 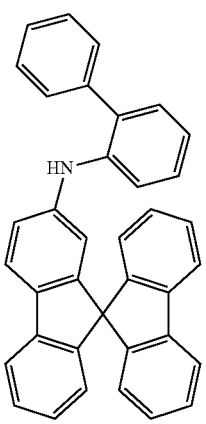 [SMILES: c1ccc(-c2ccccc2Nc2ccc3c(c2)C2(c4ccccc4-c4ccccc42)c2ccccc2-3)cc1] | 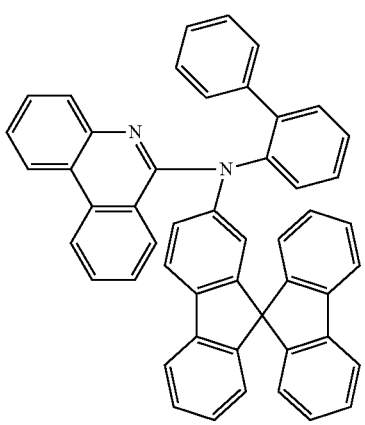 [SMILES: c1ccc(-c2ccccc2N(c2ccc3c(c2)C2(c4ccccc4-c4ccccc42)c2ccccc2-3)c2nc3ccccc3c3ccccc23)cc1] | 58 |

-continued

| Ex. | Reactant 1 | Reactant 2 | Product | Yield [%] |
|---|---|---|---|---|
| 10f | [17613-40-0] | | | 63 |
| 10g | [17613-40-0] | | | 65 |
| 10h | [17613-40-0] | | | 72 |

| Ex. | Reactant 1 | Reactant 2 | Product | Yield [%] |
|---|---|---|---|---|
| 10i | 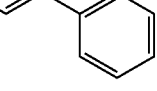 [17613-40-0] | 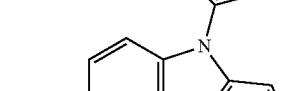 |  | 67 |
| 10m | 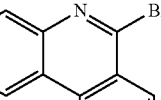 [17613-40-0] | 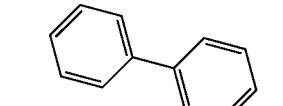 | 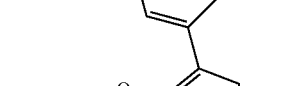 | 77 |
| 10p | 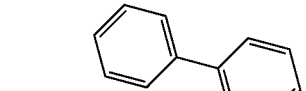 [17613-40-0] | 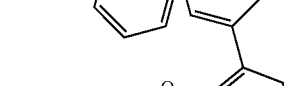 | 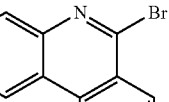 | 70 |

Example 11: Production of the OLEDs

In the examples 11 to 110 which follow (see tables 1 and 2), the data of various OLEDs are presented. Clean glass plaques (cleaning in a laboratory glass washer, detergent: Merck Extran) which have been coated with structured ITO (indium tin oxide) of thickness 50 nm are pretreated with UV ozone for 25 minutes (PR-100 UV ozone generator, from UVP) and, within 20 min, for improved processing, coated with 20 nm of PEDOT:PSS (poly(3,4-ethylenedioxy-thiophene) poly(styrenesulphonate), purchased as CLEV-IOS™ P VP AI 4083 from Heraeus Precious Metals GmbH Deutschland, spun on from aqueous solution) and then baked at 180° C. for 10 min. These coated glass plaques form the substrates to which the OLEDs are applied.

The OLEDs have the following basic layer structure: substrate/hole transport layer (HTL)/interlayer (IL)/electron blocker layer (EBL) emission layer (EML)/optional hale blacker layer (HBL)/electron transport layer (ETL) and finally a cathode. The cathode is formed by an aluminium layer of thickness 100 nm. The exact structure of the OLEDs can be found in Table 1. A reference such as "5a" in the table relates to the materials shown in the tables for examples 4-10. The further materials required for production of the OLEDs are shown in table 3.

All materials are applied by thermal vapour deposition in a vacuum chamber. The emission layer always consists of at least one matrix material (host material) and an emitting dopant (emitter) which is admixed with the matrix material(s) by coevaporation in a particular proportion by volume. Details given in such a form as IC2:5c:TEG1 (60%:30%:10%) here mean that the material IC2 is present in the layer in a proportion by volume of 60%, 5c in a proportion of 30% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of the luminance, calculated from current-voltage-luminance characteristics (IUL characteristics) assuming Lambertian radiation characteristics, and the lifetime are determined. The electroluminescence spectra are determined at a luminance of 1000 cd/m$^2$ and these are used to calculate the CIE 1931 x and y colour coordinates. The FIGURE U1000 in Table 2 refers to the voltage which is required for a luminance of 1000 cd/m$^2$. SE1000 and LE1000 refer respectively to the current efficiency and power efficiency that are attained at 1000 cd/m$^2$. Finally, EQE1000 refers to the external quantum efficiency at an operating luminance of 1000 cd/m$^2$.

The data of the various OLEDs are summarized in table 2.

TABLE 1

Structure of the OLEDs

| Ex. | HTL thickness | IL thickness | EBL thickness | EML thickness | HBL thickness | ETL thickness |
|---|---|---|---|---|---|---|
| I1 | SpA1 70 nm | HATCN 5 nm | SpMA1 90 nm | IC1:TEG1 (90%:10%) 30 nm | IC1 10 nm | 5r1:LiQ (50%:50%) 30 nm |

TABLE 1-continued

Structure of the OLEDs

| Ex. | HTL thickness | IL thickness | EBL thickness | EML thickness | HBL thickness | ETL thickness |
|---|---|---|---|---|---|---|
| I2 | SpA1 70 nm | HATCN 5 nm | SpMA1 90 nm | 5r1:TEG1 (90%:15%) 30 nm | IC1 10 nm | ST1:LiQ (50%:50%) 30 nm |
| I3 | SpA1 90 nm | HATCN 5 nm | SpMA1 130 nm | 5r1:TER1 (90%:10%) 40 nm | — | ST1:LiQ (50%:50%) 40 nm |
| I4 | SpA1 70 nm | HATCN 5 nm | SpMA1 90 nm | IC2:5a:TEG1 (60%:30%:10%) 30 nm | IC1 10 nm | ST1:LiQ (50%:50%) 30 nm |
| I5 | SpA1 70 nm | HATCN 5 nm | SpMA1 90 nm | IC2:5c:TEG1 (60%:30%:10%) 30 nm | IC1 10 nm | ST1:LiQ (50%:50%) 30 nm |
| I6 | SpA1 70 nm | HATCN 5 nm | SpMA1 90 nm | IC2:5i:TEG1 (45%:45%:10%) 30 nm | ST1 10 nm | ST1:LiQ (50%:50%) 30 nm |
| I7 | SpA1 70nm | HATCN 5nm | 9 90 nm | IC2:TEG1 (90%:10%) 30 nm | IC1 10 nm | ST1:LiQ (50%:50%) 30 nm |
| I8 | SpA1 70 nm | HATCN 5 nm | 9j 90 nm | IC1:TEG1 (90%:10%) 30 nm | IC1 10 nm | ST1:LiQ (50%:50%) 30 nm |
| I9 | SpA1 70 nm | HATCN 5 nm | 9s 90 nm | IC1:TEG1 (90%:10%) 30 nm | IC1 10 nm | ST1:LiQ (50%:50%) 30nm |
| I10 | SpA1 70 nm | HATCN 5 nm | SpMA1 90 nm | IC1:9c:TEG1 (55%:35%:10%) 30 nm | IC1 10 nm | ST1:LiQ (50%:50%) 30 nm |

TABLE 2

Data of the OLEDs

| Ex. | U1000 (V) | SE1000 (cd/A) | LE1000 (lm/W) | EQE 1000 | CIE x/y at 1000 cd/m$^2$ |
|---|---|---|---|---|---|
| I1 | 4.8 | 55 | 36 | 15.3% | 0.34/0.62 |
| I2 | 3.6 | 57 | 49 | 15.8% | 0.33/0.63 |
| I3 | 4.9 | 12.2 | 7.8 | 13.2% | 0.67/0.33 |
| I4 | 3.5 | 55 | 49 | 15.4% | 0.33/0.62 |
| I5 | 3.7 | 50 | 42 | 13.7% | 0.33/0.63 |
| I6 | 3.2 | 57 | 55 | 15.9% | 0.34/0.62 |
| I7 | 3.3 | 47 | 45 | 13.3% | 0.34/0.62 |
| I8 | 3.4 | 60 | 55 | 16.8% | 0.34/0.62 |
| I9 | 3.5 | 61 | 55 | 17.2% | 0.34/0.62 |
| I10 | 3.4 | 64 | 59 | 18.0% | 0.34/0.62 |

TABLE 3

Structural formulae of the materials for the OLEDs

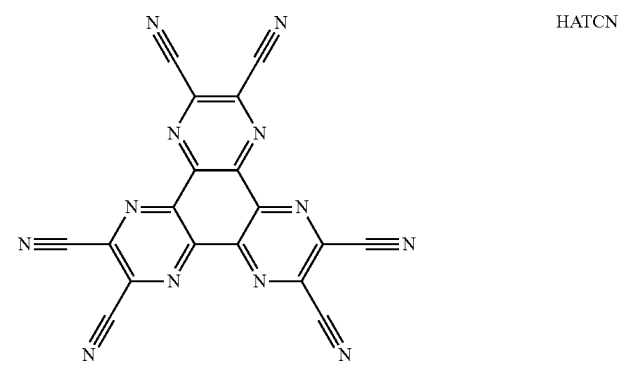

HATCN

TABLE 3-continued
Structural formulae of the materials for the OLEDs
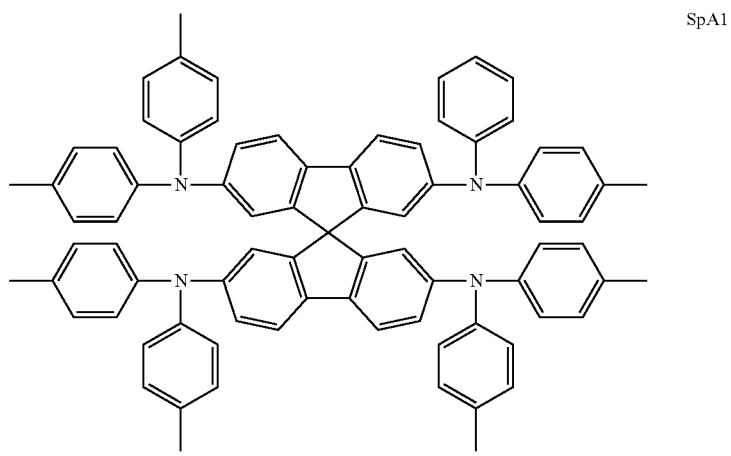
SpA1
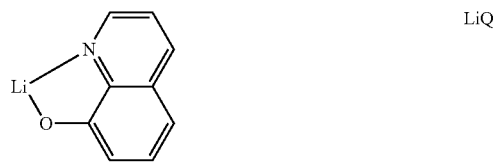
LiQ
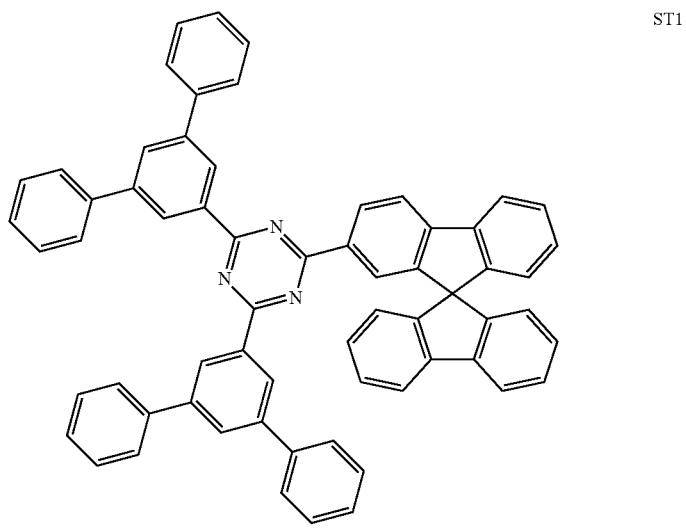
ST1
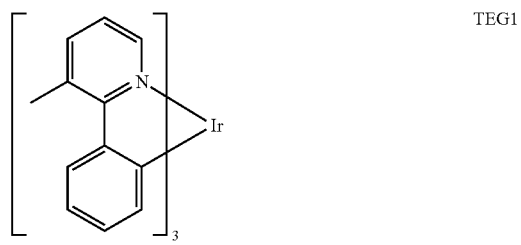
TEG1

TABLE 3-continued
Structural formulae of the materials for the OLEDs
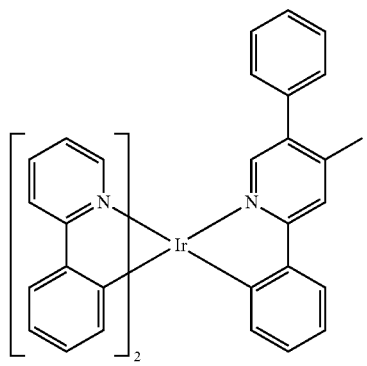
TEG2
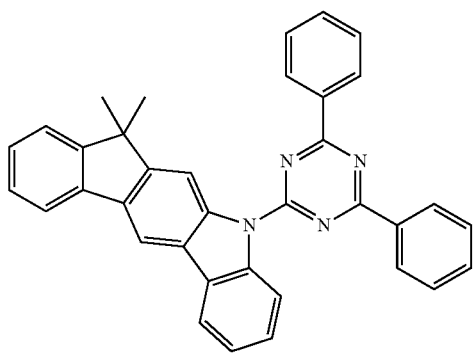 [SMILES: CC1(C)c2ccccc2-c2cc3c4ccccc4n(-c4nc(-c5ccccc5)nc(-c5ccccc5)n4)c3cc21]
IC1
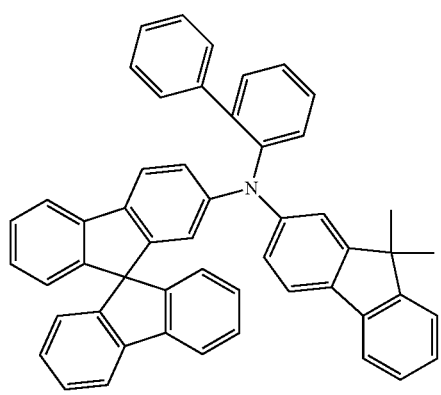 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
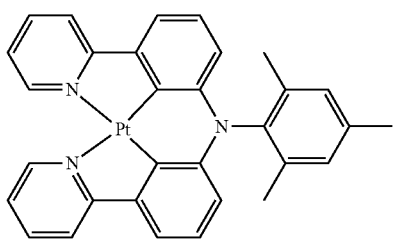
TER1

TABLE 3-continued
Structural formulae of the materials for the OLEDs
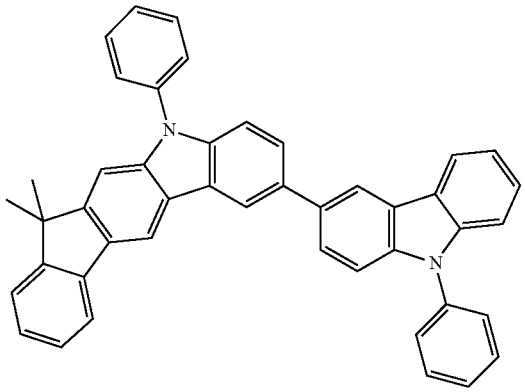 [SMILES: CC1(C)c2ccccc2-c2cc3c4cc(-c5ccc6c(c5)c5ccccc5n6-c5ccccc5)ccc4n(-c4ccccc4)c3cc21]
BIC1
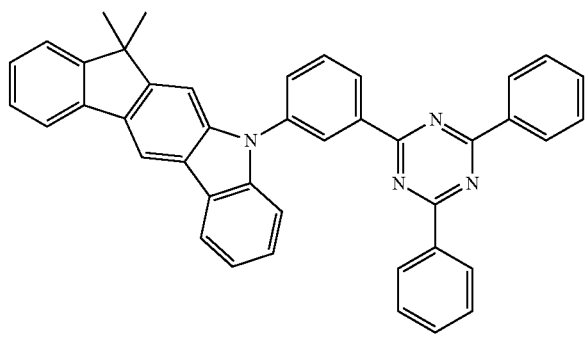 [SMILES: CC1(C)c2ccccc2-c2cc3c4ccccc4n(-c4cccc(-c5nc(-c6ccccc6)nc(-c6ccccc6)n5)c4)c3cc21]
IC2
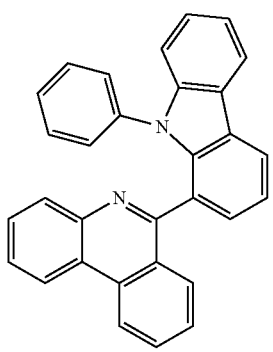 [SMILES: c1ccc(-n2c3ccccc3c3cccc(-c4nc5ccccc5c5ccccc45)c32)cc1]
5a
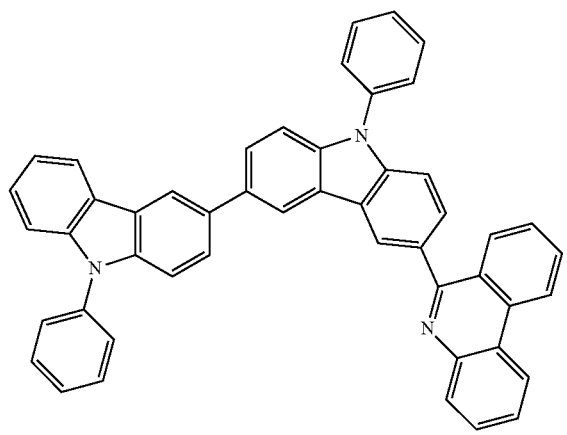 [SMILES: c1ccc(-n2c3ccccc3c3cc(-c4ccc5c(c4)c4cc(-c6nc7ccccc7c7ccccc67)ccc4n5-c4ccccc4)ccc32)cc1]
5c 245 246
TABLE 3-continued
Structural formulae of the materials for the OLEDs
5i
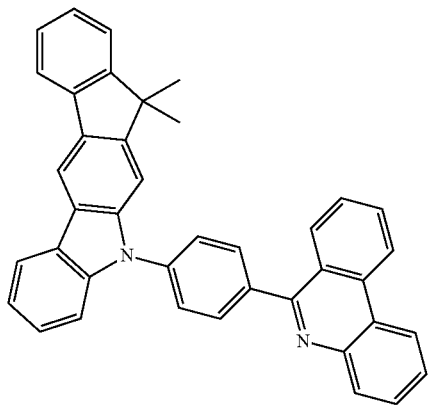 [SMILES: CC1(C)c2ccccc2-c2cc3c4ccccc4n(-c4ccc(-c5nc6ccccc6c6ccccc56)cc4)c3cc21]
5r1
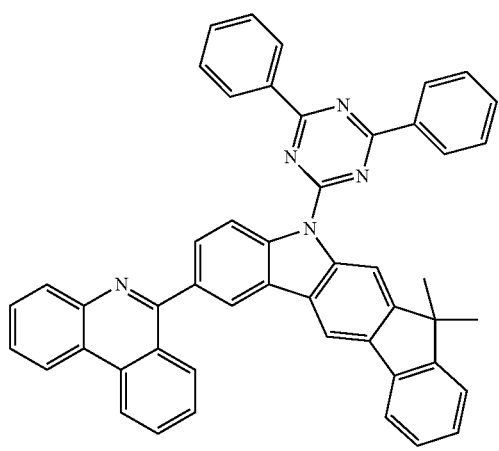 [SMILES: CC1(C)c2ccccc2-c2cc3c4cc(-c5nc6ccccc6c6ccccc56)ccc4n(-c4nc(-c5ccccc5)nc(-c5ccccc5)n4)c3cc21]
9
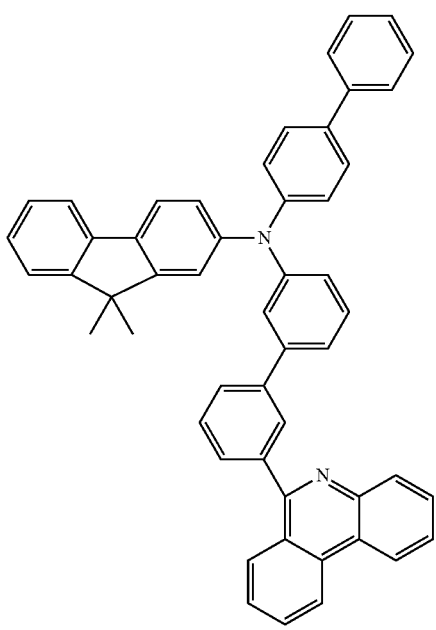 [SMILES: CC1(C)c2ccccc2-c2ccc(N(c3ccc(-c4ccccc4)cc3)c3cccc(-c4cccc(-c5nc6ccccc6c6ccccc56)c4)c3)cc21]

TABLE 3-continued
Structural formulae of the materials for the OLEDs
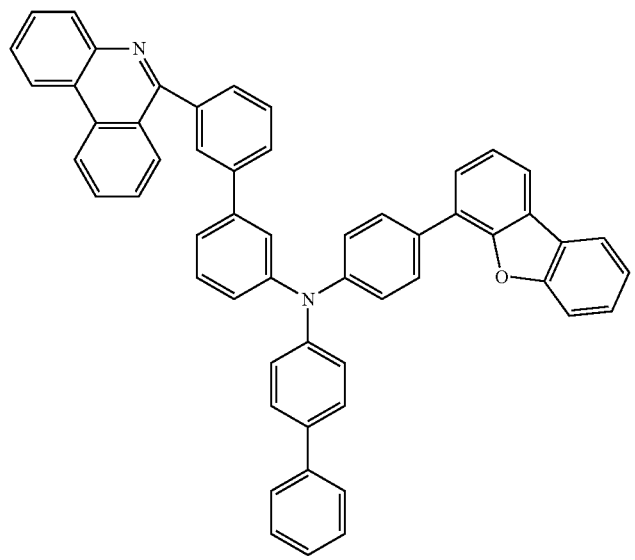 [SMILES: c1ccc(-c2ccc(N(c3ccc(-c4cccc5c4oc4ccccc45)cc3)c3cccc(-c4cccc(-c5nc6ccccc6c6ccccc56)c4)c3)cc2)cc1]
9c
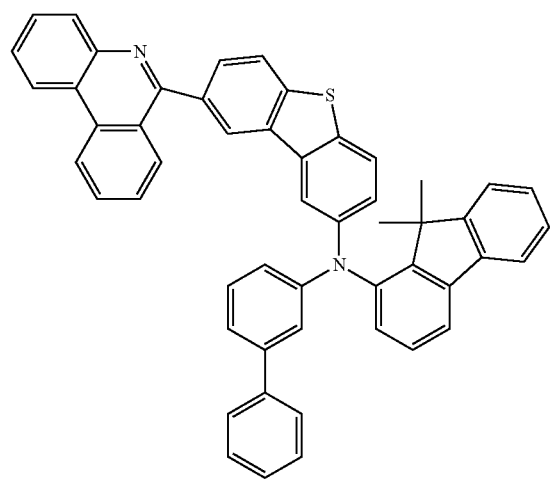 [SMILES: CC1(C)c2ccccc2-c2cccc(N(c3cccc(-c4ccccc4)c3)c3ccc4sc5ccc(-c6nc7ccccc7c7ccccc67)cc5c4c3)c21]
9j
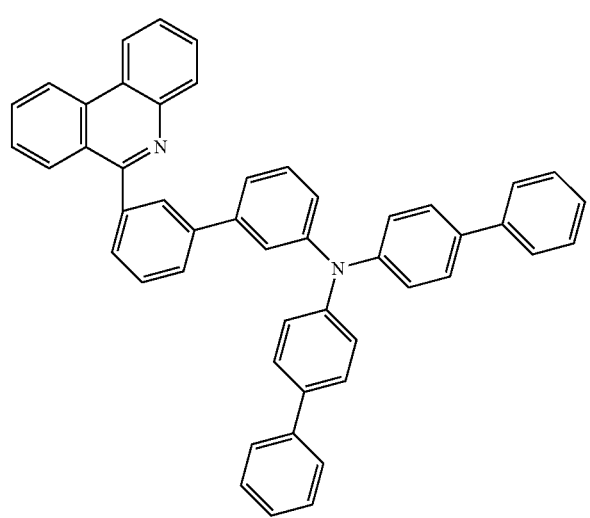 [SMILES: c1ccc(-c2ccc(N(c3ccc(-c4ccccc4)cc3)c3cccc(-c4cccc(-c5nc6ccccc6c6ccccc56)c4)c3)cc2)cc1]
9s

The invention claimed is:

1. An organic electroluminescent device comprising at least one compound of formula (1) used as matrix material for a fluorescent or phosphorescent compound in an emitting layer and/or in an electron blocker layer

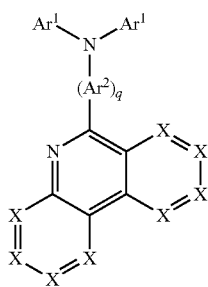

Formula (1)

where the symbols and indices used are as follows:

$Ar^1$ are the same or different at each instance and are an aromatic or heteroaromatic ring system which has 6 to 60 aromatic ring atoms and may in each case also be substituted by one or more $R^2$ radicals, where, in the case that q>0, at least the two $Ar^1$ may be joined and/or $Ar^1$ may be joined to $Ar^2$ via at least one bridge K;

K is the same or different at each instance and is a single bond or a bivalent bridge selected from $N(R^2)$, $B(R^2)$, O, C=O, $C(R^2)_2$, $Si(R^2)_2$, and S;

$Ar^2$ is the same or different at each instance and is a bivalent aromatic or heteroaromatic ring system which has 5 to 40 aromatic ring atoms and may be substituted by one or more $R^2$ radicals;

X is the same or different at each instance and is N or $CR^1$;

$R^1$ is the same or different at each instance and is H, D, F, Cl, Br, I, CHO, C(=O)Ar, P(=O)(Ar)$_2$, S(=O)Ar, S(=O)$_2$Ar, CN, NO$_2$, Si(R$^2$)$_3$, B(OR$^2$)$_2$, OSO$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by C≡C, Si(R$^2$)$_2$, Ge(R$^2$)$_2$, Sn(R$^2$)$_2$, C=O, C=S, C=Se, P(=O)(R$^2$), SO, SO$_2$, O, S or CONR$^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents may also together form a mono- or polycyclic, aliphatic or aromatic ring system;

Ar is the same or different at each instance and is an aromatic or heteroaromatic ring system which has 6 to 60 aromatic ring atoms and may in each case also be substituted by one or more $R^2$ radicals;

$R^2$ is the same or different at each instance and is H, D, F, Cl, Br, I, CHO, C(=O)R$^3$, P(=O) (R$^3$)$_2$, S(=O) R$^3$, S(=O)$_2$ R$^2$, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent CH$_2$ groups may be replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S or CONR$^3$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or a combination of these systems; at the same time, two or more adjacent $R^2$ substituents may also together form a mono- or polycyclic, aliphatic or aromatic ring system;

$R^3$ is the same or different at each instance and is H, D, F, Cl, Br, I, N(R$^4$)$_2$, C(=O)Ar, P(=O)Ar$_2$, S(=O)Ar, S(=O)$_2$Ar, CR$^4$=CR$^4$Ar, CN, NO$_2$, Si(R$^4$)$_3$, B(OR$^4$)$_2$, OSO$_2$R$^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent CH$_2$ groups may be replaced by R$^4$C=CR$^4$, C≡C, Si(R$^4$)$_2$, C=O, C=NR$^4$, P(=O)(R$^4$), SO, SO$_2$, NR$^4$, O, S or CONR$^4$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^4$ radicals, or an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals, or a combination of these systems; at the same time, two or more adjacent $R^3$ substituents may also together form a mono- or polycyclic, aliphatic or aromatic ring system;

$R^4$ is the same or different at each instance and is H, D, F or an aliphatic hydrocarbyl radical having 1 to 20 carbon atoms or an aryl or heteroaryl group which has 5 to 40 ring atoms and may be substituted by one or more $R^5$ radicals, or a combination of these groups;

$R^5$ is the same or different at each instance and is H, D, F or an aliphatic hydrocarbyl radical having 1 to 20 carbon atoms;

q is 0, 1 or 2;

where $Ar^2$ in the case of a heteroaromatic ring system may be joined to the phenanthridine base skeleton via a C—C bond; and, $R^1$ in the case of a heteroaromatic ring system may be joined to the phenanthridine base skeleton via a C—C bond.

2. The device according to claim 1, wherein the compound is of formula (2)
Formula (2)
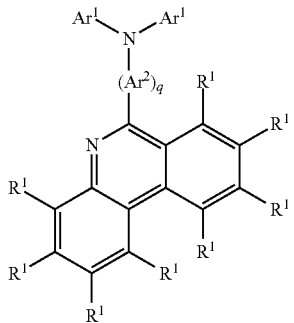
where the symbols and indices have the definitions given in claim 1.
3. The device according to claim 2, wherein the compound isone of the formulae (3) to (8):
Formula (3)
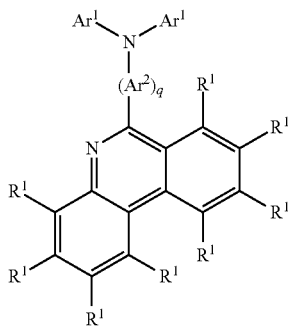
Formula (4)
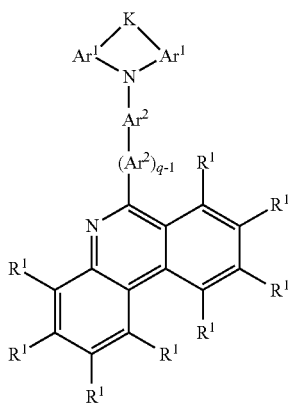
Formula (5)
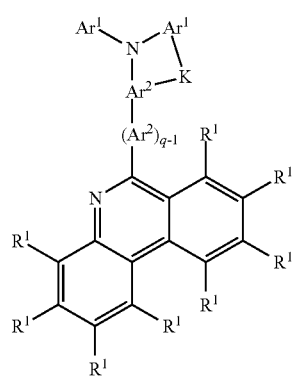
Formula (6)
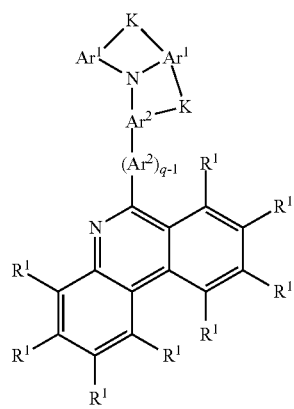
Formula (7)
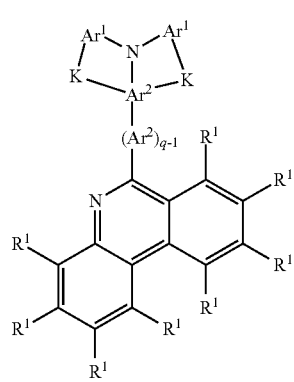
Formula (8)
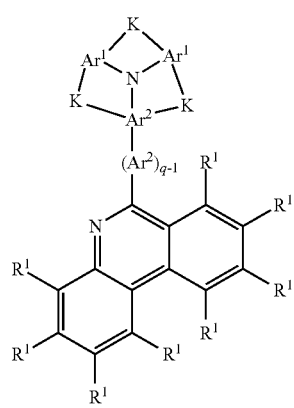

where the symbols and indices have the definitions given in claim 2 and, in addition, the two $Ar^1$ are not joined to one another and $Ar^1$ is not joined to $Ar^2$ by further K groups and, in the formulae (4), (5), (6), (7) and (8), q>0.

4. A mixture comprising at least one compound of formula (1)

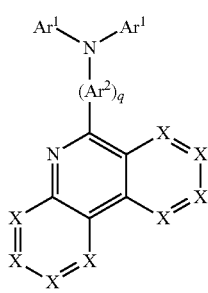

Formula (1)

where the symbols and indices used are as follows:
$Ar^1$ are the same or different at each instance and are an aromatic or heteroaromatic ring system which has 6 to 60 aromatic ring atoms and may in each case also be substituted by one or more $R^2$ radicals, where, in the case that q>0, at least the two $Ar^1$ may be joined and/or $Ar^1$ may be joined to $Ar^2$ via at least one bridge K;
K is the same or different at each instance and is a single bond or a bivalent bridge selected from $N(R^2)$, $B(R^2)$, O, C=O, $C(R^2)_2$, $Si(R^2)_2$, and S;
$Ar^2$ is the same or different at each instance and is a bivalent aromatic or heteroaromatic ring system which has 5 to 40 aromatic ring atoms and may be substituted by one or more $R^2$ radicals;
X is the same or different at each instance and is N or $CR^1$;
$R^1$ is the same or different at each instance and is H, D, F, Cl, Br, I, CHO, C(=O)Ar, P(=O)(Ar)$_2$, S(=O)Ar, S(=O)$_2$Ar, CN, NO$_2$, Si(R$^2$)$_3$, B(OR$^2$)$_2$, OSO$_2$R$^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by C≡C, Si(R$^2$)$_2$, Ge(R$^2$)$_2$, Sn(R$^2$)$_2$, C=O, C=S, C=Se, P(=O)(R$^2$), SO, SO$_2$, O, S or CONR$^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents may also together form a mono- or polycyclic, aliphatic or aromatic ring system;
Ar is the same or different at each instance and is an aromatic or heteroaromatic ring system which has 6 to 60 aromatic ring atoms and may in each case also be substituted by one or more $R^2$ radicals;

$R^2$ is the same or different at each instance and is H, D, F, Cl, Br, I, CHO, C(=O)R$^3$, P(=O) (R$^3$)$_2$, S(=O) R$^3$, S(=O)$_2$ R$^2$, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent CH$_2$ groups may be replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S or CONR$^3$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^3$ radicals, or an aryloxy or heteroaryloxy group which has 5 to 40 aromatic ring atoms and may be substituted by one or more $R^3$ radicals, or a combination of these systems; at the same time, two or more adjacent $R^2$ substituents may also together form a mono- or polycyclic, aliphatic or aromatic ring system;
$R^3$ is the same or different at each instance and is H, D, F, Cl, Br, I, N(R$^4$)$_2$, C(=O)Ar, P(=O)Ar$_2$, S(=O)Ar, S(=O)$_2$Ar, CR$^4$=CR$^4$Ar, CN, NO$_2$, Si(R$^4$)$_3$, B(OR$^4$)$_2$, OSO$_2$R$^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent CH$_2$ groups may be replaced by R$^4$C=CR$^4$, C≡C, Si(R$^4$)$_2$, C=O, C=NR$^4$, P(=O)(R$^4$), SO, SO$_2$, NR$^4$, O, S or CONR$^4$ and where one or more hydrogen atoms may be replaced by D, F, Cl, Br, I, CN or NO$_2$, or an aromatic or heteroaromatic ring system which has 5 to 60 aromatic ring atoms, each of which may be substituted by one or more $R^4$ radicals, or an aryloxy or heteroaryloxy group which has 5 to 40 aromatic ring atoms and may be substituted by one or more $R^4$ radicals, or an aralkyl or heteroalkyl group which has 5 to 40 aromatic ring atoms and may be substituted by one or more $R^4$ radicals, or a combination of these systems; at the same time, two or more adjacent $R^3$ substituents may also together form a mono- or polycyclic, aliphatic or aromatic ring system;
$R^4$ is the same or different at each instance and is H, D, F or an aliphatic hydrocarbyl radical having 1 to 20 carbon atoms or an aryl or heteroaryl group which has 5 to 40 ring atoms and may be substituted by one or more $R^5$ radicals, or a combination of these groups;
$R^5$ is the same or different at each instance and is H, D, F or an aliphatic hydrocarbyl radical having 1 to 20 carbon atoms;
q is 0, 1 or 2;
where
$Ar^2$ in the case of a heteroaromatic ring system may be joined to the phenanthridine base skeleton via a C—C bond; and,
$R^1$ in the case of a heteroaromatic ring system may be joined to the phenanthridine base skeleton via a C—C bond and at least one fluorescent or phosphorescent dopant.

5. The mixture according to claim 4, wherein the compound is of formula (2)

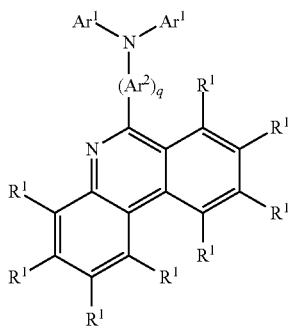

Formula (2)

where the symbols and indices have the definitions given in claim 4.

6. The mixture according to claim 4, wherein the compound is one of the formulae (3) to (8):

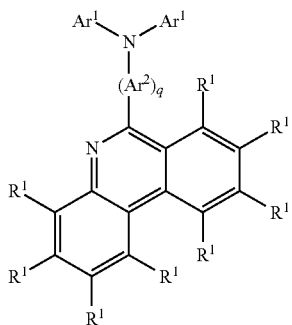

Formula (3)

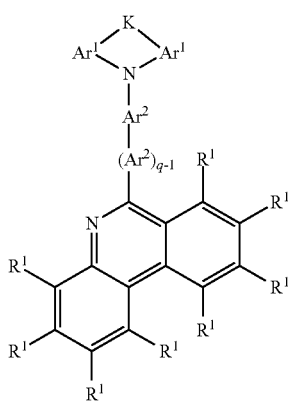

Formula (4)

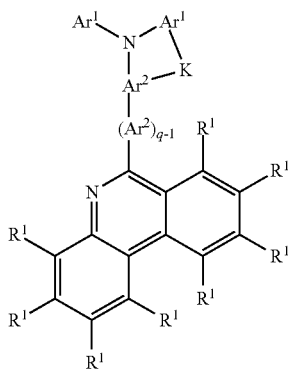

Formula (5)

-continued

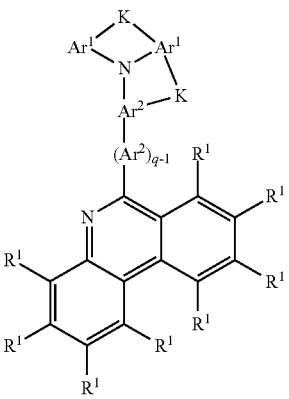

Formula (6)

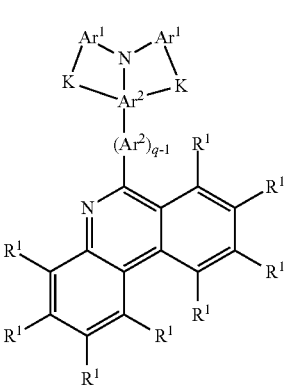

Formula (7)

Formula (8)

where the symbols and indices have the definitions given in claim 4 and, in addition, the two Ar¹ are not joined to one another and Ar¹ is not joined to Ar$^e$ by further K groups and, in the formulae (4), (5), (6), (7) and (8), q>0.

* * * * *